(12) United States Patent
Constantz et al.

(10) Patent No.: US 9,714,406 B2
(45) Date of Patent: Jul. 25, 2017

(54) CARBON SEQUESTRATION METHODS AND SYSTEMS, AND COMPOSITIONS PRODUCED THEREBY

(71) Applicant: Blue Planet, Ltd., Los Gatos, CA (US)

(72) Inventors: Brent Richard Constantz, Portola Valley, CA (US); Mark Bewernitz, Los Gatos, CA (US); Jacob Schneider, San Jose, CA (US); Chris Camire, Morgan Hill, CA (US)

(73) Assignee: Blue Planet, Ltd., Los Gatos, CA (US)

( * ) Notice: Subject to any disclaimer, the term of this patent is extended or adjusted under 35 U.S.C. 154(b) by 274 days.

(21) Appl. No.: 14/112,495

(22) PCT Filed: Sep. 4, 2013

(86) PCT No.: PCT/US2013/058090
§ 371 (c)(1),
(2) Date: Oct. 17, 2013

(87) PCT Pub. No.: WO2014/039578
PCT Pub. Date: Mar. 13, 2014

(65) Prior Publication Data
US 2014/0234946 A1    Aug. 21, 2014

Related U.S. Application Data

(60) Provisional application No. 61/696,372, filed on Sep. 4, 2012, provisional application No. 61/732,855, filed
(Continued)

(51) Int. Cl.
C01B 31/20    (2006.01)
C01F 11/18    (2006.01)
(Continued)

(52) U.S. Cl.
CPC .............. *C12M 29/00* (2013.01); *B01D 53/18* (2013.01); *B01D 53/62* (2013.01); *B01D 53/78* (2013.01);
(Continued)

(58) Field of Classification Search
CPC ....... C04B 22/106; C04B 28/04; C04B 18/08; B01D 2251/402; B01D 2251/404;
(Continued)

(56) References Cited

U.S. PATENT DOCUMENTS 4,112,052 A    9/1978   Sartori et al.
4,729,883 A    3/1988   Lam et al.
(Continued)

FOREIGN PATENT DOCUMENTS

EP    1546319 A1    6/2005
FR    2830249 A1    4/2003
(Continued)

OTHER PUBLICATIONS

Google search results for alkalinity of bicarbonate accessed Sep. 18, 2016.*
(Continued)

*Primary Examiner* — Christopher P Jones
*Assistant Examiner* — Cabrena Holecek
(74) *Attorney, Agent, or Firm* — Bret E. Field; Bozicevic, Field & Francis LLP

(57) ABSTRACT

Aspects of the invention include methods of removing carbon dioxide ($CO_2$) from a $CO_2$ containing gas. In some instances, the methods include contacting $CO_2$ containing gas with a bicarbonate buffered aqueous medium under conditions sufficient to produce a bicarbonate rich product. Where desired, the resultant bicarbonate rich product or a component thereof may then be stored or further processed, e.g., combined with a divalent alkaline earth metal cation,
(Continued)

under conditions sufficient to produce a solid carbonate composition. Aspects of the invention further include systems for practicing the methods, as well as products produced by the methods.

22 Claims, 16 Drawing Sheets

Related U.S. Application Data on Dec. 3, 2012, provisional application No. 61/793,512, filed on Mar. 15, 2013, provisional application No. 61/809,165, filed on Apr. 5, 2013, provisional application No. 61/793,585, filed on Mar. 15, 2013, provisional application No. 61/793,731, filed on Mar. 15, 2013, provisional application No. 61/807,230, filed on Apr. 1, 2013, provisional application No. 61/819,427, filed on May 3, 2013, provisional application No. 61/844,808, filed on Jul. 10, 2013, provisional application No. 61/866,988, filed on Aug. 16, 2013, provisional application No. 61/844,809, filed on Jul. 10, 2013.

(51) Int. Cl.

| | | |
|---|---|---|
| C01F 5/24 | (2006.01) | |
| C12M 1/00 | (2006.01) | |
| B01D 53/62 | (2006.01) | |
| B01D 53/78 | (2006.01) | |
| B01D 53/18 | (2006.01) | |
| C04B 22/10 | (2006.01) | |
| C04B 28/04 | (2006.01) | |
| C12M 1/40 | (2006.01) | |
| C01B 31/24 | (2006.01) | |

(52) U.S. Cl.
CPC ............ *C01B 31/20* (2013.01); *C01B 31/24* (2013.01); *C01F 5/24* (2013.01); *C01F 11/18* (2013.01); *C01F 11/181* (2013.01); *C04B 22/106* (2013.01); *C04B 28/04* (2013.01); *C12M 21/18* (2013.01); *B01D 2251/402* (2013.01); *B01D 2251/404* (2013.01); *B01D 2257/504* (2013.01); *C01P 2002/72* (2013.01); *Y02C 10/04* (2013.01); *Y02C 10/06* (2013.01); *Y02P 20/152* (2015.11); *Y02W 30/92* (2015.05)

(58) Field of Classification Search
CPC .. B01D 2257/504; B01D 53/18; B01D 53/62; B01D 53/78; C01B 31/24; C12M 21/18; C12M 29/00; Y02C 10/04; Y02C 10/06
See application file for complete search history.

(56) References Cited

U.S. PATENT DOCUMENTS

| | | | |
|---|---|---|---|
| 6,217,851 B1 | 4/2001 | Kleinberg et al. | |
| 6,908,507 B2 * | 6/2005 | Lalande | B01D 53/62 |
| | | | 106/739 |
| 7,132,090 B2 | 11/2006 | Dziedzic et al. | |
| 7,596,952 B2 | 10/2009 | Fradette et al. | |
| 7,642,076 B2 | 1/2010 | Dziedzic et al. | |
| 7,998,714 B2 | 8/2011 | Gellett et al. | |
| 8,070,856 B2 | 12/2011 | Rochelle et al. | |
| 8,394,350 B2 | 3/2013 | Aines | |
| 2001/0022952 A1 | 9/2001 | Rau et al. | |
| 2006/0128004 A1 * | 6/2006 | Anctil | C12P 3/00 |
| | | | 435/266 |
| 2006/0185985 A1 * | 8/2006 | Jones | B01D 53/1418 |
| | | | 205/508 |
| 2007/0218044 A1 | 9/2007 | Muller et al. | |
| 2009/0202410 A1 | 8/2009 | Kawatra et al. | |
| 2010/0068784 A1 | 3/2010 | Dziedzic et al. | |
| 2010/0300894 A1 * | 12/2010 | Lin | B01D 53/1425 |
| | | | 205/763 |
| 2011/0116998 A1 | 5/2011 | Van Straelen | |
| 2011/0151537 A1 * | 6/2011 | Lightstone | B01D 53/1475 |
| | | | 435/188 |
| 2011/0223650 A1 | 9/2011 | Saunders et al. | |
| 2012/0199535 A1 | 8/2012 | Valdez et al. | |
| 2012/0227630 A1 | 9/2012 | Gray | |
| 2012/0296117 A1 | 11/2012 | Wu | |
| 2012/0308457 A1 | 12/2012 | Yoon et al. | |
| 2013/0101493 A1 | 4/2013 | Okabe et al. | |

FOREIGN PATENT DOCUMENTS

| | | | | |
|---|---|---|---|---|
| WO | WO 2008018928 A2 | 2/2008 | | |
| WO | WO 2008148055 A1 | 12/2008 | | |
| WO | WO 2009086460 A1 | 7/2009 | | |
| WO | WO 2009146436 A1 | 12/2009 | | |
| WO | WO 2009155378 A1 | 12/2009 | | |
| WO | WO 2010006242 A1 | 1/2010 | | |
| WO | WO 2010014774 A2 * | 2/2010 | ......... | B01D 53/1475 |
| WO | WO 2010039903 A1 | 4/2010 | | |
| WO | WO 2010039909 A1 | 4/2010 | | |
| WO | WO 2010048457 A1 | 4/2010 | | |
| WO | WO 2010051458 A1 | 5/2010 | | |
| WO | WO 2010068924 A1 | 6/2010 | | |
| WO | WO 2010091029 A1 | 8/2010 | | |
| WO | WO 2010101953 A1 | 9/2010 | | |
| WO | WO 2010104989 A1 | 9/2010 | | |
| WO | WO 2010132863 A1 | 11/2010 | | |
| WO | WO 2011017609 A1 | 2/2011 | | |
| WO | WO 2011049996 A1 | 4/2011 | | |
| WO | WO 2011081681 A1 | 7/2011 | | |
| WO | WO 2012005867 A1 | 1/2012 | | |
| WO | WO 2012018434 A1 | 2/2012 | | |
| WO | WO 2012079173 A1 | 6/2012 | | |
| WO | WO 2012149173 A2 | 11/2012 | | |

OTHER PUBLICATIONS

"Water, Alkalinity & pH" Mark Sircus, Oct. 17, 2011, see p. 1 graph.*
Berg, et al. "Mg2+ tunes the wettability of liquid precursors of CaCO3: Towards controlling mineralization sites in hybrid materials", J Am Chem Soc (Aug. 2013), 135(34):12512-12515.
Berner, et al. "The Carbonate-silicate geochemical cycle and its effect on atmospheric carbon dioxide over the past 100 million years", American Journal of Science (Sep. 1983), 283:641-683.
Bewernitz, et al. "A metastable liquid precursor phase of calcium carbonate and its interactions with polyaspartate", The Royal Society of Chemistry (Jun. 2012), 159:291-312.
Bhaduri, et al. "Nickel nanoparticles catalyse reversible hydration of carbon dioxide for mineralization carbon capture and storage", Catal. Sci. Technol. (Jan. 2013), 3:1234-1239.
Bindeman, et al. "Oxygen Isotopes in Mantle and Crustal Magmas as Revealed by Single Crystal Analysis", Reviews in Mineralogy & Geochemistry (2008), 69:445-478.
Brehm, et al. "The role of microorganisms and biofilms in the breakdown and dissolution of quartz and glass", Palaeo (Apr. 2005), 219(1-2):117-129.
Caldeira, et al. "Ocean storage", IPCC Special Report on Carbon dioxide Capture and Storage (2006), ISBN: 0521685516.
Combes, et al. "Calcium Carbonate Biphasic Cement Concept to Control Cement Resorption", European Cells and Materials (2006),11:8.
Combes, et al. "Preparation, physical-chemical characterisation and cytocompatibility of calcium carbonate cements", Biomaterials (Sep. 2006), 1945-1954.
"Corporate and Technology Presentation", CO2 Solutions Inc (Nov. 2012).
Dorvee, et al. "Water in the formation of biogenic minerals: Peeling away the hydration layers", J Struct Biol (Aug. 2013), 183(2):278-303.

(56) References Cited

OTHER PUBLICATIONS

Dunsmore, et al. "A geological perspective on global warming and the possibility of carbon dioxide removal as calcium carbonate mineral", Energy Conyers Mgmt (1992), 33(5-8):565-572.

Ehrlich, et al. "Modern Views on Desilicification: Biosilica and Abiotic Silica Dissolution in Natural and Artificial Environments", Chem Rev (2010), 110:4656-4689.

England, et al. "On the hydration and hydrolysis of carbon dioxide", Chemical Physics Letters (2011), 514:187-195.

Garcia-Ruiz, et al. "Morphogenesis of Self-Assembled Nanocrystalline Materials of Barium Carbonate and Silica", Science (Jan. 2009), 323:362-365.

Gebauer, et al. "Prenucleation clusters and non-classical nucleation", Nano Today (Jun. 2011), 6:564-584.

Gebauer, et al. "Stable Prenucleation Calcium Carbonate Clusters", Science (Dec. 2008), 322(5909):1819-1822.

Greene, et al. "Chemical Admixtures for Concrete: Prepared under the direction and supervision of ACI Committee E-701, Materials for Concrete Construction", ACI Education Bulletin E3-13 (Aug. 2013), E31-E326.

El-Hassan, "Reaction Products in Carbonation-Cured Lightweight Concrete," Journal of Materials in Civil Engineering (Jun. 2013), 25(6):799-809.

Hoboi, et al. "Low temperature solidification of calcium carbonate through vaterite-calcite wet transformation," Journal of Materials Science Letters (May 1996),15(9):812-814.

Hu, et al. "The thermodynamics of calcite nucleation at organic interfaces: Classical vs. non-classical pathways", Faraday Discuss (2012), 159:509-523.

Kozoil, et al. "Toward a Small Molecule, Biomimetic Carbonic Anhydrase Model: Theoretical and Experimental Investigations of a Panel of Zinc(II) Aza-Macrocyclic Catalysts", Inorg Chem (Jun. 2012), 51(12):6803-6812.

Masse, et al. "Modification of the Stöber Process by a Polyazamacrocycle Leading to Unusual Core—Shell Silica Nanoparticles", Langmuir (2008), 24:4026-4031.

McGrath, et al. "Sea urchin nickel 'trick' could be key to capturing carbon", BBC News (Feb. 2013), 1-2.

Meldrum, et al. "Now You See Them", Science (Dec. 2008), 322(5909):1802-1803.

Park, et al. "Density, Viscosity, and Solubility of CO2 in Aqueous Solutions of 2-Amino-2-hydroxymethyl-1-1,3-propanediol", J. Chem. Eng (2002), 47:970-973.

Park, et al. "Effect of steric hindrance on carbon dioxide absorption into new amine solutions: thermodynamic and spectroscopic verification through solubility and NMR analysis", Environ Sci Technol (2003), 37:1670-1675.

Schroder, et al. "Silicateins, silicase and spicule-associated proteins: synthesis of demosponge silica skeleton and nanobiotechnological applications", Porfeira Research: Biodiversity, Innovation, and Sustainability (2007), 581-592.

Schumacher, et al. "Oxygen isotopic signature of CO2 from combustion processes", Atmos Chem Phys (2011), 1473-1490.

Su, et al. "Structural characterization of amorphous calcium carbonate-binding protein: an insight into the mechanism of amorphous calcium carbonate formation", Biochem J (2013), 453:179-186.

Zuddas, et al. "Kinetics of calcite precipitation from seawater: I. A classical chemical kinetics description for strong electrolyte solutions", Pergamon (1994), 58(20):4353-4362.

Bachu, S. "CO2 storage in geological media: Role, means, status and barriers to deployment", Progress in Energy and Combustion Science 34, 2008, pp. 254-273.

"Experimental Investigation of calcium and bicarbonate ions can react", 2006, 1 page, Author Unknown. (Machine Translation retrieved from China Education Resource Service Platform (CERSP), http://chem.cersp.com/HXJS/200608/1249.html, Aug. 29, 2016, 4 pages).

* cited by examiner

Diameter of LCP Droplet

Zeta Potential of BRLCP Droplets (ξ)

US 9,714,406 B2

CARBON SEQUESTRATION METHODS AND SYSTEMS, AND COMPOSITIONS PRODUCED THEREBY

CROSS REFERENCE TO RELATED APPLICATIONS

Pursuant to 35 U.S.C. §119 (e), this application claims priority to the filing dates of: U.S. Provisional Application No. 61/696,372, filed Sep. 4, 2012; U.S. Provisional Application No. 61/732,855 filed Dec. 3, 2012; U.S. Provisional Application No. 61/793,512 filed Mar. 15, 2013; U.S. Provisional Application No. 61/809,165 filed Apr. 5, 2013; U.S. Provisional Application No. 61/793,585 filed Mar. 15, 2013; U.S. Provisional Application No. 61/793,731 filed Mar. 15, 2013; U.S. Provisional Application No. 61/807,230 filed on Apr. 1, 2013; U.S. Provisional Application No. 61/819,427 filed on May 3, 2013; U.S. Provisional Application No. 61/844,808 filed on Jul. 10, 2013; U.S. Provisional Application No. 61/866,988 filed on Aug. 16, 2013; and U.S. Provisional Application No. 61/844,809 filed on Jul. 10, 2013; the disclosures of which applications are incorporated herein by reference.

INTRODUCTION

Carbon dioxide ($CO_2$) is a naturally occurring chemical compound that is present in Earth's atmosphere as a gas. Sources of atmospheric $CO_2$ are varied, and include humans and other living organisms that produce $CO_2$ in the process of respiration, as well as other naturally occurring sources, such as volcanoes, hot springs, and geysers.

Additional major sources of atmospheric $CO_2$ include industrial plants. Many types of industrial plants (including cement plants, refineries, steel mills and power plants) combust various carbon-based fuels, such as fossil fuels and syngases. Fossil fuels that are employed include coal, natural gas, oil, petroleum coke and biofuels. Fuels are also derived from tar sands, oil shale, coal liquids, and coal gasification and biofuels that are made via syngas.

The environmental effects of $CO_2$ are of significant interest. $CO_2$ is commonly viewed as a greenhouse gas. Because human activities since the industrial revolution have rapidly increased concentrations of atmospheric $CO_2$, anthropogenic $CO_2$ has been implicated in global warming and climate change, as well as increasing oceanic bicarbonate concentration. Ocean uptake of fossil fuel $CO_2$ is now proceeding at about 1 million metric tons of $CO_2$ per hour.

Sequestration of anthropogenic $CO_2$ is of great global urgency and is important in efforts to slow or reverse global warming and ocean acidification. Current approaches of carbon capture and geological sequestration have proven impractical, expensive, and with limited volume potential, as well as potentially dangerous. Carbonate mineralization has emerged as the best potential method to sequester large amounts of $CO_2$, e.g., in gigaton volumes, sustainably. However, challenges in raw material inputs and energy balances with currently developed carbonate mineralization processes have limited the applicability of the method. In some approaches, the most significant limitation is the requirement of two mols of alkalinity for every mol of absorbed carbon dioxide to convert carbonic acid to carbonate. This approach requires the delivery of alkalinity to the site of absorption or the production of alkalinity via energy intensive processes like electrochemical production of sodium hydroxide. This limitation restricts the carbonate mineralization approach to a few locations where rare raw materials are cheaply available, or hope of further development of electrochemical techniques to produce alkalinity (Service R. F., "Pave the World!", Science (2012) 337: 676-678).

As such, there is continued interest in the development of new $CO_2$ sequestration technologies.

SUMMARY

Aspects of the invention include methods of removing carbon dioxide ($CO_2$) from a $CO_2$ containing gas. In some instances, the methods include contacting a $CO_2$ containing gas with an aqueous medium under conditions sufficient to remove $CO_2$ from the gaseous stream and produce a bicarbonate-rich product (BRP), which may include droplets of a liquid condensed phase (LCP) in a bulk medium. The resultant product or component thereof, e.g., LCP, may be stored, used in a variety of applications and/or further processed, as desired. Aspects of the invention further include systems for practicing the methods, as well as products produced by the subject methods.

Aspects of the invention include methods of sequestering $CO_2$ that require little, if any, added alkalinity, (i.e., the methods do not require large amounts of alkalinity, or the methods require no added alkalinity), and yet yield a net sequestration of $CO_2$. In some aspects, the methods produce carbonate minerals, including carbonate minerals with useful applications, such as cement and aggregate for building roads and the like, e.g., as described in greater detail below, and purified $CO_2$.

DETAILED DESCRIPTION

Figure 1:
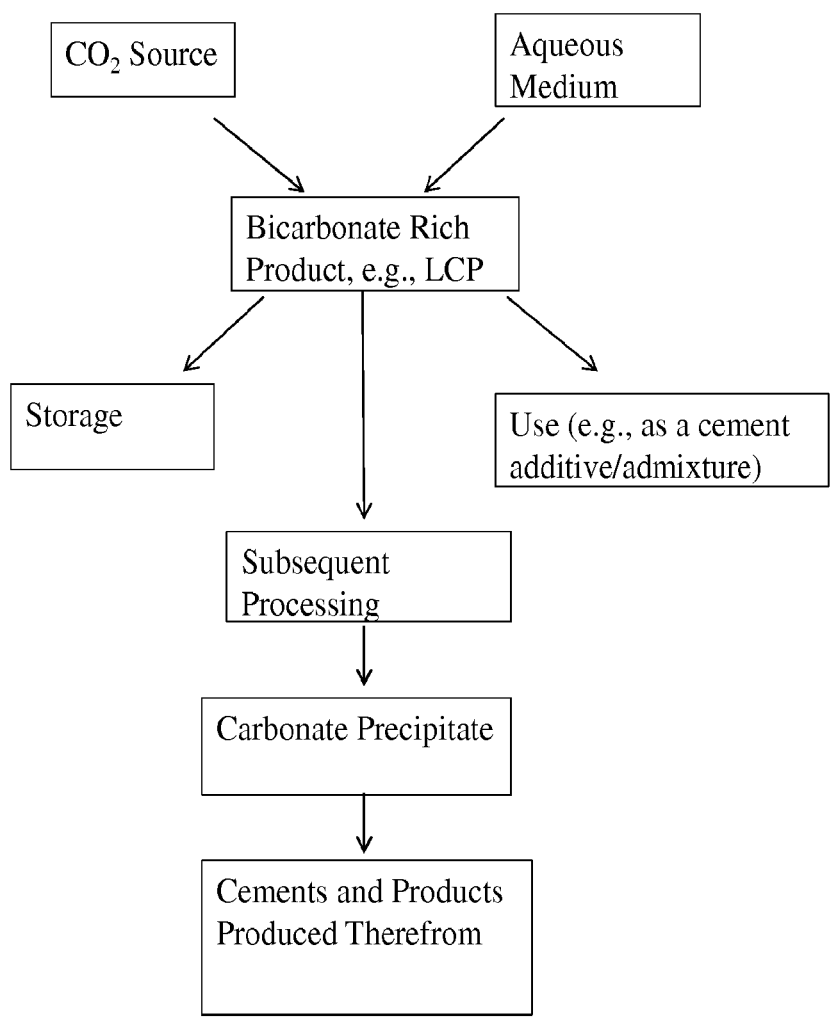
FIG. 1 provides an overview of a $CO_2$ sequestration process according to an embodiment of the invention.

Aspects of the invention include methods of removing carbon dioxide ($CO_2$) from a $CO_2$ containing gas. In some instances, the methods include contacting a $CO_2$ containing gaseous stream with an aqueous medium under conditions sufficient to produce a bicarbonate-rich product (BRP), which product may include droplets of a liquid condensed phase (LCP) in a bulk medium. The resultant product or component thereof, e.g., LCP, may be stored, used in a variety of applications and/or further processed, as desired. Aspects of the invention further include systems for practicing the methods, as well as products produced by the subject methods.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating un-recited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

OVERVIEW

As summarized above, aspects of the invention are directed to methods of removing $CO_2$ from a $CO_2$ containing gas. Various embodiments of the invention are illustrated FIG. 1, where each of the components of FIG. 1 are described in greater detail below. As shown in FIG. 1, a $CO_2$ containing gas and an aqueous medium are combined under conditions sufficient to produce a bicarbonate rich product (BRP), which product may include droplets of a liquid condensed phase (LCP) in a bulk medium. The resultant bicarbonate rich product may be stored, used "as is" in a variety of different applications, or further processed, e.g., combined with other materials to produce a useful product, subjected to carbonate precipitation conditions, etc., where the resultant carbonate precipitate may in turn be further used in a variety of products, e.g., as a cement, to produce aggregate, purified $CO_2$ etc. The various aspects of the invention are now described in greater detail below.

Methods

Aspects of the invention include methods of removing $CO_2$ from a $CO_2$ containing gas. In other words, methods of separating $CO_2$ from a $CO_2$ containing gas are provided, where an input gas containing $CO_2$ is processed to produce an output gas that has less $CO_2$ than the input gas. The output gas of the methods described herein may be referred to as "$CO_2$ depleted gas." The amount of $CO_2$ in the $CO_2$ depleted gas is less than the amount of $CO_2$ that is present in the input $CO_2$ containing gas, where in some instances the amount of $CO_2$ in the $CO_2$ depleted gas is 95% or less, e.g., 90% or less, 85% or less, 80% or less, 75% or less, 70% or less, 65% or less, 60% or less, 55% or less, 50% or less, 45% or less, 40% or less, 35% or less, 30% or less, 25% or less, 20% or less, 15% or less, 10% or less, 5% or less, than the amount of $CO_2$ that is present in the input $CO_2$ containing gas.

In removing $CO_2$ from a $CO_2$ containing gas, the $CO_2$ containing gas is contacted with an aqueous medium under conditions sufficient to produce a bicarbonate rich product.

CO₂ Containing Gasses

The CO$_2$ containing gas that is processed in methods of the invention is one that includes CO$_2$. The CO$_2$ containing gas may be pure CO$_2$ or be combined with one or more other gasses and/or particulate components, depending upon the source, e.g., it may be a multi-component gas (i.e., a multi-component gaseous stream). While the amount of CO$_2$ in such gasses may vary, in some instances the CO$_2$ containing gasses have a pCO$_2$ of $10^3$ or higher, such as $10^4$ Pa or higher, such as $10^5$ Pa or higher, including $10^6$ Pa or higher. The amount of CO$_2$ in the CO$_2$ containing gas, in some instances, may be 20,000 or greater, e.g., 50,000 ppm or greater, such as 100,000 ppm or greater, including 150,000 ppm or greater, e.g., 500,000 ppm or greater, 750,000 ppm or greater, 900,000 ppm or greater, up to including 1,000,000 ppm or greater (In pure CO$_2$ exhaust the concentration is 1,000,000 ppm) In some instances may range from 10,000 to 500,000 ppm, such as 50,000 to 250,000 ppm, including 100,000 to 150,000 ppm. The temperature of the CO$_2$ containing gas may also vary, ranging in some instances from 0 to 1800° C., such as 100 to 1200° C. and including 600 to 700° C.

As indicated above, in some instances the CO$_2$ containing gasses are not pure CO$_2$, in that they contain one or more additional gasses and/or trace elements. Additional gasses that may be present in the CO$_2$ containing gas include, but are not limited to water, nitrogen, mononitrogen oxides, e.g., NO, NO$_2$ and NO$_3$, oxygen, sulfur, monosulfur oxides, e.g., SO, SO$_2$ and SO$_3$), volatile organic compounds, e.g., benzo(a)pyrene C$_2$OH$_{12}$, benzo(g,h,l)perylene C$_{22}$H$_{12}$, dibenzo(a, h)anthracene C$_{22}$H$_{14}$, etc. Particulate components that may be present in the CO$_2$ containing gas include, but are not limited to particles of solids or liquids suspended in the gas, e.g., heavy metals such as strontium, barium, mercury, thallium, etc.

In certain embodiments, CO$_2$ containing gasses are obtained from an industrial plant, e.g., where the CO$_2$ containing gas is a waste feed from an industrial plant. Industrial plants from which the CO$_2$ containing gas may be obtained, e.g., as a waste feed from the industrial plant, may vary. Industrial plants of interest include, but are not limited to, power plants and industrial product manufacturing plants, such as but not limited to chemical and mechanical processing plants, refineries, cement plants, steel plants, etc., as well as other industrial plants that produce CO$_2$ as a byproduct of fuel combustion or other processing step (such as calcination by a cement plant). Waste feeds of interest include gaseous streams that are produced by an industrial plant, for example as a secondary or incidental product, of a process carried out by the industrial plant.

Of interest in certain embodiments are waste streams produced by industrial plants that combust fossil fuels, e.g., coal, oil, natural gas, as well as man-made fuel products of naturally occurring organic fuel deposits, such as but not limited to tar sands, heavy oil, oil shale, etc. In certain embodiments, power plants are pulverized coal power plants, supercritical coal power plants, mass burn coal power plants, fluidized bed coal power plants, gas or oil-fired boiler and steam turbine power plants, gas or oil-fired boiler simple cycle gas turbine power plants, and gas or oil-fired boiler combined cycle gas turbine power plants. Of interest in certain embodiments are waste streams produced by power plants that combust syngas, i.e., gas that is produced by the gasification of organic matter, e.g., coal, biomass, etc., where in certain embodiments such plants are integrated gasification combined cycle (IGCC) plants. Of interest in certain embodiments are waste streams produced by Heat Recovery Steam Generator (HRSG) plants. Waste streams of interest also include waste streams produced by cement plants. Cement plants whose waste streams may be employed in methods of the invention include both wet process and dry process plants, which plants may employ shaft kilns or rotary kilns, and may include pre-calciners. Each of these types of industrial plants may burn a single fuel, or may burn two or more fuels sequentially or simultaneously. A waste stream of interest is industrial plant exhaust gas, e.g., a flue gas. By "flue gas" is meant a gas that is obtained from the products of combustion from burning a fossil or biomass fuel that are then directed to the smokestack, also known as the flue of an industrial plant.

Aqueous Media

As summarized above, in practicing methods described herein, the CO$_2$ containing gas is contacted with an aqueous medium to remove CO$_2$ from the CO$_2$ containing gas. While the aqueous medium may vary depending on the particular protocol being performed, aqueous media of interest include pure water as well as water that includes one or more solutes, e.g., divalent cations, such as Mg$^{2+}$, Ca$^{2+}$, counterions, e.g., carbonate, hydroxide, etc., where in some instances the aqueous medium may be a bicarbonate buffered aqueous medium. Bicarbonate buffered aqueous media employed in methods of the invention include liquid media in which a bicarbonate buffer is present. As such, liquid aqueous media of interest include dissolved CO$_2$, water, carbonic acid (H$_2$CO$_3$), bicarbonate ions (HCO$_3^-$), protons (H$^+$) and carbonate ions (CO$_3^{2-}$). The constituents of the bicarbonate buffer in the aqueous media are governed by the equation:

$$CO_2 + H_2O \rightleftharpoons H_2CO_3 \rightleftharpoons H^+ + HCO_3^- \rightleftharpoons 2H^+ + CO_3^{2-}$$

In aqueous media of interest, the amounts of the different carbonate species components in the media may vary according to the pH. In some instances below around or about pH 4.5, the amount of carbonic acid ranges from 50 to 100%, such as 70 to 90%, the amount of bicarbonate ion around or about pH 4-9 ranges from 10 to 95%, such as 20 to 90% and the amount of carbonate ion above around or about pH 9 ranges from 10 to 100%, such as 10 to 70%. The pH of the aqueous media may vary, ranging in some instances from 7 to 11, such as 8 to 11, e.g., 8 to 10, e.g., 8 to 9.5, such as 8 to 9.3, including 8 to 9. In some instances, the pH ranges from 8.2 to 8.7, such as from 8.4 to 8.55.

The aqueous medium may be a naturally occurring or man-made medium, as desired. Naturally occurring bicarbonate buffered aqueous media include, but are not limited to, waters obtained from seas, oceans, lakes, swamps, estuaries, lagoons, brines, alkaline lakes, inland seas, etc. Man-made sources of bicarbonate buffered aqueous media may also vary, and may include brines produced by water desalination plants, and the like. Of interest in some instances are waters that provide for excess alkalinity, which is defined as alkalinity which is provided by sources other than bicarbonate ion. In these instances, the amount of excess alkalinity may vary, so long as it is sufficient to provide 1.0 or slightly less, e.g., 0.9, equivalents of alkalinity. Waters of interest include those that provide excess alkalinity (meq/liter) of 30 or higher, such as 40 or higher, 50 or higher, 60 or higher, 70 or higher, 80 or higher, 90 or higher, 100 or higher, etc. Where such waters are employed, no other source of alkalinity, e.g., NaOH, is required.

In some instances, the aqueous medium that is contacted with the CO$_2$ containing gas is one which, in addition to the bicarbonate buffering system (e.g., as described above), further includes an amount of divalent cations. Inclusion of divalent cations in the aqueous media can allow the concentration of bicarbonate ion in the bicarbonate rich product to be increased, thereby allowing a much larger amount of $CO_2$ to become sequestered as bicarbonate ion in the bicarbonate rich product. In such instances, bicarbonate ion concentrations that exceed 5,000 ppm or greater, such as 10,000 ppm or greater, including 15,000 ppm or greater may be achieved. For instance, calcium and magnesium occur in seawater at concentrations of 400 and 1200 ppm respectively. Through the formation of a bicarbonate rich product using seawater (or an analogous water as the aqueous medium), bicarbonate ion concentrations that exceed 10,000 ppm or greater may be achieved.

In such embodiments, the total amount of divalent cation source in the medium, which divalent cation source may be made up of a single divalent cation species (such as $Ca^{2+}$, $Mg^{2+}$) or two or more distinct divalent cation species (e.g., $Ca^{2+}$, $Mg^{2+}$, etc.), may vary, and in some instances is 1000 ppm or greater, such as 2000 ppm or greater, including 3000 ppm or greater, such as 5000 ppm or greater, including 7500 ppm or greater, such as 10,000 ppm or greater, e.g., 15,000 ppm or greater, including 20,000 ppm or greater. Divalent cations of interest that may be employed, either alone or in combination, as the divalent cation source include, but are not limited to: $Ca^{2+}$, $Mg^{2+}$, $Be^{2+}$, $Ba^{2+}$, $Sr^{2+}$, $Pb^{2+}$, $Fe^{2+}$, $Hg^{2+}$, and the like. Other cations of interest that may or may not be divalent include, but are not limited to: $Na^+$, $K^+$, $NH_4^+$, and $Li^+$, as well as cationic species of Mn, Ni, Zn, Cu, Ce, La, Al, Y, Nd, Zr, Gd, Dy, Ti, Th, U, La, Sm, Pr, Co, Cr, Te, Bi, Ge, Ta, As, Nb, W, Mo, V, etc. Naturally occurring aqueous media which include a cation source, divalent or otherwise, and therefore may be employed in such embodiments include, but are not limited to: aqueous media obtained from seas, oceans, estuaries, lagoons, brines, alkaline lakes, inland seas, etc.

Production of Bicarbonate Rich Product (BRP)

Contact of the $CO_2$ containing gas and bicarbonate buffered aqueous medium is carried out under conditions sufficient to remove $CO_2$ from the $CO_2$ containing gas (i.e., the $CO_2$ containing gaseous stream), and increase the bicarbonate ion concentration of the aqueous medium to produce a bicarbonate rich product. By bicarbonate rich product is meant a composition characterized by high concentrations of bicarbonate ion, where the concentration of bicarbonate ion may, in some instances, be 5,000 ppm or greater, such as 10,000 ppm or greater, including 15,000 ppm or greater. In some instances, the bicarbonate ion in the bicarbonate rich products ranges from 5,000 to 20,000 ppm, such as 7,500 to 15,000 ppm, including 8,000 to 12,000 ppm. In some instances, the overall amount of bicarbonate ion in the BRLCP may range from 0.1 wt. % to 30 wt. %, such as 3 to 20 wt. %, including from 10 to 15 wt. %. The pH of the bicarbonate rich product produced upon combination of the $CO_2$ source and aqueous medium, e.g., as described above, may vary, and in some instances range from 4 to 10, such as 6 to 9 and including 8 to 8.5.

The bicarbonate rich product may be a liquid composition that includes a single phase or two or more different phases. In some embodiments, the bicarbonate rich product includes droplets of a liquid condensed phase (LCP) in a bulk liquid, e.g., bulk solution. By "liquid condensed phase" or "LCP" is meant a phase of a liquid solution which includes bicarbonate ions wherein the concentration of bicarbonate ions is higher in the LCP phase than in the surrounding, bulk liquid.

Figure 2:
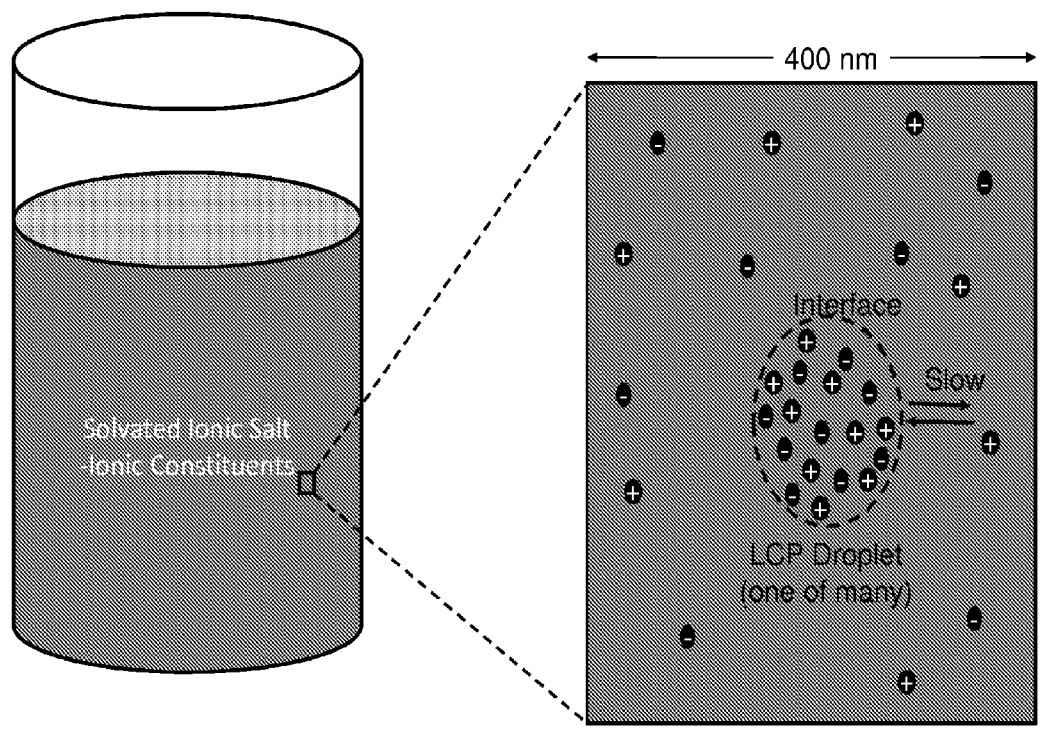
FIG. 2 provides a representation of a liquid condensed phase which may be present in bicarbonate rich products produced in methods of the invention.

LCP droplets are characterized by the presence of a meta-stable bicarbonate-rich liquid precursor phase in which bicarbonate ions associate into condensed concentrations exceeding that of the bulk solution and are present in a non-crystalline solution state. See e.g., FIG. 2. As can be seen in FIG. 2, the LCP contains all of the components found in the bulk solution that is outside of the interface represented by the dashed line. However, the concentration of the bicarbonate ions is higher than in the bulk solution. In those situations where LCP droplets are present, the LCP and bulk solution may each contain ion-pairs and pre-nucleation clusters (PNCs). When present, the ions remain in their respective phases for long periods of time, as compared to ion-pairs and PNCs in solution. While the number of droplets in a given BRP may vary, in some instances there are $1\times10^{-6}$ or more droplets/ml of liquid, such as $1\times10^{-7}$ or more droplets/ml of liquid, including $1\times10^{-8}$ or more droplets/ml of liquid, where in some instances the amount of droplets may be $1\times10^{-9}$ or more droplets/ml of liquid, $1\times10^{-10}$ or more droplets/ml of liquid, $1\times10^{-1}$ or more droplets/ml of liquid, or $1\times10^{-12}$ or more droplets/ml of liquid, where in some instances the amount of droplets is $1\times10^{-15}$ or less droplets/ml of liquid, such as $1\times10^{-13}$ or less droplets/ml of liquid, including $1\times10^{-12}$ or less droplets/ml of liquid.

In LCP droplets, the quantity of carbon equivalent molecules, e.g., as $HCO_3^-$, $CO_3^{2-}$, etc., may vary, and in some instances ranges from 1,000 carbon equivalent molecules to 1,000,000 carbon equivalent molecules per droplet. As such, carbon equivalent concentration may of a BRP may vary, and may readily be determined using the following formula:

$$(\text{\# carbon equivalent molecules/droplet})\times(\text{mol}/6.022\times 10^{23}\text{ molecules})\times(\text{\# droplets/mL})\times(1000\text{ mL/L})=\text{concentration}$$

In some instances, the carbon equivalent concentration is 10 nM or higher, such as 100 nM or higher, 500 nM or higher, 750 nM or higher, including 1 micromole or higher, 10 micromole or higher, 100 micromole or higher, 500 micromole or higher, 750 micromole or higher, including 1 millimole or higher, such as 10 millimole or higher, wherein in some instances the carbon equivalent concentration is 1 M or less, such as 750 millimole or less, including 500 millimole or less, such as 250 millimole or less, e.g., 100 millimole or less, 50 millimole or less, 10 millimole or less.

In biphasic compositions that include LCP droplets, the pH of the bulk solution may be higher than that of the LCPs, e.g., where the bulk fluid may have a pH in the range of pH 8.0 to pH 9.0, such as pH 8.2 to pH 8.5. Because of the higher concentration of carbon equivalent molecules in the LCP, the pH of the LCP droplets will be lower when compared to the pH of the bulk solution, e.g., where the pH of the fluid of the LCP droplets may range from 4.9 to pH 7.8, such as between pH 5.2 and pH 6.8. In these embodiments, the pH different is a result of the carbon equivalent molecules in the LCP pulling in extra protons, or acid, to balance the charge in the LCP. This phenomenon, in turn, allows for more $CO_2$ to be absorbed in the bulk solution, thus establishing a cycle that enables greater quantities of LCP in the BRP.

Figure 3:
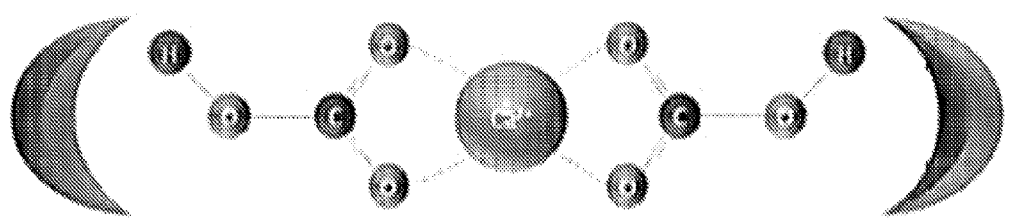
FIG. 3 provides a representation of a bidentate complex $Ca^{2+}$ and $HCO_3^-$ ions which may be present in LCP droplets of BRP compositions of the invention.

The bulk phase and LCP are characterized by having different $K_{eq}$, different viscosities, and different solubilities between phases. Bicarbonate, carbonate, and divalent ion constituents of the LCP droplets are those that, under appropriate conditions, may aggregate into a post-critical nucleus, leading to nucleation of a solid phase and continued growth. While the association of bicarbonate ions with divalent cations, e.g., $Ca^{2+}$, in the LCP droplets may vary, in some instances bidentate bicarbonate ion/divalent cation species may be present. For example, in LCPs of interest, $Ca^{2+}$/bicarbonate ion bidentate species may be present, as illustrated in FIG. 3.

While the diameter of the LCP droplets in the bulk phase of the BRLCP may vary, in some instances the droplets have a diameter ranging from 1 to 500 nm, such as 5 to 25 nm, and including 10 to 100 nm. In some instances, the droplets are charged, and may (in some instances) have a zeta potential ranging from −140 to 120, such as −100 to 40, and including −40 to −5. In some instances, the droplets are charged, where the droplets may be positively or negatively charged, as desired. The higher the magnitude of the charge (whether positive or negative) the more stable the LCP droplets may be. In some instances, the droplets of charge (positive or negative) with a magnitude ranging from 10 to 100, such as 15 to 75, including 20 to 50, e.g., 20 to 40. In the LCP droplets, the bicarbonate to carbonate ion ratio, (i.e., the $HCO_3^-/CO_3^{2-}$ ratio) may vary, and in some instances is 10 or greater to 1, such as 20 or greater to 1, including 25 or greater to 1, e.g., 50 or greater to 1. Additional aspects of LCPs of interest are found in Bewernitz et al., "A metastable liquid precursor phase of calcium carbonate and its interactions with polyaspartate," Faraday Discussions. 7 Jun. 2012. DOI: 10.1039/c2fd20080e (2012) 159: 291-312. The presence of LCPs may be determined using any convenient protocol, e.g., the protocols described in Faatz et al., Advanced Materials, 2004, 16, 996-1000; Wolf et al., Nanoscale, 2011, 3, 1158-1165; Rieger et al., Faraday Discussions, 2007, 136, 265-277; and Bewernitz et al., Faraday Discussions, 2012, 159, 291-312.

Where the bicarbonate rich product has two phases, e.g., as described above, the first phase may have a higher concentration of bicarbonate ion than a second phase, where the magnitude of the difference in bicarbonate ion concentration may vary, ranging in some instances from 0.1 to 4, such as 1 to 2. For example, in some embodiments, a bicarbonate rich product composition may include a first phase in which the bicarbonate ion concentration ranges from 1000 ppm to 5000 ppm, and a second phase where the bicarbonate ion concentration is higher, e.g., where the concentration ranges from 5000 ppm to 6000 ppm or greater, e.g., 7000 ppm or greater, 8000 ppm or greater, 9000 ppm or greater, 10,000 ppm or greater, 25,000 ppm or greater, 50,000 ppm or greater, 75,000 ppm or greater, 100,000 ppm, 500,000 or greater.

The BRP and products produced therefrom (as described in greater detail below) may include one or more components that are present in the aqueous media from which they are produced, where these one more components may identify the compositions that come from the aqueous medium. For example, if the aqueous medium is sea water, identifying compounds that may be present in BRP compositions (as well as products produced therefrom) include, but are not limited to: chloride, sodium, sulfur, potassium, bromide, silicon, strontium and the like. Any such source-identifying or "marker" elements are generally present in small amounts, e.g., in amounts of 20,000 ppm or less, such as amounts of 2000 ppm or less. In certain embodiments, the "marker" compound is strontium, which may be present in the precipitate incorporated into the aragonite lattice, and make up 10,000 ppm or less, ranging in certain embodiments from 3 to 10,000 ppm, such as from 5 to 5000 ppm, including 5 to 1000 ppm, e.g., 5 to 500 ppm, including 5 to 100 ppm. Another "marker" compound of interest is magnesium, which may be present in amounts of up to 20% mole substitution for calcium in carbonate compounds. The aqueous medium source identifier of the compositions may vary depending on the particular medium source, e.g., ocean water, lagoon water, brine, etc. In certain embodiments, the calcium carbonate content of the precipitate is 25% w/w or higher, such as 40% w/w or higher, and including 50% w/w or higher, e.g., 60% w/w. The carbonate compound composition has, in certain embodiments, a calcium/magnesium ratio that is influenced by, and therefore reflects, the water source from which it has been precipitated. In certain embodiments, the calcium/magnesium molar ratio ranges from 10/1 to 1/5 Ca/Mg, such as 5/1 to 1/3 Ca/Mg. In certain embodiments, the carbonate composition is characterized by having a water source identifying carbonate to hydroxide compound ratio, where in certain embodiments this ratio ranges from 100 to 1, such as 10 to 1 and including 1 to 1.

The BRP composition, as well as products (such as precipitated carbonates) produce therefrom, may have an isotopic profile that identifies the component as being of fossil fuel origin and therefore as being $CO_2$ sequestering. For example, in some embodiments the carbon atoms in the BRP reflect the relative carbon isotope composition ($\delta^{13}C$) of the fossil fuel (e.g., coal, oil, natural gas, tar sand) from which the industrial $CO_2$ that was used to make the BRP was derived. The relative carbon isotope composition ($\delta^{13}C$) value with units of ‰ (per mille) is a measure of the ratio of the concentration of two stable isotopes of carbon, namely $^{12}C$ and $^{13}C$, relative to a standard of fossilized belemnite (the PDB standard). The relative carbon isotope composition can be calculated using the following equation:

$$\delta^{13}C‰=[(^{13}C/^{12}C_{sample}-^{13}C/^{12}C_{PDB\ standard})/(^{13}C/^{12}C_{PDB\ standard})]\times 1000$$

As such, the $\delta^{13}C$ value of a BRP serves as a fingerprint for a $CO_2$ gas source, e.g., $CO_2$ released from burning a fossil fuel. The $\delta^{13}C$ value may vary from source to source (i.e., fossil fuel source) and in some instances the $\delta^{13}C$ value for the BRP may from between about −3‰ to about −45‰, wherein the more negative the $\delta^{13}C$ value, the more rich the BRP is in $^{12}C$. The ($\delta^{13}C$) value may vary from source to source (i.e., fossil fuel source), but the ($\delta^{13}C$) value for the BRP may, in some instances, range between −1‰ and −50‰ between −5‰ and −40‰, between −5‰ and −35‰, between −7‰ and −40‰, between −7‰ and −35‰, between −9‰ and −40‰, or between −9‰ and −35‰. In some embodiments, the ($\delta^{13}C$) value for the BRP is −3‰, −5‰, −6‰, −7‰, −8‰, −9‰, −10‰, −11‰, −12‰, −13‰, −14‰, −15‰, −16‰, −17‰, −18‰, −19‰, −20‰, −21‰, −22‰, −23‰, −24‰, −25‰, −26‰, −27‰, −28‰, −29‰, −30‰, −31‰, −32‰, −33‰, −34‰, −35‰, −36‰, −37‰, −38‰, −39‰, −40‰, −41‰, −42‰, −43, −44‰, or −45‰ or less (i.e., more negative), wherein the more negative the ($\delta^{13}C$) value, the more rich the BRP is in $^{12}C$. Any suitable method may be used for measuring the $\delta^{13}C$ value, such methods including, but not limited to, mass spectrometry or off-axis integrated-cavity output spectroscopy (off-axis ICOS).

In addition or alternatively to carbon isotope profiling, other isotopic profiles, such as those of oxygen ($\delta^{18}O$), nitrogen ($\delta^{15}N$), sulfur ($\delta^{34}S$), and other trace elements may also be used to identify a fossil fuel source that was used to produce an industrial $CO_2$ source from which a BRP is derived. For example, another marker of interest is ($\delta^{18}O$). Relative oxygen isotope composition ($\delta^{18}O$) value with units of ‰ (per mille) is a measure of the ratio of the concentration of two stable oxygen isotopes, namely $^{16}O$ and $^{18}O$, relative to a standard of Vienna Standard Mean Ocean Water (VSMOW or SMOW). The relative oxygen isotope composition can be calculated using the following equation:

$$\delta^{18}O = \left( \frac{\left(\frac{^{18}O}{^{16}O}\right)_{sample}}{\left(\frac{^{18}O}{^{16}O}\right)_{standard}} - 1 \right) * 1000\%$$

Sequestered $CO_2$ components produced as described herein may be derived from $CO_2$ of an industrial anthropogenic nature. When fossil fuels combust, the combustion-derived $CO_2$ range in ($\delta^{18}O$). There is a significant oxygen isotope fractionation in the uptake of atmospheric $O_2$ in the formation of $CO_2$ gas in the range of −20‰ to −25‰ ($\delta^{18}O$) from the oxygen isotopes in the fossil materials. While the biospheric $^{13}C$ signal mostly depends on the plant physiology, the activity and the environmental conditions during $CO_2$ uptake, and accordingly on the plant material consumed by combustion, $\delta^{18}O$ in $CO_2$ is closely connected to the water cycle. The global $\delta^{18}O$ background signal of $CO_2$ is set by atmosphere-ocean $CO_2$ exchange, and modified on land by the interaction with the vegetation. Because the $\delta^{18}O$ containing molecules are characterized by a lower evaporation rate than the light ones (without $\delta^{18}O$), they tend to remain in liquid water, rain out faster from clouds, and are thus reduced in aged clouds. Thereby a gradient is actively maintained that shows a depletion of the $\delta^{18}O$ isotope on a transect from the tropics to the poles, and also over the continents along the same latitude with increasing distance inland. Regional differences are induced since the oxygen signal of plant water and plant material is strongly related to the oxygen isotope ratio in rain and groundwater. Due to plant-physiological processes and fractionation coupled to transpiration, the plant leaf water is distinctly enriched in $\delta^{18}O$ compared to the source water. The modulation of the $CO_2$-$\delta^{18}O$ background signal takes place by exchange with the enriched oxygen of plant leaf water when $CO_2$ enters the stomata and leaves again without being assimilated. Isotope discrimination in plant metabolism occurs during biosynthesis of carbohydrates and other primary or secondary products; e.g., cellulose oxygen isotope ratios to be 27‰ (±3‰) higher relative to leaf water. Caused by further kinetic and equilibrium isotopic effects, the $\_\delta^{18}O$ value decreases for secondary products; total plant dry matter has a $\delta^{18}O$ value of about 18‰

Fossil fuels being derived from plant matter, whether recently harvested and dried plant matter, or organic matter from past periods such as coal, natural gas, petroleum, tar sands oil, propane or other fuels derived from hydrocarbons, will all be ($\delta^{18}O$) enriched due to plants having a preference during photosynthesis for slight fractionation on this isotope. During fuel use, the off-gas component of burning however is ($\delta^{18}O$) isotopically fractionated, and depleted relative to the fossil fuel due to the significant oxygen isotope fractionation in the uptake of atmospheric $O_2$ in the formation of $CO_2$ gas in the range of −20‰ to −25‰. When $CO_2$ gas interacts with water to form carbonic acid, bicarbonate ion, and carbonate ion, there is an exchange of the $CO_2$ oxygens with oxygens in the water, as well as the addition of oxygen from the water.

The isotopic composition of Vienna Standard Mean Ocean Water (VSMOW or SMOW) water is specified as ratios of the molar abundance of the rare isotope in question divided by that of its most common isotope and is expressed as parts per million (ppm). For instance $^{16}O$ (the most common isotope of oxygen with eight protons and eight neutrons) is roughly 2632 times more prevalent in sea water than is $^{17}O$ (with an additional neutron). The hydrogen and oxygen isotopic ratios of VSMOW water are defined as follows:
  $^{2}H/^{1}H=155.76\pm0.1$ ppm (a ratio of 1 part per approximately 6420 parts)
  $^{3}H/^{1}H=1.85\pm0.36\times10^{-11}$ ppm (a ratio of 1 part per approximately $5.41\times10^{16}$ parts, ignored for physical properties-related work)
  $^{18}O/^{16}O=2005.20\pm0.43$ ppm (a ratio of 1 part per approximately 498.7 parts)
  $^{17}O/^{16}O=379.9\pm1.6$ ppm (a ratio of 1 part per approximately 2632 part. These compounds will be present and measurable in the BRP component. Relative oxygen isotope composition ($\delta^{18}O$) value with units of ‰ (per mille) is a measure of the ratio of the concentration of two stable oxygen isotopes, namely ($\delta^{16}O$) and ($\delta^{18}O$), relative to a standard of Vienna Standard Mean Ocean Water (VSMOW or SMOW). The relative oxygen isotope composition can be calculated using the following equation:

$$\delta^{18}O = \left( \frac{\left(\frac{^{18}O}{^{16}O}\right)_{sample}}{\left(\frac{^{18}O}{^{16}O}\right)_{standard}} - 1 \right) * 1000\%$$

As such, the ($\delta^{18}O$) value of the BRP serves as a fingerprint for a $CO_2$ gas source, released from burning a fossil fuel for organic matter derived from photosynthetic means. The ($\delta^{18}O$) value may vary from source to source (i.e., fossil fuel source), and in some instances the ($\delta^{18}O$) value for a BRP ranges from between about −10‰ to about +10‰, wherein the more positive the $\delta^{18}O$ value, the more rich the BRP component is in $\delta^{18}O$. The ($\delta^{18}O$) value may vary from source to source (i.e., fossil fuel source), but the ($\delta^{18}O$) value for the bicarbonate of the BRP may, in some instances, range between −10‰ and +9‰ between −5‰ and +5‰, between −5‰ and +3‰, between −5‰ and 4‰, between −5‰ and 3‰, between −3‰ and +4‰, or between −2‰ and +3‰. In some embodiments, the ($\delta^{18}O$) value for the bicarbonate of the bicarbonate additive −12‰, −11‰, −10‰, −9‰, −8‰, −7‰, −6‰, −5‰, −4‰, −3‰, −2‰, −1‰, 0‰, 1‰, 2‰, 3‰, 4‰, 5‰, 6‰, 7‰, 8‰, 9‰, 10‰, 11‰, 12‰, 13‰, 14‰, 15‰, 16‰, 17‰, 18‰, 19‰, or 20‰, or more, wherein the more negative the ($\delta^{18}O$) value, the more depleted the bicarbonate component is in $\delta^{18}O$ due to the fractionation during combustion. Comparing atmospheric oxygen to that of sea water, atmospheric $O_2$ is almost 24‰ more enriched in $^{18}O$ than seawater, and this enrichment is known as the Dole effect. Therefore, when $CO_2$ gas interacts with water to form carbonic acid, bicarbonate ion, and carbonate, there is an exchange of the $CO_2$ oxygens with oxygens in the water, as well as the addition of oxygen from the water, and even with the exchange, since both the fractionation oxygen from combustion of fossil fuels and the Dole effect, the oxygen isotopic composition of the carbonic acid, bicarbonate ion, and carbonate that forms will never be enriched like the plant material the fossil fuel formed from or the natural waters that the $CO_2$ reacted with. Any suitable method may be used for measuring the $\delta^{18}O$ value, such methods including, but not limited to, mass spectrometry or off-axis integrated-cavity output spectroscopy (off-axis ICOS).

Deuterium (symbol D or $^2H$, also known as heavy hydrogen) is one of two stable isotopes of hydrogen. The nucleus of deuterium, called a deuteron, contains one proton and one neutron, whereas the far more common hydrogen isotope, protium, has no neutron in the nucleus. It has a natural abundance in Earth's oceans of about one atom in 6,420 of hydrogen. Thus deuterium accounts for approximately 0.0156% (or on a mass basis: 0.0312%) of all the naturally occurring hydrogen in the oceans, while the most common isotope (hydrogen-1 or protium) accounts for more than 99.98%. The abundance of deuterium changes slightly from one kind of natural water to another (see VSMOW).

A mass spectrometric method for the accurate determination of the hydrogen-deuterium ratio has been developed. It is possible to determine this ratio to ±0.10% using material of "normal abundance", i.e., 1 part D in 6700 parts H. Samples as small as 0.1 mg $H_2$ (0.001 ml $H_2O$) can be run. Natural evaporation and condensation that have been shown to fractionate the oxygen isotopes also fractionate the hydrogen isotopes. The ratio of these two fractionations is equal to the ratio between the ratios of the vapour pressures of $H_2O/H^DO$ and $H_2O^{16}/H_2O^{18}$.

Ocean waters range from 0.0153 to 0.0156 mole % deuterium, whereas fresh waters of the United States range from 0.0133 to 0.0154 mole % deuterium. This serves as a fingerprint for bicarbonate derived from the interaction of $CO_2$ with seawater compared to metoric fresh water. Brine waters, occupying the subsurface or arid lakes are often very saline and derive from ancient seawater that once occupied the continents and fill the sedimentary basins of Earth. Although the isotopic compositions of oxygen and hydrogen isotopes are know to vary with increasing salinity, the difference can be greater than anything seen with variations in salinity. Most carbonate minerals also contain small amounts of bicarbonate ion, and thus have the hydrogen for isotopic analysis for this fingerprint.

A number of trace elements are characteristic of subsurface brine waters that are derived from the ancient seawaters and interaction with the host rocks. These trace elements, along with those in the flue gases are incorporated in the bicarbonate formed from the interaction with flue gases and these waters, that give a fingerprint to the carbonate and bicarbonate compounds that form.

The formation of nitrous oxide, and other NOx compounds during the combustion of fossil fuels also depletes the 15N content due to fractionation and serves as a footprint. Sulfur dioxide also shows fractionation behavior that identifies the source of the sulfur from fossil fuel.

Process Conditions

As indicated above, the $CO_2$ containing gas is contacted with the aqueous medium under conditions sufficient to produce the desired BRP. The $CO_2$ containing gas may be contacted with the aqueous medium using any convenient protocol. For example, contact protocols of interest include, but are not limited to: direct contacting protocols, e.g., bubbling the gas through a volume of the aqueous medium, concurrent contacting protocols, i.e., contact between uni-directionally flowing gaseous and liquid phase streams, countercurrent protocols, i.e., contact between oppositely flowing gaseous and liquid phase streams, and the like. Contact may be accomplished through use of infusers, bubblers, fluidic Venturi reactors, spargers, gas filters, sprays, trays, or packed column reactors, and the like, as may be convenient.

Contact occurs under conditions such that a substantial portion of the $CO_2$ present in the $CO_2$ containing gas goes into solution to produce bicarbonate ions. By substantial portion is meant 10% or more, such as 50% or more, including 80% or more. In some instances, 5% or more, such as 10% or more, including 20% or more of all the bicarbonate ions in the initial expanded liquid phase solution (mother liquor) become sequestered in LCPs.

The temperature of the aqueous medium that is contacted with the gas may vary. In some instances, the temperature ranges from −1.4 to 100° C., such as 20 to 80° C. and including 40 to 70° C. In some instances, the temperature may range from −1.4 to 50° C. or higher, such as from −1.1 to 45° C. or higher. In some instances, cool water temperatures are employed, where such temperatures may range from −1.4 to 4° C., such as −1.1 to 0° C. While an initial aqueous media may be cooled to obtain the desired temperature, in some instances a natural source of the aqueous media having the desired optimal temperature may be employed. For example, where the aqueous medium is ocean or seawater, the ocean or sea water may be obtained from a location where the water has the desired temperature. In some instances, obtaining such water may include obtaining the water from a depth below the surface of the water (e.g., the surface of the ocean), where the depth may range in some instances from 10 to 2000 meters, such as 20 to 200 m.

In some instances, warmer temperatures are employed. For example, the temperature of the aqueous medium in some instances may be 25° C. or higher, such as 30° C. or higher, and may in some embodiments range from 25 to 50° C., such as 30 to 40° C. While a given aqueous medium may be warmed in such instances to arrive at these temperatures, in some instances the aqueous medium may be obtained from a naturally occurring source which is at the desired warm temperature, or obtained from a man-made source that provides the desired temperature, e.g., from the output of an industrial, e.g., power, plant cooling system, etc.

The $CO_2$ containing gas and aqueous medium are contacted at a pressure suitable for production of the desired bicarbonate rich product. In some instances, the pressure of the contact conditions is selected to provide for optimal $CO_2$ absorption, where such pressures may range from 1 atm to 100 atm, such as 1 atm to 10 atm. Where contact occurs at a location that is naturally at 1 atm, the pressure may be increased to the desired pressure using any convenient protocol. In some instances, contact occurs where the optimal pressure is present, e.g., at a location under the surface of a body of water, such as an ocean or sea. In some instances, contact of the $CO_2$ containing gas and bicarbonate buffered aqueous medium occurs a depth below the surface of the water (e.g., the surface of the ocean), where the depth may range in some instances from 10 to 1000 meters, such as 10 to 100 meters. Conveniently, in such instances the water used to produce the bicarbonate rich product (and in some instances LCP) may be obtained at the same depth as the depth at which combination occurs. Following contact, the product (which may include LCP) may be brought back up to the surface for further processing, as desired. Alternatively, the product may be released into the environment, e.g., deep water, where it was produced, where it may be stable for extended periods of time. Where the product is released into the environment, it may be allowed to fall further in depth, e.g., to the ocean floor.

LCP Promoter

In some instances, the $CO_2$ containing gas and aqueous medium are contacted in the presence of an LCP promoter.

LCP promoters include entities that function by stabilizing the formation of the LCP in the BRP composition. LCP promoters of interest include LCP promoting cations, which cations may be present with suitable counter-anions. Examples of LCP promoting cations include, but are not limited to, divalent alkaline earth metal cations, such as, e.g., $Ca^{2+}$, $Mg^{2+}$ and combinations thereof. Additional divalent cations of interest that may be employed, either alone or in combination, as an LCP promoter include, but are not limited to: $Be^{2+}$, $Ba^{2+}$, $Sr^{2+}$, $Pb^{2+}$, $Fe^{2+}$, $Hg^{2+}$, and the like. Other cations of interest that may or may not be divalent include, but are not limited to: $Na^+$, $K^+$, $NH_4^+$, and Li+, as well as cationic species of Mn, Ni, Cu, Zn, Ce, La, Al, Y, Nd, Zr, Gd, Dy, Ti, Th, U, La, Sm, Pr, Co, Cr, Te, Bi, Ge, Ta, As, Nb, W, Mo, V, etc.

The counter-anion of the LCP promoter may be any convenient anion. Anions of interest include, but are not limited to: $Cl^-$, $SO_4^{2-}$, $NO_3^-$, $BO_4^-$, silicate, phosphate and the like.

The amount of LCP promoter that is provided may vary, as desired. In some instances, the amount of LCP promoter present upon combination with the aqueous phase and the $CO_2$ source ranges from 1 to 80%, such as 5 to 10% and the including 6.9 to 8.6% dry wt.

In some instances, the aqueous phase employed in the methods is one that already includes a suitable LCP promoter. For example, naturally-occurring aqueous media which include a cation source, divalent or otherwise, and therefore may be employed in embodiments of the subject BRP production systems include, but are not limited to: aqueous media obtained from seas, oceans, estuaries, lagoons, brines, alkaline lakes, inland seas, etc., such as described above.

Catalyst

Where desired, the $CO_2$ containing gas is contacted with the bicarbonate buffered aqueous medium in the presence of a catalyst (i.e., an absorption catalyst) that mediates the conversion of $CO_2$ to bicarbonate. Of interest as absorption catalysts are catalysts that, at pH levels ranging from 8 to 10, increase the rate of production of bicarbonate ions from dissolved $CO_2$. The magnitude of the rate increase (e.g., as compared to control in which the catalyst is not present) may vary, and in some instances is 2-fold or greater, such as 5-fold or greater, e.g., 10-fold or greater, as compared to a suitable control. In some instances, the catalyst is a carbon dioxide-specific catalyst. Examples of carbon dioxide-specific catalysts of interest include enzymes, such as carbonic anhydrases, synthetic catalysts, such as those transition metal catalysts described in Koziol et al., "Toward a Small Molecule, Biomimetic Carbonic Anhydrase Model: Theoretical and Experimental Investigations of a Panel of Zinc (II) Aza-Macrocyclic Catalysts," Inorganic Chemistry (2012) 51: 6803-6812, colloidal metal particles, such as those described in Bhaduri and Siller, "Nickel nanoparticles catalyse reversible hydration of carbon dioxide for mineralization carbon capture and storage," Catalysis Science & Technology (2013) DOI: 10.1039/c3cy20791a, and the like, e.g., colloidal metal oxide particles.

Carbonic anhydrases of interest include both naturally occurring (i.e., wild-type) carbonic anhydrase, as well as mutants thereof. Specific carbonic anhydrases of interest include, but are not limited to: α-CAs, which include mammalian carbonic anhydrases, e.g., the cytosolic CAs (CA-I, CA-II, CA-III, CA-VII and CA XIII) (CA1, CA2, CA3, CA7, CA13), mitochondrial CAs (CA-VA and CA-VB) (CA5A, CA5B), secreted CAs (CA-VI) (CA6), and membrane-associated CAs (CA-IV, CA-IX, CA-XII, CA-XIV and CA-XV) (CA4, CA9, CA12, CA14); β-CAs, which include prokaryotic and plant chloroplast CAs; γ-CAs, e.g., such as found in methane-producing bacteria; and the like. Carbonic anhydrases of interest further include those described in U.S. Pat. No. 7,132,090, the disclosure of which is herein incorporated by reference. Carbonic anhydrases of interest include those having a specific activity of $10^3$ s$^{-1}$ or more, such as $10^4$ s$^{-1}$ to or more, including $10^5$ s$^{-1}$ or more. When employed, the catalyst is present in amount effective to provide for the desired rate increase of bicarbonate production, e.g., as described above. In some instances where the catalyst is an enzyme, the activity of the enzyme in the aqueous media may range from $10^3$ to $10^6$ s$^{-1}$, such as $10^3$ to $10^4$ s$^{-1}$ and including $10^5$ to $10^6$ s$^{-1}$. When employed, a catalyst, e.g., enzyme such as a carbonic anhydrase, can be made available in the reaction using any convenient approach, such as through a solid support (such as a permeable membrane) to which the catalyst is attached or otherwise with which the catalyst is stably associated, through porous media and the like having the catalyst stably associated therewith, large surfaces with the catalyst immobilized therein (i.e., attached thereto), or with the catalyst in solution, e.g., which may be recovered following use. Examples of catalyst formats that may be employed include, but are not limited to, those described in U.S. Pat. No. 7,132,090; the disclosure of which is herein incorporated by reference.

Synthetic catalysts of interest include synthetically prepared transition metal containing complexes, prepared as biomimetic models of carbonic anhydrase enzymes, e.g., as described above. Specific synthetic catalysts include, but are not limited to: transition metal aza-macrocyclic catalysts, e.g., the zinc(II) aza-macrocyclic catalysts having macrocyclic rings of 9, 12, 13, or 14, as described in Koziol et al., "Toward a Small Molecule, Biomimetic Carbonic Anhydrase Model: Theoretical and Experimental Investigations of a Panel of zinc(II) Aza-Macrocyclic Catalysts," Inorganic Chemistry (2012) 51: 6803-6812, imidazole- and indole-based metal catalysts, e.g., the zinc(II) catalysts described in United States Published Application No. US20110293496, United States Published Application No. US20120199535 and United States Published Application No. US20110151537, aminopyridyl-based catalysts, e.g., as described in Feng et al., "A Highly Reactive Mononuclear Zn(II) Complex for Phosphodiester Cleavage," Journal of the American Chemical Society (2005) 127: 13470-13471, pyrazolylhydroborato- and pyridylthiomethyl-based compounds, e.g., as described in Sattler and Parkin, "Structural characterization of zinc bicarbonate compounds relevant to the mechanism of action of carbonic anhydrase," Chemical Science (2012) 3: 2105-2109. Synthetic catalysts of interest include those having a specific activity of $10^2$ s$^{-1}$ or more, such as $10^3$ s$^{-1}$ or more, including $10^4$ s$^{-1}$ or more. When employed, the synthetic catalyst is present in amount effective to provide for the desired rate increase of bicarbonate production, e.g., as described above for carbonic anhydrase. When employed, a synthetic catalyst, e.g., aza-macrocyclic transition metal catalyst, can be made available in the reaction using any convenient approach, e.g., as described above for carbonic anhydrase.

Metal nanoparticles of interest include commercially available as well as synthetically prepared colloidal particles of transition metals. Specific colloidal metal particles include, but are not limited to: metal nanoparticles, e.g., the nickel nanoparticles (NiNPs) described in Bhaduri and Siller, "Nickel nanoparticles catalyse reversible hydration of carbon dioxide for mineralization carbon capture and storage," Catalysis Science & Technology (2013) DOI: 10.1039/c3cy20791a. Colloidal metal particles of interest include those having a specific activity of $10^2$ s$^{-1}$ or more, such as $10^3$ s$^{-1}$ or more, including $10^4$ s$^{-1}$ or more. When employed, the colloidal metal particles are present in amount effective to provide for the desired rate increase of bicarbonate production, e.g., as described above for carbonic anhydrase. When employed, the colloidal metal particles, e.g., transition metal nanoparticles, can be made available in the reaction using any convenient approach, e.g., as described above for carbonic anhydrase. Metal nanoparticle catalysts finding use in embodiments described herein are further described in U.S. Provisional Application Ser. No. 61/793,585 filed on Mar. 15, 2013; the disclosure of which is herein incorporated by reference.

In one embodiment, some portion of the bicarbonate not separated in the LCP may be consumed to regenerate carbonate to begin the absorption process again. For example, the aqueous medium may include an alkali metal cation, such as sodium cation. Where sodium cation is present, the aqueous medium may be a sodium carbonate solution. In such instances, for each $CO_2$ absorbed, there is one carbonate making two bicarbonates. One of the two bicarbonates is used to go on to separate out as a condensed liquid phase, and the other is used to regenerate sodium carbonate by forming $CO_2$ and sodium carbonate with carbonic anhydrase, synthetic catalyst or colloidal metal particles.

In some instances, amines, including primary, secondary and tertiary amines, may be provided as enhancers of $CO_2$ solvation and/or catalysts in bicarbonate ion formation. Primary amines of interest include, but are not limited to: ammonia, 2-amino-2-hydroxymethyl-propane-1,3-diol (TRIS), monoethanolamine (MEA), 2-amino-2-methyl-1-propanol (AMP), melamine, amino-2-propanol, arginine, poly-arginine, etc. Secondary amines of interest include, but are not limited to: diethanolamine (DEA), morpholine, 2-(tert-butylamino)ethanol (TBAE), bis(2-hydroxypropyl)amine, piperazine, aminoethylethanolamine, N-[Tris(hydroxymethyl)methyl]-3-aminopropanesulfonic acid (TAPS), etc. Tertiary amines of interest include, but are not limited to: 2,2',2'',2'''-(ethylenedinitrilo)tetraethanol (TH-EED), methyldiethanolamine (MDEA), poly-melamine-formaldehyde (Tysol SM), triethanolamine (TEOA), triethanolamine acetate, tris(2-hydroxypropyl)amine, etc. When present, the amount of these amines may vary, and in some instances ranges from 1% to 80%, such as 10.2% to 21.7% dry wt.

LCP Stabilizing System

In some instances, the $CO_2$ containing gas and aqueous medium may be contacted in the presence of an LCP stabilizing system, which stabilizing system may be made up of one or more components. Where the LCP composition is a two-phase system, e.g., as described above, it may be viewed as a micro-emulsion, e.g., a kinetic or thermodynamic stabilized dispersion of two immiscible liquids which are stabilized by interfacial amphiphilic or amphipathic molecules. In such embodiments, any convenient micro-emulsion stabilization system may be employed. Systems of interest include, but are not limited to, those that effect the volume stabilization and/or the surface area (S.A) destabilization of the emulsion droplet in the micro-emulsion. Emulsion surface properties and bulk solution properties can be manipulated to either inhibit or promote overall BRLCP formation and/or stability, as desired.

In some instances, the stabilizing system is a system that promotes emulsion volume stabilization. Where the driving force for LCP formation is the association of chaotropic waters of hydration, the addition of chaotropic (i.e., water structure breaking) additives to the solution may be employed to promote smaller, more numerous droplets as the S.A.: volume ratio will be reduced at equilibrium and therefore lead to more LCP formation. Some relevant additives which partition into the chaotropic phase and may be employed as stabilizers of the volume of the phase include, but are not limited to: Cl$^-$, Br$^-$, I$^-$, K$^+$, ammonia, ammonium, nitrates, nitrites, molecules and polymers with nitrogen-based functional groups and very small hydrophobic species. Also of interest are kosmotropic (water structure forming) solute additives, where examples of such additives include, but are not limited to: Mg$^{2+}$ and Li$^{3+}$. When present, the amount of such additives may vary, and in some instances ranges from 1% to 80%, including 5.2% to 24.4% dry wt.

In some instances, the stabilizing system is a system that promotes emulsion surface area (S.A.) stabilization. The amphipathic species that align at the interface between chaotropic and kosmotropic phases may influence the size distribution and overall amount of the LCP phase. The presence of strong amphipathic species, e.g., surfactants, may be employed to minimize the S.A. destabilization and lead to smaller, more numerous droplets. When present, the amount of such additives may vary, and in some instances ranges from 1 to 80%, including 2.6 to 6.9% dry wt.

Such stabilizers include, but are not limited to: amino acids (e.g., glutamate, aspartate, arginine, lysine, and histidine), polycarboxylic acids, Si, melamine sulfonate polycondensation product, naphthaline sulfonate polycondensation product, naphthaline polycondensation product, etc., and charged polymeric materials, including polyelectrolytes, (e.g., polyanions and polycations), polypeptides, and peptoids.

Polyelectrolytes of interest may vary greatly, and in some instances have a molecular weight of 900 daltons or greater, such as 1,000 daltons or greater, including 1,500 daltons or greater, ranging in some instances from 900 to 500,000 daltons, such as 1,000 to 50,000 daltons. Polyelectrolytes of interest may include organic and/or inorganic components, and may include monomeric residues that are singly or doubly charged under certain pH conditions, such as, e.g., a negatively charged (anionic) unit at a pH ranging from 6 to 8. Anionic functionalities include, but are not limited to: phosphates, phosphonates, sulfates, sulfonates, carboxylates, polyphosphates and polycarboxylates. Various anionic monomer residues may include phosphate, acrylate, maleate, methacrylate, vinyl carboxymethyl ether, or the like. The monomers may be homopolymerized or copolymerized, the organic monomers, where desired, being copolymerized with a wide variety of hydrocarbon or heterosubstituted ethylenic monomers. The neutral monomers may be from two to six, such as two to four carbon atoms, having from one to three, such as from one to two heteroatoms which may be oxygen, e.g., oxy and oxo, carbonyl oxo and carboxyl non-oxo-carbonyl, etc. Illustrative neutral monomers suitable for copolymerization include methyl acrylate, methyl vinyl ether, hydroxyethyl acrylate, ethylene, vinyl acetate, etc. Inorganic polyelectrolytes of interest include, but are not limited to: polyphosphates, such as polyphosphates having nine or more phosphate groups, such as twelve or more phosphate groups and in some instances 100 or less phosphate groups, such as polyphosphates having from 20 to 30 phosphate groups.

Such agents further include peptidic agents, such as peptides, polypeptides and proteins, as well as peptidomimetics, e.g., peptoids, β-peptides, etc. Peptidic agents of interest may vary in mass, ranging in some instances from 125 to 500,000 daltons, such as 1,000 to 100,000 daltons and including 10,000 to 50,000 daltons. Examples of polypeptides of interest include, but are not limited to: polyaspartates, polyglutamates, polylysines, polyasparagines, or polyhistidines, as well as heteropolymers of charges and uncharged amino acid residues. Amino acid residues may be L or D amino acids, and may be naturally or non-naturally occurring. Such agents further include polysaccharide agents, such as starches, pectins, celluloses, chitins, and acidic polysaccharides. Polysaccharide agents of interest may vary in mass, ranging in some instances from 125 to 500,000 daltons, such as 1,000 to 100,000 daltons and including 10,000 to 50,000 daltons.

Silica Source

Where desired, the $CO_2$ containing gas is contacted with the aqueous medium in the presence of a source of silica (and optionally a silica specific catalyst). The source of silica may be pure silica or a composition that includes silica in combination with other compounds, e.g., minerals, so long as the source of silica is sufficient to impart desired alkalinity during $CO_2$ hydration, e.g., via autocatalytic silica compensation. In some instances, the source of silica is a naturally occurring source of silica. Naturally occurring sources of silica include silica containing rocks, which may be in the form of sands or larger rocks. Where the source is larger rocks, in some instances the rocks have been broken down to reduce their size and increase their surface area. Of interest are silica sources made up of components having a longest dimension ranging from 0.01 mm to 1 meter, such as 0.1 mm to 500 cm, including 1 mm to 100 cm, e.g., 1 mm to 50 cm. The silica sources may be surface treated, where desired, to increase the surface area of the sources.

A variety of different naturally occurring silica sources may be employed. Naturally occurring silica sources of interest include, but are not limited to, igneous rocks, which rocks include: ultramafic rocks, such as Komatiite, Picrite basalt, Kimberlite, Lamproite, Peridotite; mafic rocks, such as Basalt, Diabase (Dolerite) and Gabbro; intermediate rocks, such as Andesite and Diorite; intermediate felsic rocks, such as Dacite and Granodiorite; and Felsic rocks, such as Rhyolite, Aplite—Pegmatite and Granite.

Also of interest are man-made sources of silica. Man-made sources of silica include, but are not limited to, waste streams such as: mining wastes; fossil fuel burning ash; slag, e.g. iron slag, phosphorous slag; cement kiln waste; oil refinery/petrochemical refinery waste, e.g. oil field and methane seam brines; coal seam wastes, e.g. gas production brines and coal seam brine; paper processing waste; water softening, e.g. ion exchange waste brine; silicon processing wastes; agricultural waste; metal finishing waste; high pH textile waste; and caustic sludge. Mining wastes include any wastes from the extraction of metal or another precious or useful mineral from the earth. Wastes of interest include wastes from mining to be used to raise pH, including: red mud from the Bayer aluminum extraction process; the waste from magnesium extraction for sea water, e.g. at Moss Landing, Calif.; and the wastes from other mining processes involving leaching. Ash from processes burning fossil fuels, such as coal fired power plants, create ash that is often rich in silica. In some embodiments, ashes resulting from burning fossil fuels, e.g. coal fired power plants, are provided as silica sources, including fly ash, e.g., ash that exits out the smoke stack, and bottom ash.

The amount of silica source that is present during contact of the $CO_2$ containing gas and bicarbonate buffered aqueous medium may vary, so long as it is sufficient to provide for the desired alkalinity during $CO_2$ hydration, e.g., via autocatalytic silica compensation. The amount employed will depend on the particular silica source, as well as the volume of the reactor, the nature of the bicarbonate buffered aqueous medium, the nature of the $CO_2$ containing gas, etc. Where the $CO_2$ containing gas is contacted with the bicarbonate buffered aqueous medium in a reactor, the volume percent of the reactor occupied by the silica source may range, in some instances, from 1 to 99%, such as 5 to 95% and including 10 to 90%. In some instances, the silica source is not dissolved with a strong acid, such as HCl.

Where desired, a silica specific catalyst may be provided which enhances the rate of dissolution of the silica source. The magnitude of the rate increase (e.g., as compared to control in which the catalyst is not present) may vary, and in some instances is 2-fold or greater, such as 5-fold or greater, e.g., 10-fold or greater, as compared to a suitable control. Catalysts of interest include those having a specific activity of $10^2$ $s^{-1}$ or more, such as $10^3$ $s^{-1}$ or more, including $10^4$ $s^{-1}$ or more. Catalysts of interest include both enzymatic and non-enzymatic catalysts, like those silicateins described in U.S. Pat. No. 7,229,807 e.g., but not limited to those described in Zhou et al., "Efficient Catalysis of Polysiloxane Synthesis by Silicatein α Requires Specific Hydroxy and Imidazole Functionalities," Angewante Chemie International Edition (1999) 38: 779-782 and in Roth et al., "Bifunctional Small Molecules Are Biomimetic Catalysts for Silica Synthesis at Neutral pH," Journal of the American Chemical Society (2005) 127: 325-330. Enzymatic catalysts of interest include, but are not limited to: silicateins, silicases, and the like. Non-enzymatic catalysts of interest include, but are not limited to: cyclens, and the like.

Additional details regarding silica sources and their use are described in U.S. Provisional Application Ser. No. 61/793,731 filed on Mar. 15, 2013; the disclosure of which is herein incorporated by reference.

Bicarbonate Rich Product

The above methods result in the production of a bicarbonate rich product (BRP). As reviewed above, BRP compositions are compositions that are characterized by high concentrations of bicarbonate ion, where the concentration of bicarbonate ion may, in some instances, be 5,000 ppm or greater, such as 10,000 ppm or greater, including 15,000 ppm or greater may be achieved. In some instances, the bicarbonate ion may range from 5,000 to 20,000 ppm, such as 7,500 to 15,000 ppm, including 8,000 to 12,000 ppm. In some instances, the overall amount of bicarbonate ion in the BRLCP may range from 0.1 wt. % to 30 wt. %, such as 3 to 20 wt. %, including from 10 to 15 wt. %. In some instances, the BRP includes droplets of a liquid condensed phase (LCP) in a bulk liquid, e.g., bulk solution, as reviewed above. Following preparation of the BRP composition, the BRP composition may be stored or further manipulated as desired.

BRP Storage

In some embodiments, the BRP composition may be stored for an extended period of time, if not indefinitely, thereby sequestering $CO_2$ obtained from the initial $CO_2$ source used to produce the BRP composition. For example, in cold climates the BRP composition may be allowed to freeze until weather conditions allow the product to thaw, at which time further manipulation of the product (e.g., as described below) may be performed. Product BRP compositions may be stored in geologic reservoirs until needed, or even allowed to mix with geologic brine solutions and allowed to mineralize in situ. As such, following the production of a BRP composition, further manipulation (if it occurs at all), may be delayed for a period of time, such as 1 day or longer, 1 week or longer, 1 month or longer, 3 months or longer, 6 months or longer, 1 year or longer, etc. In instances where storage of the BRP composition or component thereof (e.g., LCP) is desired, the product may be stored in a sealed container, e.g., a drum or larger container, and may or may not be stored in an environment that includes an atmosphere which prevents off-gassing, e.g., a pure $CO_2$ atmosphere, etc.

In some instances where the BRP includes droplets of LCP, the BRP product composition may be subjected to a separation protocol, e.g., where LCPs of the bicarbonate rich product are separated from bulk solution, e.g., for further manipulation (e.g., for storage, production of carbonate mineral, etc.) Any convenient separation protocol may be employed, where protocols of interest include, but are not limited to: hydrocyclones, decanter centrifuges, ultra-centrifugation, Epurimat, sledge bed clarifyers, and the like.

In certain embodiments, it is desirable to form a bicarbonate solid, for a variety of uses, e.g., production of sodium bicarbonate, (baking soda).

BRP Additive/Admixtures

Where desired, the BRP product compositions may be employed in various applications, either as made or upon addition of further components, e.g., a chemical admixture component. For example, a BRP composition may be employed as a cement additive (e.g., as a setting fluid or in conjunction with another setting liquid), either as produced or upon combination with other components, as desired.

In some instances, the product BRP compositions are employed as bicarbonate additives for cements. The term "bicarbonate additive" as used herein means any composition, which may be liquid or solid, that includes bicarbonate ($HCO_3^-$) ions, or a solid derivative thereof (e.g., as described in greater detail below). Where the bicarbonate additive is a liquid composition, the liquid composition may be employed as the sole setting liquid component in production of the settable cementitious composition, or it may be employed in conjunction with one or more additional setting liquids, e.g., as described in greater detail below. The pH of a liquid bicarbonate additive may vary, and in certain instances ranges from 4 to 12, such as 5 to 9, e.g., 6 to 8. The amount of bicarbonate ions in the bicarbonate additive may vary, as desired. For liquid compositions, the overall amount of bicarbonate may range in some instances from 0.1 wt. % to 30 wt. %, such as 3 to 20 wt. %, including from 10 to 15 wt. %.

As mentioned above, the bicarbonate additive employed to produce a given settable cementitious composition may be a liquid or solid. When present as a solid, the solid is a dehydrated version of a liquid bicarbonate additive. The solid may be one that is produced from a liquid bicarbonate additive using any convenient protocol for removed water from the liquid, e.g., evaporation, freeze drying, etc. Upon combination with a suitable volume of water, the resultant solid dissolves in the water to produce a liquid bicarbonate additive, e.g., as described above. In some instances, reconstitution is achieved by combining the dry bicarbonate additive with a sufficient amount of liquid, e.g., aqueous medium, such as water, where the liquids to solids ratio employed may vary, and in some instances ranges from 1,000,000 to 1, such as 100,000 to 10. Solid bicarbonate additives may include a variety of different particle sizes and particle size distributions. For example, in some embodiments a solid bicarbonate additive may include particulates having a size ranging from 1 to 10,000 µm, such as 10 to 1,000 µm and including 50 to 500 µm.

Further details regarding BRP bicarbonate additives are provided in U.S. Provisional Application Ser. No. 61/807,230 filed on Apr. 1, 2013 and U.S. Provisional Application Ser. No. 61/819,427 filed on May 3, 2013; the disclosures of which are herein incorporated by reference.

In some instances, the BRP composition may be combined with one or more additional chemical admixtures to produce a BRP admixture. In such admixture compositions, the total amount of BRP component may vary. In some instances, the BRP component is present in an amount ranging from 0.1 to 25, such as 1 to 15, including 5 to 10 wt %. In some instances, an admixture contains an amount of $CO_2$ present in solution, e.g., the form of a bicarbonate, BRP, etc., which is greater than the amount that would be predicted to be in the solution based on the alkalinity of the solution, where in some instances the actual amount exceeds the predicted amount by a factor of 1.1 or more, such as 1.25 or more, including 1.5 or more, e.g., 2 or more, 5 or more, 10 or more, including 25 or more.

Chemical admixture components are made up of one or more chemicals that are added to cements to impart desirable characteristics or properties to the cement, e.g., to modify properties of the cement to make it more readily useable or more suitable for a particular purpose. When used with concretes, chemical admixtures are materials in the form of powder or fluids that are added to the concrete to give it certain characteristics not obtainable with plain concrete mixes. The amount of a chemical admixture that is included in a given cement/concrete mixture may vary depending on the nature of the chemical admixture composition. In certain embodiments, the amount of a chemical admixture composition that is included in the cement/concrete mixture may range from 1% to about 50% (w/w), where in some instances the amount of 25% or less, such as 20% or less, e.g., 15% or less, including 10% or less, e.g., 5% or less, such as 2.5% or less.

Chemical admixtures of interest include, but are not limited to: plasticizers (e.g., compounds that can be added to a settable cementitious composition to provide it with improved workability for ease of placement with reduced consolidating effort and in reinforced settable cementitious compositions that are required to flow uniformly without leaving void space under reinforcing bars); accelerators, retarders, air-entrainers, foaming agents, water reducers, corrosion inhibitors, and pigments or coloring agents.

Accelerators are used to increase the cure rate (i.e., the hydration) of the settable cementitious composition and are of particular importance in applications where it is desirable for the settable cementitious composition to harden quickly, and in low temperature applications. Retarders act to slow the rate of hydration and increase the time available to pour the settable cementitious composition and to form it into a desired shape. Retarders are of particular importance in applications where the settable cementitious composition is being used in hot climates. Air-entrainers are used to distribute tiny air bubbles throughout the settable cementitious composition. Air-entrainers are of particular value for utilization in regions that experience cold weather because the tiny entrained air bubbles help to allow for some contraction and expansion to protect the settable cementitious composition from freeze-thaw damage. Pigments and coloring agents can also be added to concrete to provide it with desired color characteristics for aesthetic purposes. As such, admixtures of interest include, but are not limited to: set accelerators, set retarders, air-entraining agents, de-foamers, alkali-reactivity reducers, bonding admixtures, dispersants, coloring admixtures, corrosion inhibitors, damp-proofing admixtures, gas formers, permeability reducers, pumping aids, shrinkage compensation admixtures, fungicidal admixtures, germicidal admixtures, insecticidal admixtures, rheology modifying agents, wetting agents, strength enhancing agents, water repellents, etc.

Set accelerators are used to accelerate the setting and early strength development of a settable cementitious composition. A set accelerator that can be used as an admixture can be, but is not limited to, a nitrate salt of an alkali metal, alkaline earth metal, or aluminum; a nitrite salt of an alkali metal, alkaline earth metal, or aluminum; a thiocyanate of an alkali metal, alkaline earth metal or aluminum; an alkanolamine; a thiosulfate of an alkali metal, alkaline earth metal, or aluminum; a hydroxide of an alkali metal, alkaline earth metal, or aluminum; a carboxylic acid salt of an alkali metal, alkaline earth metal, or aluminum (e.g., calcium formate); a polyhydroxylalkylamine; a halide salt of an alkali metal or alkaline earth metal (e.g., chloride).

Set retarding admixtures may also be used. Set retarding, also known as delayed-setting or hydration control, admixtures are used to retard, delay, or slow the rate of setting of a settable cementitious composition. They can be added to the settable cementitious composition upon initial batching or at some time after the hydration process has begun. Set retarders are used to offset the accelerating effect of hot weather on the setting of a settable cementitious composition, or delay the initial set of a settable cementitious composition when, e.g., difficult conditions of placement occur, problems of delivery to the job site occur, or to allow time for special finishing processes. Most set retarders also act as low-level water reducers, and can also be used to entrain some air into a settable cementitious composition. Retarders that can be used include, but are not limited to oxy-boron compounds, corn syrup, lignin, a polyphosphonic acid, a carboxylic acid, a hydroxycarboxylic acid, polycarboxylic acid, hydroxylated carboxylic acid, such as fumaric, itaconic, malonic, borax, gluconic, and tartaric acid, lignosulfonates, ascorbic acid, isoascorbic acid, sulphonic acid-acrylic acid copolymer, and their corresponding salts, polyhydroxysilane, polyacrylamide, carbohydrates and mixtures thereof.

Also of interest as admixtures are air entrainers. The term air entrainer includes any substance that will entrain air in cementitious compositions. Some air entrainers can also reduce the surface tension of a composition at low concentration. Air-entraining admixtures are used to purposely entrain microscopic air bubbles into a settable cementitious composition. Air-entrainment dramatically improves the durability of settable cementitious compositions exposed to moisture during cycles of freezing and thawing. In addition, entrained air greatly improves resistance to surface scaling caused by chemical de-icers. Air entrainment also increases the workability of fresh settable cementitious compositions while eliminating or reducing segregation and bleeding. Materials used to achieve these desired effects can be selected from wood resin, natural resin, synthetic resin, sulfonated lignin, petroleum acids, proteinaceous material, fatty acids, resinous acids, alkylbenzene sulfonates, sulfonated hydrocarbons, vinsol resin, anionic surfactants, cationic surfactants, nonionic surfactants, natural rosin, synthetic rosin, inorganic air entrainers, synthetic detergents, and their corresponding salts, and mixtures thereof. Air entrainers are added in an amount to yield a desired level of air in a cementitious composition.

Also of interest as admixtures are de-foamers. De-foamers are used to decrease the air content in a cementitious composition. Examples of de-foamers that can be utilized in the cementitious composition include, but are not limited to mineral oils, vegetable oils, fatty acids, fatty acid esters, hydroxyl functional compounds, amides, phosphoric esters, metal soaps, silicones, polymers containing propylene oxide moieties, hydrocarbons, alkoxylated hydrocarbons, alkoxylated polyalkylene oxides, tributyl phosphates, dibutyl phthalates, octyl alcohols, water-insoluble esters of carbonic and boric acid, acetylenic diols, ethylene oxide-propylene oxide block copolymers and silicones.

Also of interest as admixtures are corrosion inhibitors. Corrosion inhibitors in settable cementitious compositions serve to protect embedded reinforcing materials (e.g., embedded steel) from corrosion. The high alkaline nature of most settable cementitious compositions causes a passive and non-corroding protective oxide film to form on materials such as steel. However, carbonation or the presence of chloride ions from de-icers or seawater can destroy or penetrate the film and result in corrosion. Corrosion-inhibiting admixtures chemically arrest this corrosion reaction. The materials most commonly used to inhibit corrosion are calcium nitrite, sodium nitrite, sodium benzoate, certain phosphates or fluorosilicates, fluoroaluminites, amines and related chemicals.

Also of interest are damp-proofing admixtures. Damp-proofing admixtures reduce the permeability of settable cementitious compositions that have low cement contents, high water-cement ratios, or an aggregate deficiency. These admixtures retard moisture penetration into set cementitious compositions and include certain soaps, stearates, and petroleum products.

Also of interest are gas-forming admixtures. Gas formers, or gas-forming agents, are sometimes added to settable cementitious compositions in very small quantities to cause a slight expansion prior to hardening. The amount of expansion is dependent upon the amount of gas-forming material used and the temperature of the fresh mixture. Aluminum powder, resin soap and vegetable or animal glue, saponin or hydrolyzed protein can be used as gas formers.

Also of interest are permeability reducers. Permeability reducers are used to reduce the rate at which water under pressure is transmitted through cementitious compositions. Silica fume, fly ash, ground slag, natural pozzolans, water reducers, and latex can be employed to decrease the permeability of the cementitious composition.

Also of interest are rheology-modifying agent admixtures. Rheology-modifying agents can be used to increase the viscosity of cementitious compositions. Suitable examples of rheology modifiers include fumed silica, colloidal silica, hydroxyethyl cellulose, hydroxypropyl cellulose, fly ash, mineral oils, hectorite clay, polyoxyalkylenes, polysaccharides, natural gums, or mixtures thereof.

Bacterial and fungal growth on or in hardened concrete may be partially controlled through the use of fungicidal and germicidal admixtures. Examples of these materials include polyhalogenated phenols, dialdrin emulsions, and copper compounds.

The BRP admixtures may be prepared using any convenient protocol. For example, a chemical admixture may be combined with a BRP to produce the BRP admixture. The ratio of BRP to chemical admixture may vary, and in some instances ranges from 1 to 10, such as from 1 to 1, based on dry weight of the two components. These components may be combined using any convenient protocol, e.g., where an amount of BRP component is added with mixing to a chemical admixture, or vice versa.

BRP admixtures, e.g., as described above, may function as a variety of different types of admixtures, depending for example on the specific nature of the promoter employed, other chemical admixture components that are present, etc. As such, the admixtures may function as accelerating admixtures, water-reducing admixtures, water-reducing and set-retarding admixtures, high-range water-reducing admixtures, and mid-range water-reducing admixtures, each of which is described in further detail herein.

Accelerating admixtures are generally used to increase the cure rate (i.e., the hydration) of the settable cementitious composition and are of particular importance in applications where it is desirable for the settable cementitious composition to harden quickly and have early strength development. Accelerating admixtures, may include: a nitrate salt of an alkali metal, alkaline earth metal, or aluminum; a thiocyanate of an alkali metal, alkaline earth metal or aluminum; an alkanolamine; a thiosulfate of an alkali metal, alkaline earth metal, or aluminum; a hydroxide of an alkali metal, alkaline earth metal, or aluminum; a carboxylic acid salt of an alkali metal, alkaline earth metal, or aluminum (e.g., calcium formate); a polyhydroxylalkylamine; a halide salt of an alkali metal or alkaline earth metal (e.g., chloride). Specific examples of common materials included in accelerating admixtures include: calcium chloride, triethanolamine, sodium thiocyanate, sodium/calcium formate, sodium/calcium nitrite, calcium nitrate, aluminates, and silicates.

Water-reducing admixtures are generally used to reduce the water content of a cementitious composition by 5% or greater. Water-reducing admixtures may include: lignosulfonic acids and their salts, hydroxylated carboxylic acids and their salts, polysaccharides, melamine polycondensation products, naphthalene polycondensation products, and polycarboxylates.

Water-reducing and set-retarding admixtures are generally used to reduce the water content of a cementitious composition by 5% or more and to delay the set time of the cementitious composition. Water-reducing and set-retarding admixtures may include: lignosulfonic acids and their salts, hydroxylated carboxylic acids and their salts, polysaccharides, melamine polycondensation products, naphthalene polycondensation products, polycarboxylates, oxy-boron compounds, corn syrup, lignin, polyphosphonic acid, carboxylic acid, hydroxycarboxylic acid, polycarboxylic acid, hydroxylated carboxylic acid, such as fumaric, itaconic, malonic, borax, gluconic, and tartaric acid, lignosulfonates, ascorbic acid, isoascorbic acid, sulphonic acid-acrylic acid copolymer, and their corresponding salts, polyhydroxysilane, polyacrylamide, carbohydrates and mixtures thereof.

High-range water reducing admixtures are generally used to reduce the water content of a cementitious composition by 12-40% or more, increase slump, decrease placing time, and increase flowability. Such admixtures are commonly used in self-consolidating concrete. High-range water reducing admixtures may include: melamine sulfonate polycondensation products, naphthalene sulfonate polycondensation products, and polycarboxylates.

Mid-range water reducing admixtures are generally used to reduce the water content of a cementitious composition by between 5 and 10% without retardation of the initial set time. Mid-range water reducing admixtures may include: lignosulfonic acids and their salts, and polycarboxylates.

BRP admixtures, e.g., as described above, may be liquid or solid compositions. When present as liquid components, the admixtures may include, in addition to the BRP component and admixture components, an amount of water. The amount of water may vary, and in some instances ranges from 20 to 95, such as 60 to 75 wt %. When present as a solid, the solid may be a dehydrated version of a liquid admixture. The solid may be one that is produced from a liquid admixtures using any convenient protocol for removing water (e.g., free water) from the liquid, e.g., evaporation, freeze drying, lyophilization, etc. Upon combination with a suitable volume of water, the resultant solid dissolves in the water to produce a liquid admixture, e.g., as described above. In some instances, reconstitution is achieved by combining the solid (e.g., lyophilized) admixture with a sufficient amount of liquid, e.g., an aqueous medium, such as water, where the liquids to solids ratio employed may vary, and in some instances ranges from 1,000,000 to 1, such as 10,000 to 1, including 5,000 to 1, such as 1,000 to 1, e.g., 500 to 1, including 100 to 1. Solid admixtures may include a variety of different particle sizes and particle size distributions. For example, in some embodiments solid admixtures may include particulates having a size ranging from 1 to 10,000 µm, such as 10 to 1,000 µm and including 50 to 500 µm.

Concrete is normally blended in standard proportions. During the mixing and placement of concrete, not all of the cement alkaline component is consumed in the cementing reaction and therefore becomes inaccessible after the hardening of concrete. It is normal that 55-70% of the cement alkaline component is consumed in the reaction of cement during the curing of concrete. 30-45% of the cement remains unreacted after concrete curing. Cement efficiency in concrete mix design is an important characteristic when designing economical concrete mixes as well as lower the carbon footprint of the concrete, because the cement is the largest component of the carbon footprint. This excess, unreacted cement component, which is highly alkaline, can be reacted with bicarbonate (introduced as the additive/admixture (e.g., as described above) in liquid or solution state) causing an increase in early strength by forming carbonates. In some instances, this allows the cement content of a mix design to be lowered, improving the cost and carbon footprint of the concrete. In this fashion cement can be used more efficiently in concrete mix design. As such, aspects of the invention include low hydraulic cement (e.g., low OPC) cement formulations, where a given cement formulation may include 2% or less, such as 5% or less, including 10% or less (dry wt.) hydraulic cement as compared to a suitable control (i.e., the same blend which is not combined with a BRP additive/admixture), where the formulation may still have the same or better strength attainment and/or set properties as compared to the control, e.g., the same or enhanced strength and/or the same or faster set time.

BRP admixtures and their preparation are further described in U.S. Provisional Application No. 61/844,808 filed on Jul. 10, 2013, the disclosure of which is herein incorporated by reference.

Aspects of the invention further include settable cementitious compositions prepared from the BRP additives and admixtures, e.g., as described above. By "settable cementitious composition" is meant a flowable composition that is prepared from a cement and a setting liquid, where the flowable composition sets into a solid product following preparation. Settable cementitious compositions of the invention are prepared from combination of a cement, a setting liquid and a BRP additive/admixture (e.g., as described above), where the compositions may further include one or more additional components, such as but not limited to: aggregates, chemical admixtures, mineral admixtures, etc. Upon production, the flowable composition may have a variety of consistencies, e.g., paste, putty, etc., where the viscosity of the flowable composition may vary, ranging in some instances from 0 to 1000 mPa*s, such as 2 to 100 mPa*s. The flowable compositions set into a solid product following a period of time from production of the flowable composition, where this period of time may vary, and in some instances ranges from 1 min to 24 hrs, such as 1 hr to 3 hrs. The compressive strength of the solid products produced upon setting of the flowable compositions may also vary, ranging in some instances from 1 to 20,000 psi, such as 1000 to 5000 psi, as determined using the ASTM Test No. C109. The product into which the composition sets is characterized by including one or more mineral phases that are not present in the materials used to produce the composition, e.g., that are not present in the starting cement component. The cement and other optional components, e.g., an additional setting liquid, aggregate, etc., used to produce a subject settable cementitious compositions are reviewed in greater detail herein.

The term "cement" as used herein refers to a particulate composition that sets and hardens after being combined with a setting fluid, e.g., an aqueous solution, such as water. The particulate composition that makes up a given cement may include particles of various sizes. In some instances, a given cement may be made up of particles having a longest cross-sectional length (e.g., diameter in a spherical particle) that ranges from 1 nm to 100 μm, such as 10 nm to 20 μm and including 15 nm to 10 μm.

Cements of interest include hydraulic cements. The term "hydraulic cement" as used herein refers to a cement that, when mixed with a setting fluid, hardens due to one or more chemical reactions that are independent of the water content of the mixture and are stable in aqueous environments. As such, hydraulic cements can harden underwater or when constantly exposed to wet weather conditions. Hydraulic cements of interest include, but are not limited to Portland cements, modified Portland cements, and blended hydraulic cements.

In some embodiments, the cement is a Portland cement or a Portland cement blend. Portland cements are hydraulic cement compositions that are produced by grinding or pulverizing clinkers, which are materials consisting essentially of hydraulic calcium silicates and a small amount of one or more forms of calcium sulfate as an inter-ground addition. Clinkers are made from a sintered material that is produced when a raw mixture comprising calcium and silica in predetermined proportions is sintered, or heated to high temperatures. Examples of raw materials used to produce such a mixture include, but are not limited to, limestone and clay. In addition to Portland cement clinker, a limited amount of calcium sulfate (which controls the set time), and up to 5% minor constituents (as allowed by various standards) may also be included in a Portland cement. As defined by the European Standard EN197.1, "Portland cement clinker is a hydraulic material which shall consist of at least two-thirds by mass of calcium silicates ($3CaO.SiO_2$ and $2CaO.SiO_2$), the remainder consisting of aluminium- and iron-containing clinker phases and other compounds. The ratio of CaO to $SiO_2$ shall not be less than 2.0. The magnesium content (MgO) shall not exceed 5.0% by mass." In certain embodiments, a Portland cement is a Portland cement that satisfies the ASTM Standards and Specifications of C150 (Types I-VIII) of the American Society for Testing of Materials (ASTM C150-Standard Specification for Portland Cement). ASTM C150 covers eight types of Portland cement, each possessing different properties, and which are used specifically for those properties. The eight types of Portland cement are: Type 1 (normal); Type IA (normal, air-entraining), Type 11 (moderate sulfate resistance); Type IIA (moderate sulfate resistance, air-entraining); Type III (high early strength); Type IIIA (high early strength, air-entraining); Type IV (low heat of hydration); and Type V (high sulfate resistance). In some embodiments, a Portland cement may be a white Portland cement. White Portland cement is made from selected raw materials that only contain negligible amounts of iron and magnesium oxides, which are the chemical compounds that give ordinary Portland cement its grey color. White Portland cement is typically used for architectural and/or aesthetic purposes in visible structural walls, panels, terrazzo surfaces, stucco, cement paint, tile grout, and decorative concrete.

In some embodiments, a cement may be a blended hydraulic cement. The phrase "blended hydraulic cement" as used herein refers to a hydraulic cement composition that includes two or more types of cement materials. Materials used to form blended hydraulic cements include, but are not limited to: Portland cement, blast furnace slag, fly ash, silica fume, calcined clay, pozzolanic materials, hydrated lime, and combinations thereof. In some embodiments, a cement may be a masonry or mortar cement. Masonry and mortar cements are cements that are made from a mixture of a Portland cement or blended hydraulic cement and one or more plasticizing materials, such as limestone or hydrated or hydraulic lime. In certain embodiments, other materials may also be included in a masonry or mortar cement to modulate the properties of the cement, such as the setting time, workability, water retention, and durability, e.g., as described in greater detail below in the additives section.

In some embodiments, the cement component may be a non-hydraulic cement. By "non-hydraulic cement" is meant a cement whose products of hydration (i.e., the composition that is formed when the cement is mixed with a setting fluid) are not resistant to water. Examples of non-hydraulic cements include gypsum, plaster and lime cements. Non-hydraulic cements may be mixed with other components, such as pozzolanic materials, to render them resistant to water, i.e., to render them hydraulic.

In making a settable composition from a cement in accordance with the invention, the amount of the cement component that is combined with the other components may vary. In some instances, the amount of the cement component ranges from 5 to 30, such as 10 to 15, including 16 to 24% wt.

Setting liquids of interest include aqueous liquid compositions, such as pure water or water in combination with one or more solutes. In making a settable composition from a cement in accordance with the invention, the amount of the liquid component that is combined with the other components may vary. In some instances, the amount of the liquid component ranges from 5 to 25, such as 6 to 9, including 10 to 16% wt.

As summarized above, in making settable compositions according to the invention, the cement and setting liquid components are combined with a BRP additive and/or admixture, e.g., as described above. In making a settable composition from a cement in accordance with the invention, the amount of the BRP additive/admixture component that is combined with the other components may vary. In some instances, the amount of the BRP additive/admixture component ranges from less than 1 to 25, such as less than 1 to 9, including less than 10 to 16% wt.

In preparing settable cementitious compositions in accordance with aspects of the invention, the cement component, BRP additive/admixture and optional additional setting liquid may be combined with one or more additional components, as desired. Additional components of interest include, but are not limited to aggregates, other admixtures, reinforcement components, e.g., fiber reinforcement, reinforcing steel (rebar), and the like.

In some embodiments, aggregates may be used to produce the subject settable cementitious compositions (e.g., where concrete is desired). Aggregates of interest may vary, where such aggregates include, but are not limited to: sand, gravel, crushed stone, etc. When combined with aggregates, the subject settable cementitious compositions act as an adhesive that binds the aggregates together to form building materials, such as concrete.

Fine aggregates are materials that almost entirely pass through a Number 4 sieve (ASTM C125 and ASTM C33), such as silica sand. Coarse aggregates are materials that are predominantly retained on a Number 4 sieve (ASTM C125 and ASTM C33), such as silica, quartz, crushed round marble, glass spheres, granite, limestone, calcite, feldspar, alluvial sands, sands or any other durable aggregate, and mixtures thereof. As such, the term "aggregate" as used herein broadly refers to a number of different types of both coarse and fine particulate materials, including but not limited to: sand, gravel, crushed stone, slag, and recycled concrete. The amount and nature of an aggregate that is included in a subject settable cementitious composition may vary widely. In certain embodiments, the amount of aggregate may range from 25% to 85%, such as 40% to 70% and including 50% to about 70% (w/w) of the total composition made up of both the cement component, bicarbonate additive and the aggregate.

The various components that make up the subject settable cementitious compositions described herein (e.g., cement, BRP additive/admixture, optional additional setting liquid, aggregate and/or admixture (s)) may be combined using any convenient protocol and/or equipment to form a settable cementitious composition. In some embodiments, each individual component of a settable cementitious composition may be combined to produce a mixture at the time that the settable cementitious composition is produced. In some embodiments, part or all of the various components may be combined with one another in advance, before the settable cementitious composition is produced upon combination of all the components. For example, a setting liquid can be mixed with another component, e.g., BRP additive/admixture, prior to mixing with a cement to produce a settable cementitious composition. In certain embodiments, a setting liquid may be combined with an additional component, such as, e.g., an admixture, before mixing the setting liquid with the other components to produce a settable cementitious composition.

Any conventional mixing apparatus and/or methods may be used to produce a subject settable cementitious composition. Examples of conventional cement mixing equipment that may be employed include, but are not limited to: Hobart mixers; slant cylinder mixers; Omni mixers; Henschel mixers; V-type mixers; and Nauta mixers. Conventional containers may also be used for mixing the subject settable cementitious compositions, including, e.g., buckets, tubs, wheel barrows, and the like. In such embodiments, mixing of the components can be carried out by hand, e.g., by mixing the materials with a shovel, trowel, or gloved hand, depending on the volume and properties of the mixture.

The ratio of the liquid to the dry components which are combined to produce the settable cementitious composition may vary based on the properties of the components of the mixture and the desired properties of the produced cementitious composition. For example, in some embodiments, the ratio of the liquid components to the dry components in the mixture may range from 1:1.5 up to about 1:2, up to about 1:2.5, up to about 1:3, up to about 1:3.5, up to about 1:4, up to about 1:4.5, up to about 1:5 (w/w).

Combination of the cement, $CO_2$ sequestering cement additive and optional components results in the production of a settable cementitious composition. As reviewed above, by "settable cementitious composition" is meant a flowable composition that is prepared from a cement and a setting liquid, where the flowable compositions sets into a solid product following preparation. Upon production, the flowable composition may have a variety of consistencies, e.g., past, putty, etc., where the viscosity of the flowable composition may vary, ranging in some instances from 0 to 1000 mPa*s, such as 2 to 100 mPa*s. The flowable compositions set into a solid product following a period of time from production of the flowable composition, where this period of time may vary, and in some instances ranges from 1 min to 24 hrs, such as 1 hr to 3 hrs. The compressive strength of the solid products produced upon setting of the flowable compositions may also vary, ranging in some instances from 1 to 20,000 psi, such as 1000 to 5000 psi, as determined using the ASTM Test No. C109.

LOI or loss on ignition is a common method of analysis to observe residual unburnt carbonate, in the case of portland cement, or residual unburnt fuel in the case of an ash such as fly ash (FA). LOI can be applied to determine $CO_2$ content of other materials and pozzolans as well, such as blast furnace slag. Methods of LOI analysis on cement is determined by ASTM C114 and standardized by heating a cement sample to 950+/−50° C. for a minimum of 15 minutes. The process removes water and residual $CO_2$ from the carbonate phase residual of the cement and is applied in an effort to standardize industry heating and uniform resultant cement. Loss on Ignition (LOI) can be measured on final cement and concrete specimens that employ a BRP additive/admixture, e.g., as described herein. For small volume definition, LOI of hardened cement samples that use a BRP additive/admixture can be used to define the amount of sequestered carbon in the final material. In the case of larger volume identification, LOI of hardened concrete samples employing a $CO_2$ sequestering cement additive can be employed. In the case of performing LOI on final cement compositions containing a BRP additive/admixture, the expected LOI may, in some instances, range from 0 and 7.76% and in the case of LOI being performed on the final concrete, the LOI may, in some instances, range from 0 and 25.1% dependent on the amount of residual water and carbonate promoted during the hardening of cement and concrete sample.

Settable cementitious compositions as described herein find use in a variety of different applications, including as building or construction materials. Specific structures in which the settable compositions of the invention find use include, but are not limited to: pavements, architectural structures, e.g., buildings, foundations, motorways/roads, overpasses, parking structures, brick/block walls and footings for gates, fences and poles. Mortars of the invention find use in, e.g., binding construction blocks (e.g., bricks) together, as well as filling gaps between construction blocks. Mortars can also be used to fix or repair an existing structure, e.g., to replace sections where the original mortar has become compromised or eroded.

In using the subject settable cementitious compositions to produce a structure, e.g., as described above, such methods may include positioning a settable cementitious composition at a location, e.g., a building site, mold, etc.; and allowing the settable cementitious composition to set into a solid product at the location, where the setting time may vary, e.g., as described above.

Cementitious compositions according to certain embodiments as described herein benefit from what is known in the art as early age carbonation. As known in the art, early age carbonation occurs when the carbonation reactions occur alongside the early hydration of the cement through a deliberate exposure of fresh concrete to $CO_2$. When freshly mixed concrete is reacted with $CO_2$, a carbonation reaction occurs alongside the normal hydration. The carbonation occurs rapidly and contributes to a denser and stronger concrete. The calcite formation contributes to strength development. Use of bicarbonate additives, e.g., as described herein, in some instances provides for early age carbonation and its associated benefits.

The subject settable cementitious compositions also find use in sequestering anthropogenic $CO_2$ in building materials as a way of reducing the amount of anthropogenic $CO_2$ that is released into the earth's atmosphere. For example, the subject methods can be used to capture large amounts of $CO_2$ from industrial consumption of fossil fuels, and the captured $CO_2$ can then be converted into bicarbonate additives that are incorporated into the settable cementitious compositions. In this way, $CO_2$ that is generated from industrial processes can be removed from emission gasses, such as flue gasses, and incorporated into building materials on a large scale to reduce the overall amount of $CO_2$ in the earth's atmosphere. The subject methods and compositions therefore provide for reducing the amount of carbon emissions from industrial processes, and also provide for disposing of emitted carbon by incorporating the emitted carbon into building materials.

Use of $CO_2$ sequestering cement admixtures in the production of settable cementitious compositions, e.g., as described above, can be employed to reduce the carbon footprint of cement and concrete compositions, and thereby provide reduced-carbon footprint cement and concrete compositions. Reduced-carbon footprint cement concrete compositions that may include, for example, an ordinary Portland cement (OPC) component but have a reduced carbon footprint as compared to a concrete that only includes, for example, OPC as the cement component, e.g., by virtue of the presence of the bicarbonate additive. In some embodiments, the reduced-carbon footprint cement and concrete compositions may include carbon derived from a fuel used by humans (e.g., a fossil fuel). For example, reduced-carbon footprint cement and concrete compositions according to aspects of the invention may include carbon that was released in the form of $CO_2$ from combustion of a fossil fuel. In certain embodiments, the carbon sequestered in a composition of the invention (e.g., a reduced-carbon footprint concrete composition) comprises a carbonate, bicarbonate, or a mixture thereof. With respect to calculation of carbon footprint, the carbon footprint of a cement or concrete may be determined by multiplying the pounds per cubic yard of each constituent by its per pound carbon footprint, summing these values, and adding 10.560 kg/yd$^3$ (the carbon footprint of transporting one yard of concrete 20 miles on average). With respect to the OPC component, assuming an average $CO_2$ release from Portland cement production of 0.86 tons $CO_2$/ton cement (as reported for California Cement Climate Action Team), each pound of Portland cement has a production carbon footprint of 0.86 pounds. Assuming an average transportation distance of 100 miles, the transportation footprint for each pound of Portland cement is 0.016 pounds, for a total carbon footprint of 0.876 pounds $CO_2$ per pound of OPC. For purposes of carbon footprint calculation, conventional aggregate may be assumed to have a carbon footprint of 0.043 lbs. $CO_2$/lb. aggregate, while the carbon footprint of conventional supplementary cementitious materials (SCMs), e.g., fly ash, slag, etc., may be assumed to be 0.045 lbs. $CO_2$/lb. conventional SCM. Compared to reference concrete comprising conventional aggregate (e.g., sand and/or rock) and OPC as the only cement component, the magnitude of the carbon footprint reduction of the reduced-carbon footprint concrete compositions of the invention may be equal to or more than 25 lbs. $CO_2$/yd$^3$ concrete, 50 lbs. $CO_2$/yd$^3$ concrete, 100 lbs. $CO_2$/yd$^3$ concrete, more than 200 lbs. $CO_2$/yd$^3$ concrete, more than 300 lbs. $CO_2$/yd$^3$ concrete, more than 400 lbs. $CO_2$/yd$^3$ concrete, or more than 500 lbs. $CO_2$/yd$^3$ concrete. These reductions in carbon footprint may be achieved with concrete mixes that include $CO_2$ sequestering admixture, e.g., as described above. In certain embodiments, reduced-carbon footprint compositions of the invention are carbon neutral in that they have substantially no carbon footprint (if any) as determined using, for example, the calculation guidelines provided above. Carbon neutral concrete compositions of the invention include those compositions that exhibit a carbon footprint of less than 50 lbs. $CO_2$/yd$^3$ concrete, such as less than 25 lbs. $CO_2$/yd$^3$ concrete, including less than 10 lbs. $CO_2$/yd$^3$ concrete, for example, less than 5 lbs. $CO_2$/yd$^3$ concrete. In some embodiments, the carbon neutral compositions exhibit a carbon footprint of 0 $CO_2$/yd$^3$ concrete or less, such as a negative carbon footprint of less than (i.e., more negative than) −1 lbs. $CO_2$/yd$^3$ concrete, less than −2 lbs. $CO_2$/yd$^3$ concrete, less than −3 lbs. $CO_2$/yd$^3$ concrete, less than −4 lbs. $CO_2$/yd$^3$ concrete, or less than −5 lbs. $CO_2$/yd$^3$ concrete.

In some embodiments, small-carbon footprint concretes have a significantly negative carbon footprint. In such embodiments, the negative carbon footprint of the composition may be less than (i.e., more negative than) −10, −25, −50, −100, −250, −500, −750, or −1000 lbs. concrete. To achieve an reduced carbon footprint composition, in addition to using a $CO_2$ sequestering admixture, e.g., as described herein, one may use one or more additional $CO_2$ sequestering compositions, e.g., cements, supplementary cementitious compositions, aggregates, etc., such as described in U.S. Pat. Nos. 7,753,274; 7,753,618; and 7,815,880; the disclosures of which are herein incorporated by reference.

Methods of using BRP additives/admixtures as well as products produced therefrom are further described in U.S. Provisional Application Ser. No. 61/807,230 filed on Apr. 1, 2013; U.S. Provisional Application Ser. No. 61/819,427 filed on May 3, 2013; and U.S. Provisional Application Ser. No. 61/844,808; the disclosures of which are herein incorporated by reference.

BRP additives/admixtures, e.g., as described above, may be present in kits, which kits may include one or more additional components. As such, aspects of the invention include kits that include BRP additives/admixtures, optionally in combination with one or more additional components that may be employed to produce a settable cementitious composition, where such additional optional components of interest include, but are not limited to: cements, concrete blends, setting liquids, additional admixtures, etc. The various components of the kits may be present in separate containers, or two more of the disparate components may be combined into a single container, where desired. For example, a dried BRP additive/admixture may be combined with a cement in a single container, and sold with a separate container of a setting liquid.

In kits that include both liquid and solid components, the ratio of liquid components to solid components (expressed as a decimal amount based on dividing the weight of the liquid components in the mixture by the weight of the solid components in the mixture) may vary depending on the desired consistency of the settable cementitious composition following combination of the components, where the ratio may range from 0.2 to 1.0, such as from 0.3 to 0.6. Of interest in certain embodiments are kits where the liquids to solids ratio employed in such methods may range from 0.15 to 0.5, such as from 0.2 to 0.45. In some instances, e.g., for lay consumer use, the BRP additive/admixture is present in liquid form, and may be present in volumes ranging from 1 oz. to 55 gallons, such as 1 gallon to 15 gallons and including 2 gallons to 5 gallons. In such instances, the amount of dry components in the kit may be present in amounts ranging from 5 lbs. to 100 lbs., such as 25 lbs. to 50 lbs.

In addition to the above-mentioned components, the subject kits may further include instructions for using the components of the kit to practice the subject methods. The instructional material may also be instructional material for using the cement compositions, e.g., it may provide building techniques and principals for a particular application in which the cementitious composition is to be employed. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or sub-packaging), etc. In other embodiments, the instructions are present as an electronic storage data file present on a suitable computer readable storage medium, e.g., portable flash drive, memory stick or card, CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

Fly-Ash Containing Cementitious Compositions

BRP compositions, additives and/or admixtures, e.g., as described above, find use in, among other applications, fly-ash containing cementitious compositions. Such compositions are prepared from a BRP component (e.g., as described above, a cement component (e.g., as described above) and a fly ash component. The term "fly ash" as used herein refers to a material that is produced from burning coal, and comprises the non-combustible mineral portions of coal. Fly ash generally comprises spherical particles that are rich in silica, alumina and calcium and is available in two different classes, referred to as class F and class C. Class F fly ash is made from burning anthracite and/or bituminous coal, while class C fly ash is produced from lignite or subbituminous coal. Any class of fly ash may be used in conjunction with the subject methods for making settable cementitious compositions.

Fly ash may be used as an admixture in concrete to replace a portion of the Portland cement. As such, in certain embodiments, the fly ash component may be blended with the cement component of the settable cementitious composition. In some embodiments, fly ash may be combined with the cement component to produce a blend that comprises 1 to 60% by weight fly ash component, such as 5 to 30% by weight fly ash component, including 10 to 20% by weight fly ash component.

The BRP components, as described above, can be used in conjunction with a cement blend that includes fly ash to overcome one or more drawbacks of fly ash-containing cement blends (e.g., slow strength gain, longer setting times). For example, combining a subject bicarbonate component with a fly ash component results in a settable cementitious composition that attains strength more quickly and/or sets faster than a settable cementitious composition that includes fly ash but does not contain a bicarbonate component. In compositions that include a bicarbonate component, the curing time is, in some instances, 3 to 70%, such as 5 to 30%, faster than compositions that lack a bicarbonate component, e.g., as determined using ASTM C403. In some instances, the compositions have an initial set time ranging from 2 to 12 minutes, such as 2 to 7 minutes, and a final set time ranging from 4 to 15 minutes, such as 8 to 15 minutes. In some embodiments, the subject settable cementitious compositions that include fly ash and a bicarbonate component achieve a set strength ranging from 500 to 3000 psi in 3 days, 1000 to 8000 psi in 7 days, and 3000 to 15000 psi in 28 days, such as 3500 to 8000 at 28 days (as determined using ASTM C39).

In preparing settable cementitious compositions in accordance with aspects of the invention, the cement component, BRP component, fly ash component and an optional additional setting liquid (e.g., as described above) may be combined with one or more additional components, as desired. Additional components of interest include, but are not limited to aggregates, other admixtures, reinforcement components, e.g., fiber reinforcement, reinforcing steel (rebar), and the like. Such materials are described in further detail in U.S. Provisional Patent Application No. 61/819,427 filed on May 3, 2013, the disclosure of which is herein incorporated by reference in its entirety.

In some instances, the cementitious composition may include a third cementitious component, such that it may be a ternary composition. In some instances, the third cementitious component, in addition to the fly ash and hydraulic cement components, may be a slag cement. By slag cement is meant a cement that includes Ground-granulated blast-furnace slag (GGBS or GGBFS). In some embodiments, the slag cement component may make up from 10 to 40, such as 15 to 35, including 20 to 30% by weight of the total dry components.

The various components of the subject settable cementitious compositions described herein (e.g., cement component, fly ash component, BRP component, optional additional setting liquid, aggregate and/or admixture(s)) may be combined using any convenient protocol and/or equipment to form a settable cementitious composition, e.g., as described above.

The preparation and use of fly-ash containing cementitious compositions, e.g., as described above, is further detailed in U.S. Provisional Application Ser. No. 61/866,988 filed on Aug. 16, 2013; the disclosure of which is herein incorporated by reference.

Carbonate Production from BRP

Following preparation of the BRP composition (as well as any storage thereof, as desired), in some instances the product may be further manipulated in some manner. For example, the product or component thereof (e.g., LCP) may be manipulated to produce solid phase carbonate compositions, and therefore sequester $CO_2$ from the initial $CO_2$ source into a solid form. In certain instances of such embodiments, the product or component thereof (e.g., LCP) is combined with a cation source (e.g., a source of one or more alkaline earth metal cations) under conditions sufficient to produce a solid carbonate composition. Cations of different valances can form solid carbonate compositions (e.g., in the form of carbonate minerals). In some instances, monovalent cations, such as sodium and potassium cations, may be employed. In other instances, divalent cations, such as alkaline earth metal cations, e.g., calcium and magnesium cations, may be employed. When cations are added to the bicarbonate rich product or component thereof (e.g., LCP), precipitation of carbonate solids, such as amorphous calcium carbonate when the divalent cations include $Ca^{2+}$, may be produced with a stoichiometric ratio of one carbonate-species ion per cation.

Any convenient cation source may be employed in such instances. Cation sources of interest include, but are not limited to, the brine from water processing facilities such as sea water desalination plants, brackish water desalination plants, groundwater recovery facilities, wastewater facilities, and the like, which produce a concentrated stream of solution high in cation contents. Also of interest as cation sources are naturally occurring sources, such as but not limited to native seawater and geological brines, which may have varying cation concentrations and may also provide a ready source of cations to trigger the production of carbonate solids from the bicarbonate rich product or component thereof (e.g., LCP). The cation source employed in such solid carbonate production steps may be the same as or different from the aqueous media employed in the bicarbonate rich product production step, e.g., as described above. For example, the aqueous medium employed to produce a bicarbonate rich product may be native seawater with a calcium cation concentration of approximately 400 ppm. A more concentrated cation solution, such as the brine concentrate from a seawater desalination plant, with over twice the native seawater concentration of calcium cation, may then be employed for the second precipitation step.

Alternatively or in addition to introduction of a cation, e.g., as described above, other parameters of the BRP composition may be modified to promote carbonate mineral precipitation. For example, where the BRP is a pressurized composition, the pressure may be reduced to a level which promotes precipitation of carbonate mineral from the BRP composition. In some instances, the pressure is reduced by 15 psi or more, such as 150 psi or more, and in some instances to a value ranging from 2000 to 15 psi, such as 200 to 14.8 psi.

Where desired, modifying components may be provided in the BRP composition being subjected to solid carbonate precipitation conditions in order to influence the carbonate precipitation process in some desirable manner, e.g., in terms of rate, identity of product carbonates, etc. For example, ions, e.g., chloride 'spectator' ions, may be included which influence the formation of calcium carbonate from bicarbonate-rich solutions. Alternatively, ions in the bulk phase partition between the LCP and the bulk solution phase in the bicarbonate rich product, may be employed as catalysts to the phase separation into two liquids. Due to the bicarbonate-rich nature of the bicarbonate rich product, these other partitioned ions may further impact the continued formation of various crystalline solid polymorphs of calcium carbonate, or inhibit the formation of other crystalline polymorphs. Manipulation of these partitioned companion ions may be optimized to guide the formation of LCPs during the bicarbonate rich product production step (e.g., as described above) as well as to guide the growth of the precipitated non-crystalline or crystalline solid phase. The ultimate use of the bicarbonate rich product or component thereof may impact the decision of which influencing ion to employ in such embodiments. For example, where the bicarbonate rich product or a component thereof is employed as a setting medium for a hydraulic cement, influencing ions are employed that do not negatively impact the properties of the cement. For example, sodium and chloride ions may be avoided as influencing ions in such embodiments.

In some instances, carbonate production is carried out under conditions where LCPs exist. As such, carbonate production is carried out a pH values which are permissive of LCP existence, e.g., pH values of 9.5 or less, such as 9.3 or less.

During the production of solid carbonate compositions from the bicarbonate rich product or component thereof (e.g., LCP), one mol of $CO_2$ may be produced for every 2 mols of bicarbonate ion from the BRLCP product composition. For example, where solid carbonate compositions are produced by adding calcium cation to the BRLCP product composition, the production of solid carbonate compositions, e.g., the form of amorphous calcium carbonate minerals, may proceed according to the following reactions:

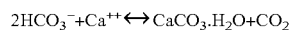

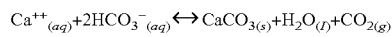

While the above reaction shows the production of 1 mol of $CO_2$, 2 moles of $CO_2$ from the $CO_2$ containing source gas were initially converted to bicarbonate. As such, the overall process sequesters a net 1 mol of $CO_2$ and therefore is an effective $CO_2$ sequestration process, with a downhill standard-state thermodynamic energy profile of $-37$ kJ $mol^{-1}$ for the above reaction.

Where desired, $CO_2$ generated during production of solid carbonate compositions may be actively removed from the system, e.g., in order to enhance the production of carbonate solids. By removing $CO_2$ actively from the system, like photosynthesis does when it is associated with calcification, like, e.g., in corals, the above reaction can be forced to the right, thereby favoring the production of solid carbonates. Any convenient protocol for removing $CO_2$ from the system may be employed. For example, the $CO_2$ may be driven into gas form from solution, whereby it will readily separate from the liquid in the system and can be removed. $CO_2$ may be driven into gas form using any convenient protocol. In some instances, a catalyst may be employed, such as carbonic anhydrase, which is both an anhydrase and a hydrase, and among other things is responsible for pulling $CO_2$ out of blood into lungs to exhale. When employed, the amount of carbonic anhydrase that is present in the system will be sufficient to provide a desired activity, e.g., an activity ranging from $10^3$ to $10^6$ $s^{-1}$, such as from $10^4$ to $10^5$ $s^{-1}$. Another approach for producing $CO_2$ from the liquid in the system, and thereby enhancing the production of carbonate solids, includes bubbling $N_2$ gas through the liquid in the system, which will purge the $CO_2$, converting $HCO_3^-$ to $CO_3^{2-}$, and trigger solid carbonate (e.g., $CaCO_3$) precipitation. In some embodiments, both adding cation, such as $Ca^{2+}$, and removing $CO_2$ from the system may be employed to force the precipitation of solid carbonates from the liquid. The method of these embodiments may be viewed as one that produces a mole of purified $CO_2$ for every two moles of $CO_2$ removed from the gaseous stream, and thereby one that transforms a dilute flue gas to a concentrated near-pure stream of $CO_2$.

Where carbonate compositions are precipitated, e.g., as described above, from the bicarbonate rich product, the product carbonate compositions may vary greatly. In some instances, the product compositions are meta-stable carbonate compounds that, upon combination with fresh water, dissolve and produce different minerals that are more stable in fresh water than compounds of the initial precipitate product composition. (Although the compounds of the initial precipitate product composition may dissolve upon combination with freshwater and then produce different components, $CO_2$ gas is not liberated in significant amounts, or in some cases at all, in any such reaction). The compounds of the initial precipitate product composition may be ones that are more stable in salt water than they are in freshwater, such that they may be viewed as saltwater metastable compounds.

The carbonate compounds may be amorphous or crystalline. The particular mineral profile, i.e., the identity of the different types of different carbonate minerals and the amounts of each, in the carbonate compound composition may vary and will be dependent on the particular nature of the water source from which it is derived, as well as the particular conditions employed to derive it. In certain embodiments, the carbonate compounds are present as small particles, e.g., with particle sizes ranging from 0.1 microns to 100 microns, e.g., 1 to 100 microns, or 10 to 100 microns, or 50 to 100 microns, in some embodiments 0.5 to 10 microns, as determined by Scanning electron microscopy. In some embodiments, the particle sizes exhibit a bimodal or multi-modal distribution. In certain embodiments, the particles have a high surface are, e.g., ranging from 0.5 to 100 $m^2/\mu m$, 0.5 to 50 $m^2/\mu m$, such as from 0.5 to 2.0 $m^2/\mu m$, as determined by Brauner, Emmit, & Teller (BET) Surface Area Analysis. In some embodiments, the $CO_2$ sequestering products produced by methods of the invention may include rod-shaped crystals and amorphous solids. The rod-shaped crystals may vary in structure, and in certain embodiments have length to diameter ratio ranging from 500 to 1, such as 10 to 1. In certain embodiments, the length of the crystals ranges from 0.5 µm to 500 µm, such as from 5 µm to 100 µm. In yet other embodiments, substantially completely amorphous solids are produced.

In some instances, the precipitated carbonates are highly reflective. As the materials are highly reflective, they have a high total surface reflectance (TSR) value. TSR may be determined using any convenient protocol, such as ASTM E1918 Standard Test Method for Measuring Solar Reflectance of Horizontal and Low-Sloped Surfaces in the Field (see also R. Levinson, H. Akbari, P. Berdahl, Measuring solar reflectance—Part II; review of practical methods, LBNL 2010). In some instances, the materials exhibit a TSR value ranging from Rg;0=0.0 to Rg;0,=1.0, such as Rg;0,=0.25 to Rg;0,=0.99, including Rg;0,=0.40 to Rg;0,=0.98, e.g., as measured using the protocol referenced above.

In some instances, the precipitated carbonates are highly reflective of near infra-red (NIR) light. By NIR light is meant light having a wavelength ranging from 700 nanometers (nm) to 2.5 mm. NIR reflectance may be determined using any convenient protocol, such as ASTM C1371-04a (2010)e1 Standard Test Method for Determination of Emittance of Materials Near Room Temperature Using Portable Emissometers (see internet address product by placing "http://www." in front of "astm.org/Standards/C1371.htm) or ASTM G173-03(2012)") Standard Tables for Reference Solar Spectral Irradiances: Direct Normal and Hemispherical on 37° Tilted Surface (see internet address product by placing "http://" in front of "rredc.nrel.gov/solar/spectra/am1.5/ASTMG173/ASTMG173.html"). In some instances, the materials exhibit a NIR reflectance value ranging from Rg;0=0.0 to Rg;0=1.0, such as Rg;0=0.25 to Rg;0=0.99, including Rg;0=0.40 to Rg;0=0.98, e.g., as measured using the protocol referenced above.

In some instances, the precipitated carbonates are highly reflective of ultra-violet (UV) light. By UV light is meant light having a wavelength ranging from 400 nm and 10 nm. UV reflectance may be determined using any convenient protocol, such as ASTM G173-03 (2012) Standard Tables for Reference Solar Spectral Irradiances: Direct Normal and Hemispherical on 37° Tilted Surface. In some instances, the $CO_2$ sequestering materials exhibit a UV value ranging from Rg;0=0.0 to Rg;0=1.0, such as Rg;0=0.25 to Rg;0=0.99, including Rg;0=0.4 to Rg;0=0.98, e.g., as measured using the protocol referenced above.

In some instances, the precipitated carbonates are also reflective of visible light. By visible light is meant light having a wavelength ranging from 380 nm to 740 nm. Visible light reflectance properties may be determined using any convenient protocol, such as ASTM G173-03 (2012) Standard Tables for Reference Solar Spectral Irradiances: Direct Normal and Hemispherical on 37° Tilted Surface. In some instances, the $CO_2$ sequestering materials exhibit a visible light reflectance value ranging from Rg;0=0.0 to Rg;0=1.0, such as Rg;0=0.25 to Rg;0=0.99, including Rg;0=0.4 to Rg;0=0.98, e.g., as measured using the protocol referenced above.

As summarized above, the precipitated carbonates may be amorphous or microcrystalline. In some instances, the materials are microcrystalline. As the materials are microcrystalline, the crystal size, e.g., as determined using the Scherrer equation applied to the FWHM of X-ray diffraction pattern, is small, and in some instances is 1000 microns or less in diameter, such as 100 microns or less in diameter, and including 10 microns or less in diameter. In some instances, the crystal size ranges in diameter from 1000µ to 0.001µ, such as 10 to 0.001µ, including 1 to 0.001µ. In some embodiments, the materials produced by methods of the invention may include rod-shaped crystals and amorphous solids. The rod-shaped crystals may vary in structure, and in certain embodiments have length to diameter ratio ranging from 500 to 1, such as 10 to 1. In certain embodiments, the length of the crystals ranges from 0.5 µm to 500 µm, such as from 5 µm to 100 µm. In yet other embodiments, substantially completely amorphous solids are produced.

The density, porosity, and permeability of the precipitated carbonates may vary according to the application. With respect to density, while the density of the material may vary, in some instances the density ranges from 5 $g/cm^3$ to 0.01 $g/cm^3$, such as 3 $g/cm^3$ to 0.3 $g/cm^3$ and including 2.7 $g/cm^3$ to 0.4 $g/cm^3$. With respect to porosity, as determined by Gas Surface Adsorption as determined by the BET method (Brown Emmett Teller (e.g., as described at http://en.wikipedia.org/wiki/BET_theory, S. Brunauer, P. H. Emmett and E. Teller, *J. Am. Chem. Soc.,* 1938, 60, 309. doi:10.1021/ja01269a023) the porosity may range in some instances from 100 $m^2/g$ to 0.1 $m^2/g$, such as 60 $m^2/g$ to 1 $m^2/g$ and including 40 $m^2/g$ to 1.5 $m^2/g$. With respect to permeability, in some instances the permeability of the material may range from 0.1 to 100 darcies, such as 1 to 10 darcies, including 1 to 5 darcies (e.g., as determined using the protocol described in H. Darcy, Les Fontaines Publiques de la Ville de Dijon, Dalmont, Paris (1856).). Permeability may also be characterized by evaluating water absorption of the material. As determined by water absorption protocol, e.g., the water absorption of the material ranges, in some embodiments, from 0 to 25%, such as 1 to 15% and including from 2 to 9%. The hardness of the materials may also vary. In some instances, the materials exhibit a Mohs hardness of 3 or greater, such as 5 or greater, including 6 or greater, where the hardness ranges in some instances from 3 to 8, such as 4 to 7 and including 5 to 6 Mohs (e.g., as determined using the protocol described in American Federation of Mineralogical Societies. "Mohs Scale of Mineral Hardness"). Hardness may also be represented in terms of tensile strength, e.g., as determined using the protocol described in ASTM C1167. In some such instances, the material may exhibit a compressive strength of 100 to 3000 N, such as 400 to 2000 N, including 500 to 1800 N. In some instances, the carbonate compositions exhibit second and even third order birefringence.

Reflectance spectroscopy in the visible and near infrared (0.35-2.55 um) offers a rapid, inexpensive, nondestructive technique for determining the mineralogy and gaining information on the minor element chemistry of carbonate minerals and rocks. Spectra of all commonly occurring anhydrous end-member carbonate minerals contain seven strong absorption bands at wavelengths >1.6 um due to vibrations of the carbonate radical. Positions, widths, and spacing between carbonate bands are diagnostic of mineralogy. Differences in positions of carbonate bands between spectra of different minerals are primarily due to differences in mass of the major cation, with cation electronegativity playing a secondary role. Spectra of calcite group minerals may contain absorption features due to transition metal cations such as Fe and Mn, which can also aid in mineral identification. Spectra confirm the occurrence of both cations in the divalent state. $Fe^{2+}$ produces a broad feature near 1.1 µm whose position and degree of doubling are related to the size and degree of distortion of the octahedral site, as predicted by crystal field theory. $Mn^{2+}$ and $Fe^{2+}$ produce very strong absorption bands in the minerals for which they are the major cation (rhodochrosite and siderite, respectively), making it easy to distinguish these from other carbonate minerals, even when presence of water bands may make it difficult to determine accurately carbonate band positions.

The precipitated product may include one or more different carbonate compounds, such as two or more different carbonate compounds, e.g., three or more different carbonate compounds, five or more different carbonate compounds, etc., including non-distinct, amorphous carbonate compounds. Carbonate compounds of precipitated products of the invention may be compounds having a molecular formulation $X_m(CO_3)_n$ where X is any element or combination of elements that can chemically bond with a carbonate group or its multiple, wherein X is in certain embodiments an alkaline earth metal and not an alkali metal; wherein m and n are stoichiometric positive integers. These carbonate compounds may have a molecular formula of $X_m(CO_3)_n.H_2O$, where there are one or more structural waters in the molecular formula. The amount of carbonate in the product, as determined by coulometry using the protocol described as coulometric titration, may be 40% or higher, such as 70% or higher, including 80% or higher.

The carbonate compounds of the precipitated products may include a number of different cations, such as but not limited to ionic species of: calcium, magnesium, sodium, potassium, sulfur, boron, silicon, strontium, and combinations thereof. Of interest are carbonate compounds of divalent metal cations, such as calcium and magnesium carbonate compounds. Specific carbonate compounds of interest include, but are not limited to: calcium carbonate minerals, magnesium carbonate minerals and calcium magnesium carbonate minerals. Calcium carbonate minerals of interest include, but are not limited to: calcite ($CaCO_3$), aragonite ($CaCO_3$), vaterite ($CaCO_3$), ikaite ($CaCO_3.6H_2O$), and amorphous calcium carbonate ($CaCO_3$). Magnesium carbonate minerals of interest include, but are not limited to magnesite ($MgCO_3$), barringtonite ($MgCO_3.2H_2O$), nesquehonite ($MgCO_3.3H_2O$), lanfordite ($MgCO_3.5H_2O$), hydromagnisite, and amorphous magnesium calcium carbonate ($MgCO_3$). Calcium magnesium carbonate minerals of interest include, but are not limited to dolomite ($CaMg)(CO_3)_2$), huntite ($Mg_3Ca(CO_3)_4$) and sergeevite ($Ca_2Mg_{11}(CO_3)_{13}.H_2O$). The carbonate compounds of the product may include one or more waters of hydration, or may be anhydrous. In some instances, the amount by weight of magnesium carbonate compounds in the precipitate exceeds the amount by weight of calcium carbonate compounds in the precipitate. For example, the amount by weight of magnesium carbonate compounds in the precipitate may exceed the amount by weight calcium carbonate compounds in the precipitate by 5% or more, such as 10% or more, 15% or more, 20% or more, 25% or more, 30% or more. In some instances, the weight ratio of magnesium carbonate compounds to calcium carbonate compounds in the precipitate ranges from 1.5-5 to 1, such as 2-4 to 1 including 2-3 to 1. In some instances, the precipitated product may include hydroxides, such as divalent metal ion hydroxides, e.g., calcium and/or magnesium hydroxides.

In some instances solid carbonate compound production and $CO_2$ gas generation may be enhanced by integrating the above method with a method of cooling a power plant. For example, large volumes of bicarbonate buffered aqueous media, e.g., natural occurring bicarbonate buffered waters, such as obtained from the oceans, are contacted with the raw flue gases, e.g., from a power plant such as from a coal-fired power plant, in order to produce a bicarbonate rich product, e.g., as described above. The resultant bicarbonate rich product is then employed to cool the power plant, e.g., using the bicarbonate rich product as a coolant in the power plant water cooling system. In other words, the bicarbonate rich product is then passed through the power plant to serve as cooling water for the power plant, which cools the power plant but warms the water in the process in a back-end step. In such instances, temperature differential between the temperature of the bicarbonate rich product being input into the cooling system and the temperature of the bicarbonate rich product being output by the cooling system may range from 5 to 100° C., such as 10 to 100° C. and including 20 to 100° C., such that the temperature of the bicarbonate rich product entering the cooling system may range from −1.4 to 50° C., such as −1.0 to 40° C. and the temperature of the bicarbonate rich product output from the cooling system may range from 20 to 100° C., such as 25 to 100° C. The warming of the bicarbonate rich product decreases the solubility of $CO_2$ in the water, driving off $CO_2$ gas, and decreasing the solubility of carbonate compounds, such as $CaCO_3$, causing precipitation of such compounds. This reaction can be further accelerated by the presence of catalysts, such as the enzymes, synthetic catalysts or colloidal metal particles that accelerate the reaction, e.g., carbonic anhydrases, transition metal aza-macrocycles or transition metal colloidal particles, such as described above.

In some instances, the above methods treat large volumes of raw flue gas produced by a power plant (such as a coal fired power plant) at a rate comparable to the volumes produced by the power plant. For instance, a 500 MW coal-fired power plant may produce about 8 million tons of $CO_2$ per year, or about 20,000 tons of $CO_2$ per day. A typical coastal power plant may circulate about 1 billion gallons of seawater per day, or about 50,000 gallons per ton of $CO_2$. 50,000 gallons of seawater contains about 800 kg of $Ca^{2+}$ and 2,400 kg $Mg^{2+}$, or about 3,200 kg of total divalent cations. In order to form a ton of $CaCO_3$, 440 kg of $CO_2$ (or 600 kg $HCO_3^-$), and 400 kg of $Ca^{2+}$ are needed. Therefore, seawater contains twice as much $Ca^{2+}$ as is needed, and six times as much $Mg^{2+}$ as is needed to capture the $CO_2$ as one ton of carbonate mineral solid as $MgCO_3$ or $CaCO_3$.

In these embodiments, the sequencing of the addition of $Ca^{2+}$ may vary depending on the concentration of bicarbonate achieved in the front-end bicarbonate rich product production step as compared to the ambient levels of $Ca^{2+}$ in the natural water being employed as the bicarbonate buffered aqueous medium, and whether $CaCO_3$ is the preferred precipitate or some other carbonate compound is preferred, e.g., $MgCO_3$, $CaMg(CO_3)_2$, etc. Seawater contains about 410 mg/L $Ca^{2+}$ and about 1200 mg/L $Mg^{2+}$, whereas typical ground waters from inland basins typically contain 2000-40,000 mg/L $Ca^{2+}$ and less than 1000 mg/L $Mg^{2+}$. For instance, if $CaMg(CO_3)_2$, dolomite or protodolomite, are the preferred carbonate minerals, then sea water would be the preferred feedstock, and it may not be necessary to add 'hard water' containing $Ca^{2+}$. At inland sites, where $CaCO_3$ may be the preferred carbonate mineral, 'hard water' containing high levels of $Ca^{2+}$, could be brought in as a second step after the bicarbonate-rich solution is formed. In the embodiments described above where the bicarbonate rich product is employed as a coolant for the power plant, the bicarbonate rich product production reactor may be co-located with the power plant or an integral part of the power plant.

Precipitation of solid carbonate compositions from BRP, e.g., as described above, results in the production of a composition that includes both precipitated solid carbonate compositions, as well as the remaining liquid from which the precipitated product was produced (i.e., the mother liquor). This composition may be present as a slurry of the precipitate and mother liquor.

This product slurry may be disposed of in some manner following its production. The phrase "disposed of" means that the slurry or a portion thereof, e.g., the solid carbonate composition portion thereof, is either placed at a storage site or employed for a further use in another product, i.e., a manufactured or man-made item, where it is "stored" in that other product at least for the expected lifetime of that other product.

In some instances, this disposal step includes forwarding the slurry composition described above to a long term storage site. The storage site could be an above ground site, a below ground site or an underwater site. In these embodiments, following placement of the slurry at the storage site, the mother liquor component of the slurry may naturally separate from the precipitate, e.g., via evaporation, dispersal, etc.

Where desired, the resultant precipitated product (i.e., solid carbonate composition) may be separated from the resultant mother liquor. Separation of the solid carbonate composition can be achieved using any convenient approach. For example, separation may be achieved by drying the solid carbonate composition to produce a dried solid carbonate composition. Drying protocols of interest include filtering the precipitate from the mother liquor to produce a filtrate and then air drying the filtrate. Where the filtrate is air dried, air drying may be at a temperature ranging from −70 to 120° C., as desired. In some instances, drying may include placing the slurry at a drying site, such as a tailings pond, and allowing the liquid component of the precipitate to evaporate and leave behind the desired dried product. Also of interest are freeze-drying (i.e., lyophilization) protocols, where the solid carbonate composition is frozen, the surrounding pressure is reduced and enough heat is added to allow the frozen water in the material to sublime directly from the frozen precipitate phase to gas. Yet another drying protocol of interest is spray drying, where the liquid containing the precipitate is dried by feeding it through a hot gas, e.g., where the liquid feed is pumped through an atomizer into a main drying chamber and a hot gas is passed as a co-current or counter-current to the atomizer direction.

Where the precipitated product is separated from the mother liquor, the resultant precipitate may be disposed of in a variety of different ways, as further elaborated below. For example, the precipitate may be employed as a component of a building material, as reviewed in greater detail below. Alternatively, the precipitate may be placed at a long term storage site (sometimes referred to in the art as a carbon bank), where the site may be above ground site, a below ground site or an underwater, e.g., deepwater, site.

In certain embodiments, the product carbonate composition is refined (i.e., processed) in some manner prior to subsequent use. Refinement may include a variety of different protocols. In certain embodiments, the product is subjected to mechanical refinement, e.g., grinding, in order to obtain a product with desired physical properties, e.g., particle size, etc. In certain embodiments, the precipitate is combined with a hydraulic cement, e.g., as a supplemental cementitious material, as a sand, a gravel, as an aggregate, etc. In certain embodiments, one or more components may be added to the precipitate, e.g., where the precipitate is to be employed as a cement, e.g., one or more additives, sands, aggregates, supplemental cementitious materials, etc. to produce final product, e.g., concrete or mortar.

In certain embodiments, the carbonate compound is utilized to produce aggregates, e.g., as described in U.S. Pat. No. 7,914,685, the disclosure of which is herein incorporated by reference. In certain embodiments, the carbonate compound precipitate is employed as a component of hydraulic cement. The term "hydraulic cement" is employed in its conventional sense to refer to a composition which sets and hardens after combining with water. Setting and hardening of the product produced by combination of the cements of the invention with an aqueous fluid result from the production of hydrates that are formed from the cement upon reaction with water, where the hydrates are essentially insoluble in water. Such carbonate compound component hydraulic cements, methods for their manufacture and use include, but are not limited to, those described in U.S. Pat. No. 7,735,274; the disclosure of which is herein incorporated by reference.

Also of interest are dissolution precipitation cements like orthopedic calcium phosphate cements that undergo dissolution into solution and precipitate out an alternate material. Dissolution precipitation cements are that are not hydrating however will employ solution as an ion sink which mediates the recrystallization of the lower energy state material which is likened to concrete and can contain volume fillers such as aggregates and finer aggregates.

Also of interest are formed building materials. The formed building materials of the invention may vary greatly. By "formed" is meant shaped, e.g., molded, cast, cut or otherwise produced, into a man-made structure defined physical shape, i.e., configuration. Formed building materials are distinct from amorphous building materials, e.g., particulate (such as powder) compositions that do not have a defined and stable shape, but instead conform to the container in which they are held, e.g., a bag or other container. Illustrative formed building materials include, but are not limited to: bricks; boards; conduits; beams; basins; columns; drywalls etc. Further examples and details regarding formed building materials include those described in United States Published Application No. US20110290156; the disclosure of which is herein incorporated by reference.

Also of interest are non-cementitious manufactured items that include the product of the invention as a component. Non-cementitious manufactured items of the invention may vary greatly. By non-cementitious is meant that the compositions are not hydraulic cements. As such, the compositions are not dried compositions that, when combined with a setting fluid, such as water, set to produce a stable product. Illustrative compositions include, but are not limited to: paper products; polymeric products; lubricants; asphalt products; paints; personal care products, such as cosmetics, toothpastes, deodorants, soaps and shampoos; human ingestible products, including both liquids and solids; agricultural products, such as soil amendment products and animal feeds; etc. Further examples and details non-cementitious manufactured items include those described in U.S. Pat. No. 7,829,053; the disclosure of which is herein incorporated by reference.

In some instances, the solid carbonate product may be employed in albedo enhancing applications. Albedo, i.e., reflection coefficient, refers to the diffuse reflectivity or reflecting power of a surface. It is defined as the ratio of reflected radiation from the surface to incident radiation upon it. Albedo is a dimensionless fraction, and may be expressed as a ratio or a percentage. Albedo is measured on a scale from zero for no reflecting power of a perfectly black surface, to 1 for perfect reflection of a white surface. While albedo depends on the frequency of the radiation, as used herein Albedo is given without reference to a particular wavelength and thus refers to an average across the spectrum of visible light, i.e., from about 380 to about 740 nm.

As the methods of these embodiments are methods of enhancing albedo of a surface, the methods in some instances result in a magnitude of increase in albedo (as compared to a suitable control, e.g., the albedo of the same surface not subjected to methods of invention) that is 0.05 or greater, such as 0.1 or greater, e.g., 0.2 or greater, 0.3 or greater, 0.4 or greater, 0.5 or greater, 0.6 or greater, 0.7 or greater, 0.8 or greater, 0.9 or greater, including 0.95 or greater, including up to 1.0. As such, aspects of the subject methods include increasing albedo of a surface to 0.1 or greater, such as 0.2 or greater, e.g., 0.3 or greater, 0.4 or greater, 0.5 or greater, 0.6 or greater, 0.7 or greater, 0.8 or greater, 0.9 or greater, 0.95 or greater, including 0.975 or greater and up to approximately 1.0.

Aspects of the methods include associating with a surface of interest an amount of a highly reflective microcrystalline or amorphous material composition effective to enhance the albedo of the surface by a desired amount, such as the amounts listed above. The material composition may be associated with the target surface using any convenient protocol. As such, the material composition may be associated with the target surface by incorporating the material into the material of the object having the surface to be modified. For example, where the target surface is the surface of a building material, such as a roof tile or concrete mixture, the material composition may be included in the composition of the material so as to be present on the target surface of the object. Alternatively, the material composition may be positioned on at least a portion of the target surface, e.g., by coating the target surface with the composition. Where the surface is coated with the material composition, the thickness of the resultant coating on the surface may vary, and in some instances may range from 0.1 mm to 25 mm, such as 2 mm to 20 mm and including 5 mm to 10 mm. Applications in use as highly reflective pigments in paints and other coatings like photovoltaic solar panels are also of interest.

The albedo of a variety of surfaces may be enhanced. Surfaces of interest include at least partially facing skyward surfaces of both man-made and naturally occurring objects. Man-made surfaces of interest include, but are not limited to: roads, sidewalks, buildings and components thereof, e.g., roofs and components thereof (roof shingles) and sides, runways, and other man-made structures, e.g., walls, dams, monuments, decorative objects, etc. Naturally occurring surfaces of interest include, but are not limited to: plant surfaces, e.g., as found in both forested and non-forested areas, non-vegetated locations, water, e.g., lake, ocean and sea surfaces, etc.

Methods of using the carbonate precipitate compounds described herein in albedo enhancing applications, as well as compositions produced thereby, are further described in U.S. Provisional Application Ser. No. 61/793,661 filed on Mar. 15, 2013 and U.S. Provisional Application Ser. No. 61/866,985 filed on Aug. 16, 2013; the disclosures of which applications are herein incorporated by reference.

The resultant mother liquor may also be processed as desired. For example, the mother liquor may be returned to the source of the bicarbonated buffer aqueous medium, e.g., ocean, or to another location.

Figure 4:
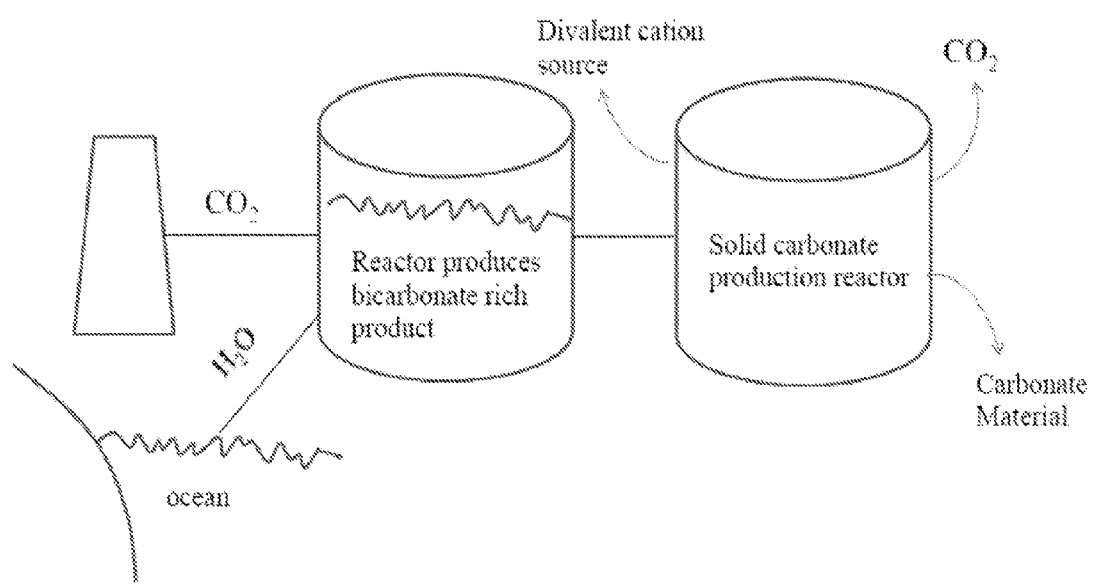
FIG. 4 provides a schematic depiction of the steps of a $CO_2$ sequestration method according to an embodiment of the invention.

The above methodology may be carried out using batch or continuous processing protocols, as desired. For example, a batch protocol may be employed where the bicarbonate rich product is produced in a first reactor configured to contact a $CO_2$ containing gas with an aqueous medium under conditions sufficient to produce a bicarbonate rich product. The product bicarbonate rich product may then be combined with a cation source in a second reactor configured to produce carbonate solids from the bicarbonate rich product, e.g., via precipitation of carbonate solids from the bicarbonate rich product. An example of this type of processing protocol is illustrated in FIG. 4. In FIG. 4, $CO_2$ obtained from a power plant flue stack and water obtained from an ocean are combined in a first reactor under conditions sufficient to produce a bicarbonate rich product, which product may include LCPs, e.g., as described above. The resultant bicarbonate rich product is then combined with a divalent cation source, e.g., a source of $Ca^{2+}$, in a second reactor to produce solid carbonates and pure $CO_2$ gas. The resultant solid carbonates and $CO_2$ gas are then further employed, as desired, e.g., in building materials, etc.

In a continuous process, rather than separating the bicarbonate rich product into a distinct separate containment location, a continuous, unidirectional system with a gradient, where upstream, or the front end, is the $CO_2$ absorption location, with little calcium present, and downstream, or at the rear end, stoichiometric amorphous calcium carbonate (ACC), meaning a $Ca:CO_3$ ratio of 1:1, or the like, such as amorphous magnesium carbonate (AMC) or protodolomite forms in suspension, where calcium is injected in the middle in a continuous punctuated injection process, after the condensed liquid phase forms, may be employed. The advantage to this method is that it does not require a distinct, static separation method, but instead allows the bicarbonate rich product to form and be removed from the immediate absorption in order to maintain the thermodynamic driving force for absorption of $CO_2$ into the solution and production of new bicarbonate rich product, and continue downstream to another location where the cation addition triggers nucleation of the stoichiometric phase of solid carbonate compositions. Removing bicarbonate ion from the bulk solution via the formation of a second phase allows the carbonate ion to bicarbonate ion ratio in the bulk solution to remain high, preserving a higher pH, which favors the thermodynamic driving force for the transition of $CO_2$ (gaseous) to $CO_2$ (dissolved). The rate of transition from $CO_2$ (dissolved) to $HCO_3^-$ (dissolved) can be accelerated by a catalyst, such as carbonic anhydrase, e.g., as described above.

Utility

Methods of invention, e.g., as described above, find use in the sequestration of $CO_2$, i.e., $CO_2$ sequestration. By "$CO_2$ sequestration" is meant the removal or segregation of an amount of $CO_2$ from $CO_2$ containing gas, e.g., a gaseous waste stream produced by an industrial plant, so that at least a portion of the $CO_2$ is no longer present in the $CO_2$ containing gas from which it has been removed. $CO_2$ sequestering methods of the invention sequester $CO_2$, and in some instances produce a storage stable $CO_2$ sequestering product from an amount of $CO_2$, such that the $CO_2$ from which the product is produced is then sequestered in that product. The storage stable $CO_2$ sequestering product is a storage stable composition that incorporates an amount of $CO_2$ into a storage stable form, such as an above-ground storage or underwater storage stable form, so that the $CO_2$ is no longer present as, or available to be, a gas in the atmosphere. As such, sequestering of $CO_2$ according to methods of the invention results in prevention of $CO_2$ gas from entering the atmosphere and allows for long term storage of $CO_2$ in a manner such that $CO_2$ does not become part of the atmosphere. $CO_2$ sequestration is achieved without the addition of alkalinity, via the thermodynamically favorable reaction below.

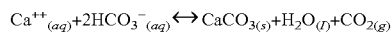

$$Ca^{++}_{(aq)} + 2HCO_3^-_{(aq)} \leftrightarrow CaCO_{3(s)} + H_2O_{(l)} + CO_{2(g)}$$

As such, $CO_2$ sequestration occurs even though base is not added to the system. In embodiments of the invention, $CO_2$ sequestration occurs by sequestering one mol of $CO_2$ in a mineralized carbonate, but releasing one mol of $CO_2$, for every two bicarbonate ions consumed, according to the above equation. This leads to a net removal of $CO_2$ by sequestering one mol of $CO_2$ for every two mols of $CO_2$ converted to bicarbonate, and evolves another mol of $CO_2$. Despite the production of 1 mol of product $CO_2$, 1 mol of $CO_2$ is sequestered for every 2 mols of $CO_2$ removed from the initial $CO_2$ containing gas, resulting a viable and cost-efficient way to sequester $CO_2$. Although the formation of carbonate minerals directly from bicarbonate ions directly produces one mol of $CO_2$ per two mols of $CO_2$ absorbed, it results in a net sequestration of $CO_2$ without the requirement of external alkalinity addition. This result is possible because two $CO_2$ molecules can be absorbed from the gaseous phase to the dissolved phase and form carbonic acid that dissociates to two bicarbonate ions immediately in a bicarbonate buffer. In addition, the product pure $CO_2$ may be employed in other process, e.g., as feedstock, or recycled back into the input gas of the process. As such, aspects of the invention include methods of producing a purified $CO_2$ product from an impure starting material.

Systems

Aspects of the invention further include systems, e.g., small scale devices, processing plants or factories, for removing $CO_2$ from a $CO_2$ containing gas, e.g., by practicing methods as described above. Systems of the invention may have any configuration which enables practice of the particular production method of interest. In some embodiments, systems of the invention include: a source of the $CO_2$ containing gas; a source of an aqueous medium; and a reactor configured to contact the $CO_2$ containing gas with the aqueous medium under conditions sufficient to produce a BRP.

Any convenient bicarbonate buffered aqueous medium source may be included in the system. In certain embodiments, the source includes a structure having an input for aqueous medium, such as a pipe or conduit from an ocean, etc. Where the aqueous medium is seawater, the source may be an input that is in fluid communication with the sea water, e.g., such as where the input is a pipe line or feed from ocean water to a land based system or a inlet port in the hull of ship, e.g., where the system is part of a ship, e.g., in an ocean based system.

The $CO_2$ containing gas source may vary. Examples of $CO_2$ containing gas sources include, but are not limited to, pipes, ducts, or conduits which direct the $CO_2$ containing gas to a portion of the system, e.g., to a reactor configured to produce a bicarbonate rich product, e.g., that includes LCPs. The aqueous medium source and the $CO_2$ containing gas source are connected to a reactor configured to contact the $CO_2$ containing gas with the bicarbonate buffered aqueous medium under conditions sufficient to produce a bicarbonate rich product, such as described above. The reactor may include any of a number of components, such as temperature regulators (e.g., configured to heat the water to a desired temperature), chemical additive components, e.g., for introducing agents that enhance bicarbonate production, mechanical agitation and physical stirring mechanisms. The reactor may include a catalyst that mediates the conversion of $CO_2$ to bicarbonate, such as described above. The reactor may also include components that allow for the monitoring of one or more parameters such as internal reactor pressure, pH, metal-ion concentration, and $pCO_2$.

The reactor further includes an output conveyance for the bicarbonate rich product. In some embodiments, the output conveyance may be configured to transport the bicarbonate rich component to a storage site, such as an injection into subsurface brine reservoirs, a tailings pond for disposal or in a naturally occurring body of water, e.g., ocean, sea, lake, or river. In yet other embodiments, the output may transfer the bicarbonate rich product to a packaging station, e.g., for putting into containers and packaging with a hydraulic cement. Alternatively, the output may convey the bicarbonate rich product to second reactor, which may be configured to produce solid carbonate compositions, i.e., precipitates, from the bicarbonate rich product.

In some instances, the systems include a second reactor configured to further process the bicarbonate rich product, e.g., to dry the product, to combine the product with one or more additional components, e.g., a cement additive, to produce solid carbonate compositions from a bicarbonate rich product, etc. For embodiments where the reactor is configured to produce a carbonate product, such reactors include an input for the bicarbonate rich product, as well as an input for a source of cations (such as described above) which introduces the cations into the bicarbonate rich product in a manner sufficient to cause precipitation of solid carbonate compounds. Where desired, this reactor may be operably coupled to a separator configured to separate a precipitated carbonate mineral composition from a mother liquor, which are produced from the bicarbonate rich product in the reactor. In certain embodiments, the separator may achieve separation of a precipitated carbonate mineral composition from a mother liquor by a mechanical approach, e.g., where bulk excess water is drained from the precipitate by gravity or with the addition of a vacuum, mechanical pressing, filtering the precipitate from the mother liquor to produce a filtrate, centrifugation or by gravitational sedimentation of the precipitate and drainage of the mother liquor. The system may also include a washing station where bulk dewatered precipitate from the separator is washed, e.g., to remove salts and other solutes from the precipitate, prior to drying at the drying station. In some instances, the system further includes a drying station for drying the precipitated carbonate mineral composition produced by the carbonate mineral precipitation station. Depending on the particular drying protocol of the system, the drying station may include a filtration element, freeze drying structure, spray drying structure, etc. as described more fully above. The system may include a conveyer, e.g., duct, from the industrial plant that is connected to the dryer so that a gaseous waste stream (i.e., industrial plant flue gas) may be contacted directly with the wet precipitate in the drying stage. The resultant dried precipitate may undergo further processing, e.g., grinding, milling, in refining station, in order to obtain desired physical properties. One or more components may be added to the precipitate where the precipitate is used as a building material.

The system may further outlet conveyers, e.g., conveyer belt, slurry pump, that allow for the removal of precipitate from one or more of the following: the reactor, drying station, washing station or from the refining station. The product of the precipitation reaction may be disposed of in a number of different ways. The precipitate may be transported to a long term storage site in empty conveyance vehicles, e.g., barges, train cars, trucks, etc., that may include both above ground and underground storage facilities. In other embodiments, the precipitate may be disposed of in an underwater location. Any convenient protocol for transporting the composition to the site of disposal may be employed. In certain embodiments, a pipeline or analogous slurry conveyance structure may be employed, where these approaches may include active pumping, gravitational mediated flow, etc.

In certain embodiments, the system will further include a station for preparing a building material, such as cement, from the precipitate. This station can be configured to produce a variety of cements, aggregates, or cementitious materials from the precipitate, e.g., as described in U.S. Pat. No. 7,735,274; the disclosure of which application is herein incorporated by reference.

Continuous Bicarbonate Rich Product Reactor

In producing bicarbonate rich compositions, e.g., as described above, a carbon dioxide ($CO_2$) source and an aqueous phase may be combined in a continuous bicarbonate rich product (BRP) reactor (which may be a single stage reactor or multi-stage reactor, e.g., as described below) under conditions sufficient to produce a desired BRP composition.

In some instances, the $CO_2$ source and aqueous phase, as well as other desired components, e.g., LCP promoter, catalyst, stabilizer, etc., are introduced into a continuous reactor (which may be single-stage or multi-stage, e.g., as described below), where the reactor conditions are sufficient to produce a BRP composition from the reactants. By "continuous" reactor is meant a reactor that is unidirectional and has an upstream or front end where the $CO_2$ source, aqueous phase and LCP promoter are introduced and a downstream or backend from which the BRP composition is obtained. The continuous reactor may be viewed as a reactor having a gradient, where the upstream, or the front end, has a BRP content which is less than the BRP content at the downstream or backend. As the reactor is a continuous reactor, it is not a batch reactor. As such, it is not a reactor that includes a single vessel which reaches a steady state throughout the composition inside the vessel.

The reactor conditions (which may vary in a multistage reactor from one stage to the next) are sufficient to produce a BRP composition from the input $CO_2$, aqueous phase and LCP promoter. The $CO_2$-containing gas may be contacted with the aqueous phase using any convenient protocol. For example, contact protocols of interest include, but are not limited to: direct contacting protocols, e.g., bubbling the gas through a volume of the aqueous medium, concurrent contacting protocols, i.e., contact between unidirectionally flowing gaseous and liquid phase streams, countercurrent protocols, i.e., contact between oppositely flowing gaseous and liquid phase streams, and the like. Contact may be accomplished through use of infusers, bubblers, fluidic Venturi reactors, spargers, gas filters, sprays, trays, or packed column reactors, and the like, as may be convenient. Where the LCP promoter is distinct from the aqueous phase, the LCP promoter may be combined with the aqueous phase and $CO_2$ source using any convenient protocol. For example, separate sources of each of these components may be separately fed into an upstream location of the reactor. Alternatively, two or more of the components may be combined prior to their introduction into the reactor. For example, the $CO_2$ source and aqueous phase may be combined prior to their introduction into the reactor. Where the aqueous phase is one that includes an LCP promoter, all three of these components will have been combined prior to their introduction into the reactor.

Where desired, the reactor (or at least one of the stages thereof in a multi-stage reactor) may be pressurized. By pressurized is meant the pressure inside the reactor (or at least the portion thereof that is pressurized) is greater than the atmospheric pressure in the location of the reactor. As such, in some instances, the $CO_2$ source; the aqueous phase; and the liquid condensed phase (LCP) promoter are combined under pressure. While the pressure at the pressurized location of the reactor may vary, in some instances the pressure is 50 psi or greater, such as 75 psi or greater, including 100 psi or greater, ranging in some instances from 50 to 500 psi, such as 75 to 250 psi. The temperature in the reactor may vary, and in some instances ranges from 0 to 100° C., such as 20 to 80° C. and including 40 to 70° C. In some instances, the pH of the reactor ranges from 8 to 9, such as 8 to 8.5, including 8.3 to 8.5.

Where desired, reactors may be configured to electrically promote the production and/or stabilization of $CO_2$ sequestering species, e.g., bicarbonates, carbonates, etc. For example, the reactor may include one or more cathodic structures configured to remove $H^+$ from the reactor and thereby promote bicarbonate and/or carbonate formation. In using such reactors, methods may include electrically removing $H^+$ from the contents of the reactor in a manner sufficient to promote production of $CO_2$ sequestering species.

Where desired, an anti-scaling agent may be included in the reactor, e.g., to reduce or inhibit unintentional precipitation in the reactor and/or piping. Any convenient anti-scaling agent may be employed, where such agents include, but are not limited to: descaling chemicals, e.g., aspartic acid, poly aspartic acid, glutamic acid, poly glutamic acid, acrylic acid, polyacrylic acid, hydrochloric acid or the salts of the above mentioned chemicals i.e., aspartate, etc. In some instances, the anti-scaling agent may also function as an LCP promoter, such as described above.

Aspects of the methods include, in some instances, producing a desired BRP composition and a non-BRP composition. By non-BRP composition is meant a composition that is made up of components of the initial input into the reactor, where the components are not present in the final BRP composition. Such components may vary, and may be ions, water, solutes, etc. In such embodiments, the reactor may be configured to separate the components of the reactor into a BRP and non-BRP composition based on one or more characteristics, where such characteristics include, but are not limited to, one or more of: size, charge, viscosity, density, pH, solute composition and the like.

In some instances, separation is accomplished using selective ion separation. In some embodiments, the reactor employed in the methods may include a selective ion separator that is configured to facilitate the selective transport of one or more ions from a first region of the reactor to a second region of the reactor. In this way, the selective ion separator can be used, e.g., to separate unwanted ions from the BRP compositions that are produced in the reactor.

In some embodiments, the selective ion separator is a charge-based ion separator that separates reaction components based on electrical charge. For example, in some embodiments, the selective ion separator comprises a charged material that is disposed near the interior surface of the outer wall of the reactor. The charged material may carry a positive or a negative charge. In some embodiments, the charge-based ion separator carries a positive charge, which attracts anions towards the outer wall of the reactor. The movement of anions towards the outer wall of the reactor results in an increase in the concentration of anions in the region of the reactor near the outer wall, and a corresponding decrease in the concentration of anions in the central region of the reactor.

In some embodiments, the charge-based ion separator comprises a material that carries a negative charge, which repels anions from the outer wall of the reactor. The movement of anions towards the center of the reactor results in an increase in the concentration of anions in the central region of the reactor, and a corresponding decrease in the concentration of anions in the region of the reactor near the outer wall.

Any of a variety of suitable materials may be used for the charge-based ion separator, including but not limited to ion exchange materials, such as ion exchange resins, zeolites, and the like. Examples of ion exchange resins include: strongly acidic resins that include, e.g., sulfonic acid groups, such as sodium polystyrene sulfonate or poly(2-acrylamido-2-methyl-1-propanesulfonic acid); weakly acidic resins that include, e.g., carboxylic acid groups; strongly basic resins that include, e.g., quarternary amino groups, such as trimethly ammonium groups; and weakly basic resins that include, e.g., primary, secondary, and/or tertiary amino groups, such as polyethyleneimine.

In some embodiments, the charge-based ion separator may be disposed in or on a retention structure that is located inside the reactor and is configured to retain the charge-based ion separator. In some embodiments, the retention structure is located near the inner surface of the outer wall of the reactor. In some embodiments, the retention structure extends from the inner surface of the outer wall of the reactor towards the center of the reactor and has an inner wall that defines a retention space between the inner surface of the outer wall of the reactor and the outer surface of the inner wall of the retention structure. In certain embodiments, the inner wall of the retention structure comprises a macroporous layer of material, such as, e.g., a large pore diameter membrane, which allows fluid and molecules to freely pass through the membrane while retaining the charge-based ion separator in the retention space. In such embodiments, the contents of the reactor can freely pass through the inner wall of the retention structure to interact with the charge-based ion separator. In some embodiments, the retention structure may be separate from the reactor, e.g., may be a separate structure that can be placed inside the reactor. In such embodiments, the retention structure and the reactor are generally the same shape, and the dimensions of the retention structure are such that the retention structure can be placed inside the reactor. In some embodiments, the retention structure can be placed inside the reactor and may be removably attached to the reactor.

In certain embodiments, a selective ion separator may be a size-based ion separator that comprises a physical structure that partitions an interior portion of the reactor into at least two distinct regions. In use, the size-based selective ion separator allows an ion to pass from a first region of the reactor, e.g., a region containing a BRP composition, to a second region of the reactor, e.g., a region containing non-BRP compositions or products of the reaction, while preventing other ions and/or molecules from passing through the membrane. In this way, BRP compositions can be separated from unwanted reaction components.

In some embodiments, the size-based ion separator comprises a selective membrane that allows molecules under a certain size to pass through, while preventing larger molecules from passing through. In this way, the size-based ion separator can be used to selectively retain molecules that are over a certain size in a desired region of the reactor. In some embodiments, the selective membrane comprises pores that range in size from 1 micron, up to about 2 microns, up to about 3 microns, up to about 4 microns, up to about 5 microns, up to about 6 microns, up to about 7 microns, up to about 8 microns, up to about 9 microns, or up to about 10 microns or more. In such embodiments, the membrane functions as a simple size exclusion filter that prevents molecules of a certain size from passing through the pores of the membrane.

In some embodiments, the selective membrane may comprise pores ranging in size from about 1 Angstrom, up to about 10 Angstroms, up to about 20 Angstroms, up to about 30 Angstroms, up to about 40 Angstroms, up to about 50 Angstroms, up to about 60 Angstroms, up to about 70 Angstroms, up to about 80 Angstroms, up to about 90 Angstroms, up to about 100 Angstroms, up to about 200 Angstroms, up to about 300 Angstroms, up to about 400 Angstroms, up to about 500 Angstroms, up to about 600 Angstroms, up to about 700 Angstroms, up to about 800 Angstroms, up to about 900 Angstroms or more. In some embodiments, the selective membrane includes a reverse osmosis membrane that has pores ranging in size from about 5 Angstroms, up to about 6 Angstroms, up to about 7 Angstroms, up to about 8 Angstroms. Such membranes are generally impermeable to ions, but allow water molecules to pass through the membrane.

In some embodiments, the selective membrane may comprise a nano-filtration membrane having pores ranging in size from about 1 nanometer up to about 2 nanometers. Such membranes may be used to separate, e.g., $Ca^{2+}$ and $Mg^{2+}$ ions from water by allowing water molecules to pass through the membrane and retaining the $Ca^{2+}$ and $Mg^{2+}$ ions.

In some embodiments, the selective membrane may comprise an ultra-filtration membrane having pores ranging in size from about 10 nanometers, up to about 20 nanometers, up to about 30 nanometers, up to about 40 nanometers, up to about 50 nanometers, up to about 60 nanometers, up to about 70 nanometers, up to about 80 nanometers, up to about 90 nanometers, up to about 100 nanometers, up to about 125 nanometers, up to about 150 nanometers, up to about 175 nanometers, up to about 200 nanometers, or more. Such membranes may be used to separate larger molecules from solutions by retaining the larger molecules on a first side of the membrane while allowing the solution to pass through the membrane.

The subject selective membranes may be disposed on any suitable support structure. For example, in some embodiments, a selective membrane may comprise a layer of material having a desired pore size, as described above, and may be disposed on a support structure, e.g., a macroporous support layer, wherein a solution comprising molecules to be separated by the selective membrane can freely pass through the macroporous support layer.

As discussed above, in some embodiments, a size-based ion separator may be a physical structure that partitions an interior portion of the reactor into at least two distinct regions, each region being separated from the other by the size-based ion separator, e.g., the selective membrane. In some embodiments, a size-based ion separator may be disposed on or in a cartridge component that can be installed in a desired position inside the reactor to partition the reactor into at least two distinct regions. For example, in some embodiments, a size-based ion separator may be configured to be installed inside a reactor to partition the interior of the reactor into at least two distinct regions that are separated by the size-based ion separator.

In some embodiments, the reaction precursors may be introduced into a first region of the partitioned reactor, such that the precursors are present on a first side of the size-based ion separator. As the precursors react inside the reactor, the size-base ion separator may be used to selectively separate various components of the reaction. For example, in some embodiments, non-BRLCP components of the reaction may be selectively transported through, or across, the size-based ion separator, while BRLCP components may be retained on the first side of the size-based ion separator.

In some embodiments, a size-based ion separator may be in the form of a tube-like structure having a first end and a second end. The tube-like structure may be placed inside the reactor such that the first end is fluidly coupled to a port on the first end of the reactor and the second end is fluidly coupled to a port on the second end of the reactor. The walls of the tube-like structure comprise a size-based selective ion separator, such as a membrane. The interior region of the tube-like structure is separated from the rest of the interior of the reactor by the walls of the tube-like structure, and forms a filtration chamber. In some embodiments, reaction precursors may be introduced directly into the interior of the tube-like structure, i.e., into the filtration chamber, where they are reacted to form a BRP composition.

In some embodiments, the subject methods involve separating the BRP compositions from the non-BRP compositions based on differences in electrical charge. For example, BRP entities that are desired in the BRP compositions generally have a neutral electrical charge, and therefore do not interact with other charged molecules. In contrast, entities that are not desired in the BRP compositions may be charged, where such entities may include e.g., chloride ions, sodium ions, potassium ions, etc. As such, charge-based separation techniques can be used to separate the BRP compositions from the non-BRP compositions.

In some embodiments, separation of the BRP compositions from the non-BRP compositions is accomplished by contacting the contents of the reactor with a charged material, such as, e.g., an ion exchange resin, that is disposed within the reactor. In certain embodiments, the charged material is disposed within the retention structure as described above. The reactor contents move freely into the retention structure, where they contact the charged material. In some embodiments, the charged material carries a positive charge, and the non-BRP compositions, such as chloride ions, having a negative charge, associate with the charged material. This leads to a reduction in the concentration of the chloride ions in the central region of the reactor. The BRP compositions, which have a smaller charge, do not associate with the charged material. As a result of the selective interaction between the charged material and the non-BRP compositions, the concentration of the non-BRP compositions in the central region of the reactor decreases, allowing the BRP composition to be separated with higher purity.

In some embodiments, the subject methods involve separating the BRP compositions from the non-BRP compositions based on differences in size. The subject BRP compositions are generally larger in size than the non-BRP compositions, and can therefore be separated using size selection components, such as membranes having a defined pore size.

In some embodiments, the BRP compositions are formed within a filtration chamber in a first region of the reactor. The walls of the filtration chamber comprise a membrane having a defined pore size. A pressure differential is applied across the membrane and the entities of the BRP composition, e.g., the bidentate entities shown in FIG. 3, have a size that is larger than the pores of the membrane, and therefore cannot pass through the membrane. The entities of the non-BRP compositions, in contrast, have a size that is smaller than the pores of the membrane, and therefore freely pass through the membrane. As a result of the pressure differential across the membrane, the concentration of the BRP composition within the filtration chamber is increased, while the concentration of the non-BRP entities within the filtration chamber is decreased. In this way, the BRP composition can be separated from the non-BRP composition with higher purity.

Figure 5:
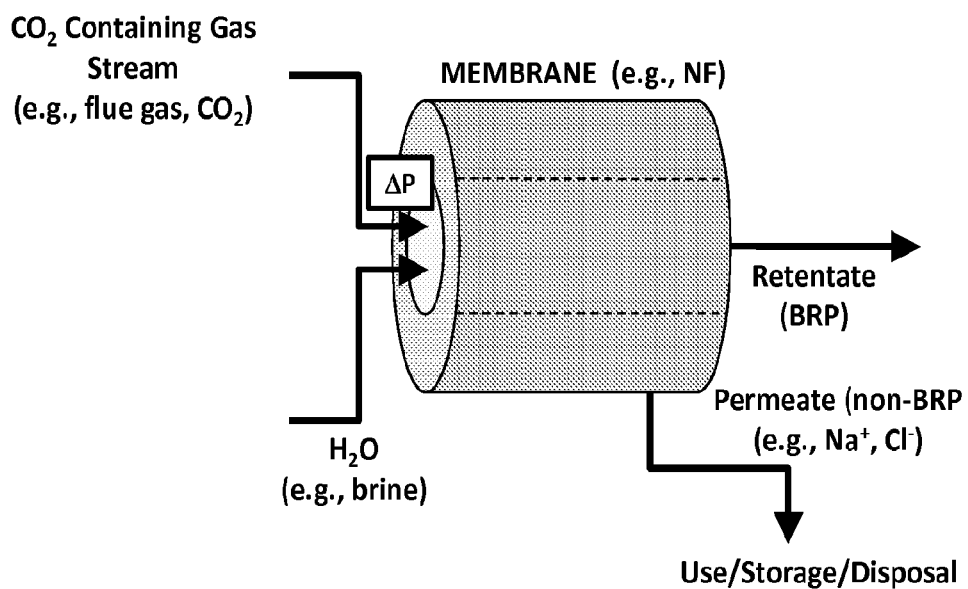
FIG. 5 provides a schematic of a single stage BRLCP reactor in accordance with an embodiment of the invention.

As mentioned above, the reactor employed in methods of the invention may be a single stage reactor or multistage reactor. A schematic of a single stage reactor is shown in FIG. 5. In FIG. 5, a $CO_2$-containing gaseous stream, e.g., flue gas, and an aqueous phase, e.g., brine, are introduced into the front or upstream end of a single stage continuous reactor. The brine further includes an LCP promoter, e.g., in the form of calcium and magnesium ions. Counterions, e.g., chloride ions, are also present. The single stage reactor is configured as a tube that includes an outer wall and an inner tubular size separation, e.g., nanofiltration, membrane. The inside of the reactor is pressurized, e.g., to a pressure ranging from 100 to 250 psi. As the contents of the reactor pass from the front or upstream end to the back or downstream end, BRP compositions form inside of the tubular membrane, and non-BRP entities, such as sodium and chloride ions, pass through the membrane. The desired BRP composition is then separated from the non-BRP entities. The BRP composition is then obtained from the back or downstream end of the reactor.

In some embodiments, a multistage BRP reactor is employed. By multistage is meant that the reactor includes two or more distinct stages, where each downstream stage is in fluid communication with its immediate upstream stage. Different conditions may be present in different stages. For example, different stages may include different separation elements, different catalysts, different BRP promoters, stabilizers, etc. In some embodiments, two different stages are configured to carry out different aspects of the BRP production reaction. For example, in some embodiments, a first reactor is used to form the BRP composition and non-BRP composition from the reaction precursors, and a second reactor is used to separate the non-BRP composition from the BRP composition. In some embodiments, the subject methods involve successively processing the reaction components through a plurality of reactor stages to increase the bicarbonate content of the BRP composition, and/or to remove a greater amount of the non-BRP entities so that the BRP composition can be isolated with high bicarbonate content and/or high purity.

Figure 6:
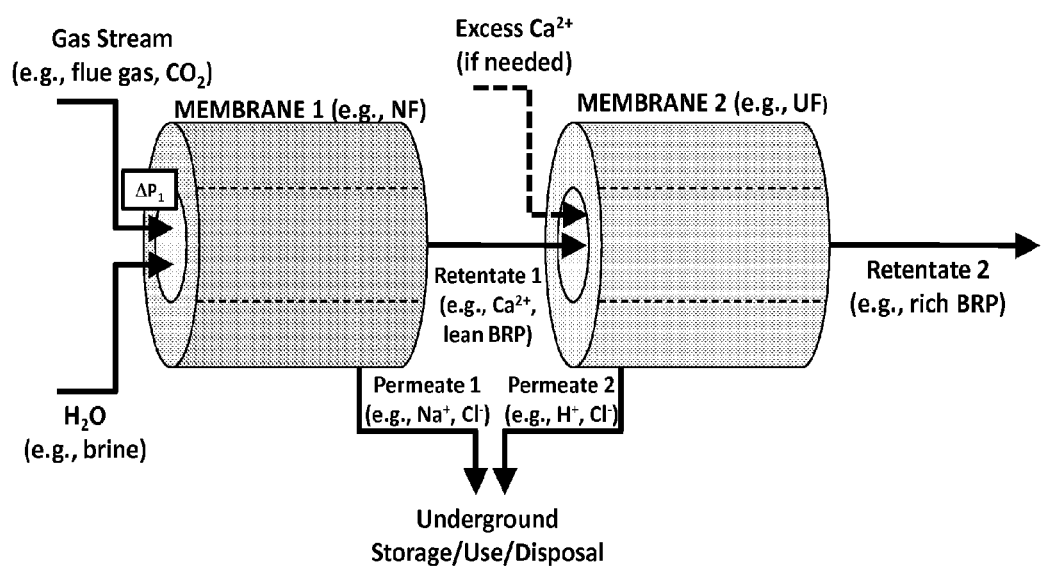
FIG. 6 provides a schematic of a two stage BRLCP reactor in accordance with an embodiment of the invention.

FIG. 6 provides a schematic of a method in accordance with an embodiment of the invention that is carried out in a multistage, and specifically two stage, reactor. In FIG. 6, a $CO_2$-containing gaseous stream, e.g., flue gas, and an aqueous phase, e.g., brine, are introduced into the front or upstream end of the first stage of the two stage continuous reactor. The brine further includes an LCP promoter, e.g., in the form of calcium and magnesium ions. Counterions, e.g., chloride ions, are also present. The first stage of the reactor is configured as a tube that includes an outer wall and an inner tubular size separation, e.g., nanofiltration, membrane. The inside of the reactor is pressurized, e.g., to a pressure ranging from 100 to 250 psi. As the contents of the reactor pass from the front or upstream end to the back or downstream end, a first BRP composition forms inside of the tubular membrane and non-BRP entities, such as sodium and chloride ions, pass through the membrane. The first BRP composition is then introduced into the second stage of the reactor, with optional divalent cation, such as $Ca^{2+}$. The second stage of the reactor is also configured as a tube that includes an outer wall and an inner tubular size separation, e.g., ultrafiltration, membrane. The inside of the reactor is pressurized, e.g., to a pressure ranging from 100 to 250 psi. As the contents of the second stage of the reactor pass from the front or upstream end to the back or downstream end of the second stage of the reactor, a second BRP composition having an LCP droplet content that is higher than the first BRC composition, forms inside of the tubular membrane and non-BRP entities, such as hydrogen and chloride ions, pass through the membrane. The resultant second BRP composition is then obtained from the back or downstream end of the second stage of the reactor.

Figure 7:
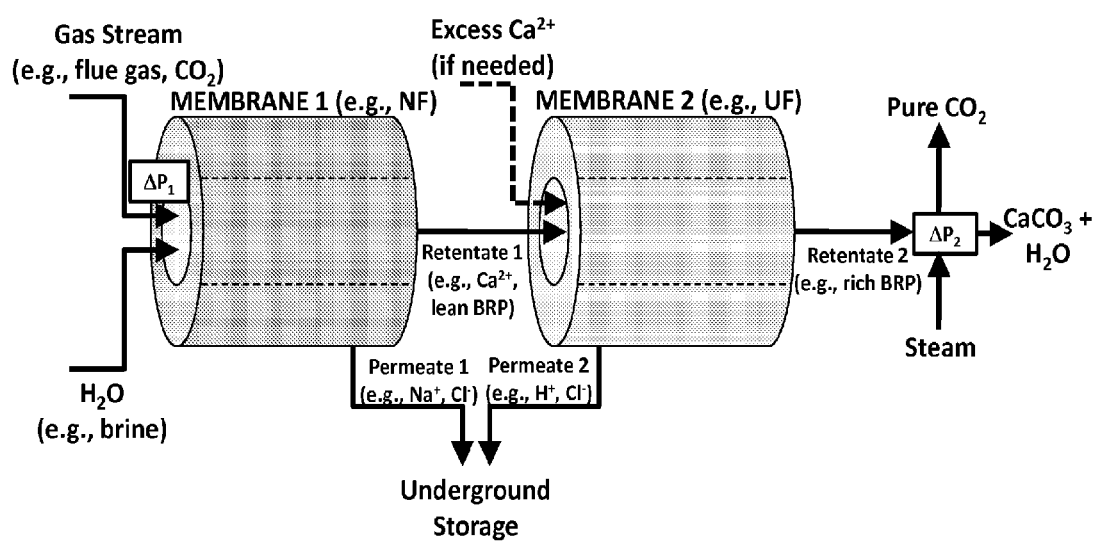
FIG. 7 provides a schematic of a two stage BRLCP reactor where the output of the reactor is further processed to produce a carbonate mineral, in accordance with an embodiment of the invention.

FIG. 7 provides a schematic representation of a method according to embodiments of the invention in which the BRLCP product composition is further employed to produce a carbonate mineral product, e.g., a $CO_2$ sequestering carbonate mineral, such as described above. The method in FIG. 7 includes all of the steps of the method illustrated in FIG. 6. As shown in FIG. 7, the final BRP product composition obtained from the second stage of the reactor is processed to produce a carbonate mineral. In this step, the pressure of the BRP is reduced, e.g., to a value ranging from 200 to 14.8, such as 30 to 14.8 psi. In doing so, calcium carbonate precipitates out of the BRP composition. In addition, pure $CO_2$ is produced, which may be captured, and then stored or used, as desired.

Figure 8:
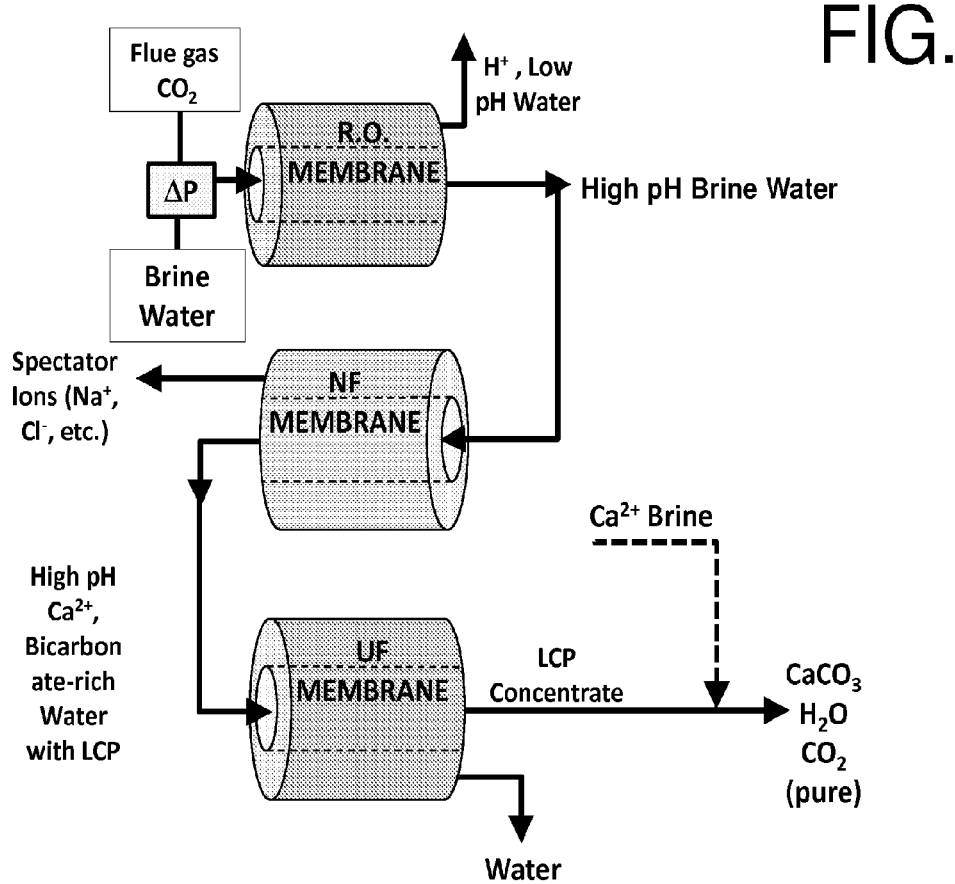
FIG. 8 provides a schematic of a three-stage reactor in accordance with an embodiment of the invention.

FIG. 8 provides a schematic of a three-stage reactor in accordance with an embodiment of the invention. As shown in FIG. 8, a $CO_2$-containing gaseous stream, e.g., flue gas, and an aqueous phase, e.g., brine, are introduced under pressure into the front or upstream end of the first stage of the three stage continuous reactor. The first stage includes an R.O. membrane. The filtrate of the first stage is a low pH liquid. The retentate is a high pH brine. The retentate is then passed to the second stage reactor which includes a N.F. membrane that selectively removes ions, e.g., Na+, Cl−, from the input liquid, to produce a high pH, $Ca^{2+}$, Bicarbonate-rich Water with LCP. This retentate is then passed to the third stage, U.F. membrane reactor, which concentrates the LCP. The final concentrated LCP obtained from the third stage of the reactor is processed to produce a carbonate mineral.

Aspects of the invention include continuous BRP production reactors and systems that include the same. A system is an apparatus that includes a BRP production reactor that is operatively coupled to one or more other functional components, e.g., a carbonate mineral production reactor, etc., as described in greater detail below.

BRP production reactors of interest are reactors that are configured to combine reaction precursors, including, e.g., $CO_2$ gas, aqueous media and one or more liquid condensed phase (LCP) promoters, and to react the precursors to produce a BRP composition. In certain embodiments, the subject BRP production reactors are configured to operate in a continuous production mode, such that the reactors continuously produce a BRP composition from reaction precursors.

The subject BRP production reactors may include at least one elongated structure having a first end and a second end. The elongated structure may be hollow and comprises solid walls that define an interior region of the reactor where the reaction precursors are combined and reacted. The overall length and width of the structure may vary depending on many different variables, such as, e.g., the desired scale of BRP production, the amount and type of reaction precursors used, the particular operating conditions to be employed, and the like. In some embodiments, the length of the BRP production reactor ranges from 1 to 200 ft, such as 20 ft to 80 ft and including 27.1 ft to 31.0 ft. Where the reactor is a multistage reactor, the length of each stage may vary, and in some instances ranges from 2 ft to 400 ft, such as 10 ft to 200 ft and including 54.2 ft to 62.0 ft. The width, e.g., diameter of the BRP production reactor may also vary, and in some embodiments ranges from 1 in. to 120 in., such as 3 in. to 60 in and including 12 in to 24 in. Where the reactor is a multistage reactor, the width of each stage may vary, and in some instances ranges from 2 in. to 240 in., such as 6 in. to 120 in. and including 24 in to 48 in. As such, the volume of the reactor may also vary. In some instances, the total volume of the reactor ranges from 0.02 $ft^3$ to 125 $ft^3$, such as 1 $ft^3$ to 80 $ft^3$ and including 10.9 $ft^3$ to 20.5 $ft^3$. Where the reactor is a multistage reactor, the volume of each stage may vary, and in some instances ranges from 0.04 $ft^3$ to 250 $ft^3$, such as 2 $ft^3$ to 160 $ft^3$ and including 21.8 $ft^3$ to 41.0 $ft^3$.

The cross-sectional shape of the BRP production reactor and stage(s) thereof may vary as well. In some embodiments, the BRP production reactor is generally cylindrical and has a circular cross sectional shape. In other embodiments, a subject reactor may comprise other cross-sectional shapes, including, e.g., elliptical, square and/or rectangular cross-sectional shapes.

The subject reactors are generally constructed from rigid, non-reactive materials that are suitable to contain a BRP production reaction during operation of the reactor. Examples of suitable materials include, but are not limited to, metals and metal alloys (e.g., stainless steel, low carbon alloy steel), ceramics, glass, polymeric components, and the like. In some embodiments, the subject reactors may be constructed from composite materials, such as, e.g., fiber-reinforced polymers, metal composites, ceramic composites, and the like.

The subject BRP production reactors may include a first end and a second end. In some embodiments, the first end is configured to receive various reaction precursors, such as, e.g., $CO_2$-containing gas, aqueous media, and/or other reaction components, such as, e.g., one or more LCP promoters. Accordingly, in some embodiments the first end may include one or more ports that may be used to fluidly connect one or more sources of reaction precursors to the interior of the reactor. For example, in some embodiments the first end of the reactor may comprise one or more ports that may be coupled to various source containers (e.g., via tubing) comprising reaction precursors. In some embodiments, the first end of the reactor may comprise one or more ports that can be coupled to a gas source, e.g., a $CO_2$-containing gas source, so that gas may be introduced into the reactor.

In use, the ports on the first end of the reactor may be used to control the introduction of various reaction precursors into the interior of the reactor, and therefore may be used to control the overall rate of a continuous reaction carried out in the reactor. For example, in some embodiments, the first end of the reactor may comprise various control elements (e.g., valves, metering devices and the like) that may be configured to control the amount of each reaction precursor that is introduced into the reactor, or may be used to control the rate of introduction of each reaction precursor into the interior of the reactor. Accordingly, the input rate of each reaction precursor can be controlled at the first end of the reactor and can therefore be used to control the reaction kinetics within the reactor.

The second end of the reactor is configured to output one or more products of the reaction, such as, e.g., BRP compositions and non-BRP compositions. As such, in certain embodiments the second end of the reactor may include one or more ports that can be used to remove one or more reaction products from the reactor. For example, in some embodiments the second end of the reactor may include a port that can be used to remove a BRP composition from the interior of the reactor. In some embodiments, the second end of the reactor comprises a port that can be used to remove a non-BRP composition from the interior of the reactor.

As described above regarding the first end of the reactor, the ports on the second end of the reactor may include, e.g., control elements that may be used to control the removal of a specified amount of a given reaction product from the reactor, or to control the rate of removal of a given reaction product from the reactor. As such, the output rate of each reaction product can be controlled at the second end of the reactor, and may therefore be used to control the reaction kinetics within the reactor. In some embodiments, the ports on the second end of the reactor may be fluidly coupled to, e.g., one or more containers that are configured to hold the reaction products.

In some embodiments, different reaction products are removed from different areas of the second end of the reactor. For example, in some embodiments, a BRP composition is removed from a central portion of the second end of the reactor, whereas a non-BRP composition is removed from a peripheral portion of the second end of the reactor. Accordingly, in certain embodiments, the second end of the reactor may include a plurality of ports that are located in different areas of the second end of the reactor so as to remove these different reaction components. For example, in some embodiments, the second end of the reactor may comprise one or more ports that are located around the periphery of the second end of the reactor and are used to remove non-BRP compositions from the reactor. The second end of the reactor may also comprise one or more ports that are located at or near the center of the second end of the reactor and are used to remove BRP compositions from the reactor. The spatial positioning and separation of the ports on the second end of the reactor facilitates separate removal of the different reaction products from the reactor.

In some embodiments, the BRP reactor comprises a selective ion separator that is configured to facilitate the selective transport of one or more ions from a first region of the reactor to a second region of the reactor. In this way, the selective ion separator can be used to, e.g., separate unwanted ions from the BRP compositions that are produced in the reactor.

In some embodiments, the selective ion separator is a charge-based ion separator that separates reaction components based on electrical charge. For example, in some embodiments, the selective ion separator comprises a charged material that is disposed near the interior surface of the outer wall of the reactor. The charged material may carry a positive or a negative charge. In some embodiments, the charge-based ion separator carries a positive charge, which attracts anions towards the outer wall of the reactor. The movement of anions towards the outer wall of the reactor results in an increase in the concentration of anions in the region of the reactor near the outer wall, and a corresponding decrease in the concentration of anions in the central region of the reactor.

In some embodiments, the charge-based ion separator comprises a material that carries a negative charge, which repels anions from the outer wall of the reactor. The movement of anions towards the center of the reactor results in an increase in the concentration of anions in the central region of the reactor, and a corresponding decrease in the concentration of anions in the region of the reactor near the outer wall.

Any of a variety of suitable materials may be used for the charge-based ion separator, including but not limited to ion exchange materials, such as ion exchange resins, zeolites, and the like. Examples of ion exchange resins include: strongly acidic resins that include, e.g., sulfonic acid groups, such as sodium polystyrene sulfonate or poly(2-acrylamido-2-methyl-1-propanesulfonic acid); weakly acidic resins that include, e.g., carboxylic acid groups; strongly basic resins that include, e.g., quarternary amino groups, such as trimethyl ammonium groups; and weakly basic resins that include, e.g., primary, secondary, and/or tertiary amino groups, such as polyethyleneimine.

In some embodiments, the charge-based ion separator may be disposed in or on a retention structure that is located inside the reactor and is configured to retain the charge-based ion separator. In some embodiments, the retention structure is located near the inner surface of the outer wall of the reactor. In some embodiments, the retention structure extends from the inner surface of the outer wall of the reactor towards the center of the reactor and has an inner wall that defines a retention space between the inner surface of the outer wall of the reactor and the outer surface of the inner wall of the retention structure. In certain embodiments, the inner wall of the retention structure comprises a macroporous layer of material, such as, e.g., a large pore diameter membrane, which allows fluid and molecules to freely pass through the membrane while retaining the charge-based ion separator in the retention space. In such embodiments, the contents of the reactor can freely pass through the inner wall of the retention structure to interact with the charge-based ion separator. The retention structure may be constructed from any of a variety of suitable materials. Examples of suitable materials include, but are not limited to, metals and metal alloys (e.g., stainless steel, low carbon alloy steel), ceramics, glass, polymeric components, and the like.

In some embodiments, the retention structure may be separate from the reactor, e.g., may be a separate structure that can be placed inside the reactor. In such embodiments, the retention structure and the reactor are generally the same shape, and the dimensions of the retention structure are such that the retention structure can be placed inside the reactor. In some embodiments, the retention structure can be placed inside the reactor and may be removably attached to the reactor.

The dimensions of the retention structure may vary depending on many different variables, such as, e.g., the scale of BRP production, the reaction conditions employed, the mode of operation of the reactor (batch production or continuous production), the type of charge-based ion separator being used, etc. As such, the ratio of the cross sectional area of the retention space to the cross sectional area of the reactor may vary from about 1:100, to about 1:50, to about 1:25, to about 1:20, to about 1:15, to about 1:10, to about 1:5, to about 1:4, to about 1:3, to about 1:2.

In certain embodiments, a selective ion separator may be a size-based ion separator that comprises a physical structure that partitions an interior portion of the reactor into at least two distinct regions. In use, the size-based selective ion separator allows an ion to pass from a first region of the reactor, e.g., a region containing a BRP composition, to a second region of the reactor, e.g., a region containing non-BRP compositions or products of the reaction, while preventing other ions and/or molecules from passing through the membrane. In this way, BRP compositions can be separated from unwanted reaction components.

In some embodiments, the size-based ion separator comprises a selective membrane that allows molecules under a certain size to pass through, while preventing larger molecules from passing through. In this way, the size-based ion separator can be used to selectively retain molecules that are over a certain size in a desired region of the reactor. In some embodiments, the selective membrane comprises pores that range in size from 1 micron, up to about 2 microns, up to about 3 microns, up to about 4 microns, up to about 5 microns, up to about 6 microns, up to about 7 microns, up to about 8 microns, up to about 9 microns, or up to about 10 microns or more. In such embodiments, the membrane functions as a simple size exclusion filter that prevents molecules of a certain size from passing through the pores of the membrane.

In some embodiments, the selective membrane may comprise pores ranging in size from about 1 Angstrom, up to about 10 Angstroms, up to about 20 Angstroms, up to about 30 Angstroms, up to about 40 Angstroms, up to about 50 Angstroms, up to about 60 Angstroms, up to about 70 Angstroms, up to about 80 Angstroms, up to about 90 Angstroms, up to about 100 Angstroms, up to about 200 Angstroms, up to about 300 Angstroms, up to about 400 Angstroms, up to about 500 Angstroms, up to about 600 Angstroms, up to about 700 Angstroms, up to about 800 Angstroms, up to about 900 Angstroms or more. In such embodiments, membrane transport is controlled not only by strict size limits of the membrane's pores, but also by other transport phenomena, including, e.g., the effects of surface charge, double layer formation, Donnan equilibrium, relative mobility of charged species, and the like.

In some embodiments, the selective membrane may comprise a reverse osmosis membrane that has pores ranging in size from about 5 Angstroms, up to about 6 Angstroms, up to about 7 Angstroms, up to about 8 Angstroms. Such membranes are generally impermeable to ions, but allow water molecules to pass through the membrane.

In some embodiments, the selective membrane may comprise a nano-filtration membrane having pores ranging in size from about 1 nanometer up to about 2 nanometers. Such membranes may be used to separate, e.g., $Ca^{2+}$ and $Mg^{2+}$ ions from water by allowing water molecules to pass through the membrane and retaining the $Ca^{2+}$ and $Mg^{2+}$ ions.

In some embodiments, the selective membrane may include an ultra-filtration membrane having pores ranging in size from about 10 nanometers, up to about 20 nanometers, up to about 30 nanometers, up to about 40 nanometers, up to about 50 nanometers, up to about 60 nanometers, up to about 70 nanometers, up to about 80 nanometers, up to about 90 nanometers, up to about 100 nanometers, up to about 125 nanometers, up to about 150 nanometers, up to about 175 nanometers, up to about 200 nanometers, or more. Such membranes may be used to separate larger molecules from solutions by retaining the larger molecules on a first side of the membrane while allowing the solution to pass through the membrane.

The subject selective membranes may be disposed on any suitable support structure. For example, in some embodiments, a selective membrane may comprise a layer of material having a desired pore size, as described above, and may be disposed on a support structure, e.g., a macroporous support layer, wherein a solution comprising molecules to be separated by the selective membrane can freely pass through the macroporous support layer.

As discussed above, in some embodiments, a size-based ion separator may be a physical structure that partitions an interior portion of the reactor into at least two distinct regions, each region being separated from the other by the size-based ion separator, e.g., the selective membrane. In some embodiments, a size-based ion separator may be disposed on or in a cartridge component that can be installed in a desired position inside the reactor to partition the reactor into at least two distinct regions. For example, in some embodiments, a size-based ion separator may be configured to be installed inside a reactor to partition the interior of the reactor into at least two distinct regions that are separated by the size-based ion separator.

In some embodiments, the reaction precursors may be introduced into a first region of the partitioned reactor, such that the precursors are present on a first side of the size-based ion separator. As the precursors react inside the reactor, the size-base ion separator may be used to selectively separate various components of the reaction. For example, in some embodiments, non-BRP components of the reaction may be selectively transported through, or across, the size-based ion separator, while BRP components may be retained on the first side of the size-based ion separator.

In some embodiments, a size-based ion separator may be in the form of a tube-like structure having a first end and a second end. The tube-like structure may be placed inside the reactor such that the first end is fluidly coupled to a port on the first end of the reactor and the second end is fluidly coupled to a port on the second end of the reactor. The walls of the tube-like structure comprise a size-based selective ion separator, such as a membrane. The interior region of the tube-like structure is separated from the rest of the interior of the reactor by the walls of the tube-like structure, and forms a filtration chamber. In some embodiments, reaction precursors may be introduced directly into the interior of the tube-like structure, i.e., into the filtration chamber, where they are reacted to form a BRP composition.

In some embodiments, the reactor includes a pressurizing component that can be used to pressurize at least a portion of the interior of the reactor such that the pressurized portion of the reactor has a pressure that is greater than the pressure of the environment outside the reactor. The operating pressure range of the reactor may vary based on, e.g., the desired scale of BRP production and/or the size of the reactor, and may generally range from about 50 psi, up to about 75 psi, up to about 100 psi, up to about 125 psi, up to about 150 psi, up to about 175 psi, up to about 200 psi, up to about 225 psi, up to about 250 psi, including up to about 500 psi, or more. In some embodiments, the pressure inside the reactor may range from about 5 atm, up to about 6 atm, up to about 7 atm, up to about 8 atm, up to about 9 atm, up to about 10 atm, up to about 11 atm, up to about 12 atm, up to about 13 atm, up to about 14 atm, up to about 15 atm or more.

In some embodiments, the pressurizing component may be used to exert pressure across a selective ion separator that has been placed inside the reactor. For example, in some embodiments, a selective ion separator comprising a membrane may be placed inside the reactor to partition the reactor into at least two distinct regions, and the pressurizing component may be used to exert a pressure differential across the membrane. In some embodiments, pressurized gas, such as, e.g., a pressurized $CO_2$-containing gas, may be used to exert a pressure differential across the membrane.

In some embodiments, a BRP production reactor may include a plurality of stages, as described above (such as a first and second stage, e.g., as illustrated in FIGS. 6 and 7), wherein the individual reactors are connected in series and are in fluid communication with one another. In use, a first reaction can be carried out in the first stage, and one or more products of the first reaction may be passed to a subsequent stage of the reactor for additional processing. In some embodiments, one or more reaction precursor materials may be introduced at each individual stage that is connected in series. For example, additional aqueous media or LCP promoters may be introduced at the first end of each stage. As such, the reaction products of each stage may be further refined by passing through a plurality of individual reactor stages, e.g., to remove non-BRP reaction products, or to further react the BRP reaction products to produce a higher bicarbonate yield.

In certain embodiments, each of the connected stages may be configured to perform different steps of a BRP production reaction. For example, in some embodiments, two or more connected stages may have different dimensions, and/or may include different components, such as, e.g., different ion separators, such as different ion exchange resins and/or different selective membranes, e.g., membranes having different pore sizes. In some embodiments, two of more stages that are connected may be identical. In certain embodiments, two or more stages may be connected in parallel, and the product of each stage may then be fed into a third stage for additional processing. In such embodiments, each of the stages may be identical, or one or more of the stages may be different. Any of a variety of suitable combinations of stages may be used to produce a subject BRP composition.

The number of stages that can be connected in series and/or in parallel may range from 2 or more, up to 3 or more, up to 4 or more, up to 5 or more, up to 10 or more, up to 20 or more, up to 30 or more, up to 40 or more, or up to 50 or more.

Reactors of interest may include a number of additional components, as desired. For example, BRP reactors may include process control equipment, such as, e.g., temperature control systems and/or pH control systems that may be used to control various aspects of the BRP production reaction. For example, in some embodiments, a temperature control system comprising a heating component, such as, e.g., a temperature blanket, a temperature probe, and a temperature control automation system comprising a temperature controller and a processor may be used to maintain the temperature of the contents of the BRP production reactor within a specified temperature range. For example, in some embodiments, a temperature control system may be used to maintain the contents of the BRP reactor at a temperature ranging from 35-40° C. In some embodiments, the temperature control system may be used to shift the temperature of the contents of the BRP reactor from a first temperature to a second temperature. For example, in some embodiments the temperature may be maintained at 35-40° C. for a first period of time, and then shifted to a range of 25-30° C. for a second period of time. In some instances, ion selective electrodes may be included, e.g., to provide the ability to monitor salt concentration changes.

In some embodiments, a pH control system comprising an acid source and a base source, a pH probe, and a pH control automation system comprising a pH controller and a processor may be used to maintain the pH of the contents of the BRP production reactor within a specified pH range. For example, in some embodiments, a pH control system may be used to maintain the contents of the BRP reactor at a pH ranging from 8.0 to 9.0 pH units. In some embodiments, the pH control system may be used to shift the pH of the contents of the BRP reactor from a first pH value to a second pH value. For example, in some embodiments the pH may be maintained at 8.0 to 9.0 pH units for a first period of time, and then shifted to a range of 9.0 to 10.0 pH units for a second period of time.

As summarized above, the BRP reactors may be part of a system that includes additional functional components. For example, the BRP reactors may be operatively coupled to carbonate mineral production reactors, e.g., as described above. BRP reactors may also be coupled to a $CO_2$ generator, e.g., an industrial plant, such as described above.

Additional System Features

The system may be present on land or sea. For example, the system may be a land based system that is in a coastal region, e.g., close to a source of sea water, or even an interior location, where water is piped into the system from a salt water source, e.g., ocean. Alternatively, the system may be a water based system, i.e., a system that is present on or in water. Such a system may be present on a boat, ocean based platform etc., as desired. In certain embodiments, the system may be co-located with an industrial plant, e.g., a power plant, at any convenient location.

The following examples are offered by way of illustration and not by way of limitation.

EXPERIMENTAL

I. Production of Bicarbonate Rich Product with Continuous Reactor

We saturated tap water with $CO_2$ and separated the constituents through both an R.O. and an NF membrane filter. The major constituents of the tap water used in this assay. The presence of ions, it is believed, contributes to the retention of $HCO_3^-$ and the removal of $CO_2$ from the retentate during the membrane filtration process. By using ionic solutions in the membrane filtration process (even the dilute solution used here), unfavorable acidotic components can be removed from the retentate to yield a product that has more useful alkalinity for $CaCO_3$ precipitation chemistry.

|     | $HCO_3^-$ | $H^+$ (pH) | $Na^+$ | $Cl^-$ | $Ca^{2+}$ | $SO_4^{2-}$ |
|-----|-----------|------------|--------|--------|-----------|-------------|
| ppm | 25        | 6.88       | 35     | 45     | 70        | 43          |

We used an AD Seawater R.O element and an An nanofiltration membrane, respectively to conduct the separations. The temperature during the membrane filtrations was between 25° C. and 30° C. We tested 400, 600, and 800 psi $\Delta P$ pressures across the membranes using a pump. We observed that a large pH gradient developed between the permeate (what made it through the filter) and the retentate (what was retained in the flow despite the filter). This shows that acidic components of solution were filtered out into the permeate from the retentate by means of the R.O. and N.F. filters.

Figure 9:
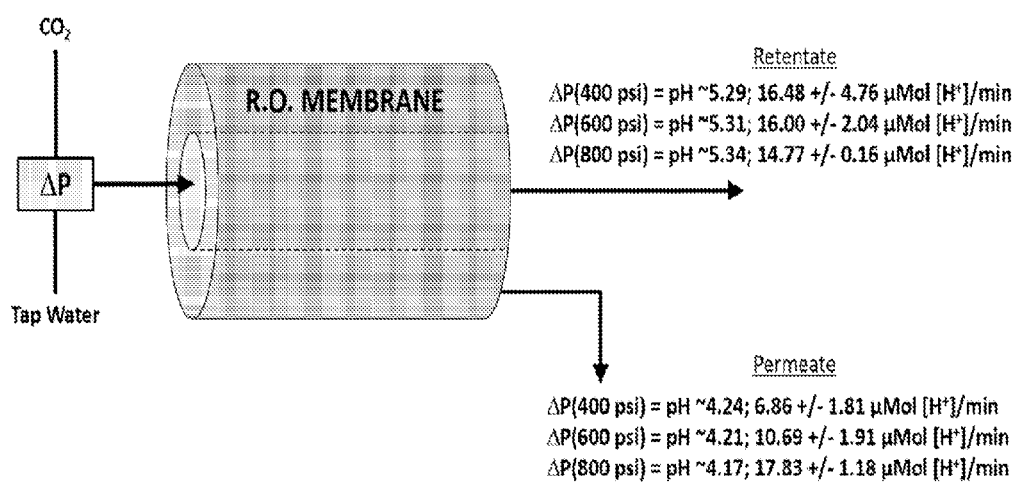
FIGS. 9 and 10 provide schematics of R.O. and N.F. filtration membrane reactors employed in the Experimental section, below.

FIG. 9 provides a schematic of the R.O. reactor. As shown in FIG. 9, the retentate is consistently and increasingly more basic than the permeate with increasing pump pressure ($\Delta P$). Several R.O. membranes in parallel and/or in series may be used to increase the pH of the retentate to aid in the $CO_2$ sequestration process. The data was collected in triplicate (n=3) for each condition (400, 600, 800 psi).

Figure 10:
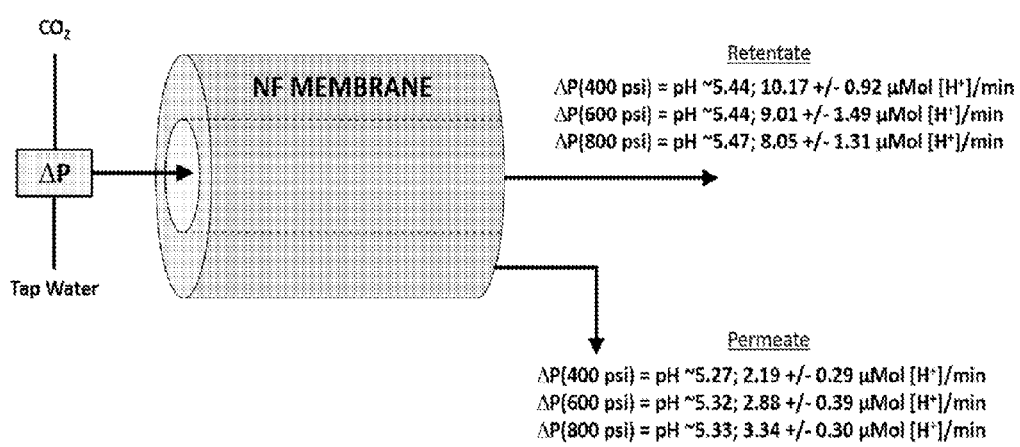

FIG. 10 provides a schematic of the N.F. reactor. The retentate is consistently and increasingly more basic than the permeate with increasing pump pressure ($\Delta P$). With respect to the removal of acidic components of the retentate, the N.F. membrane did not perform as well as the R.O. membrane but nonetheless may be very instrumental due to its ability to simultaneously remove certain, undesirable ions. The data was collected in triplicate for each condition (400, 600, 800 psi).

Figure 11:
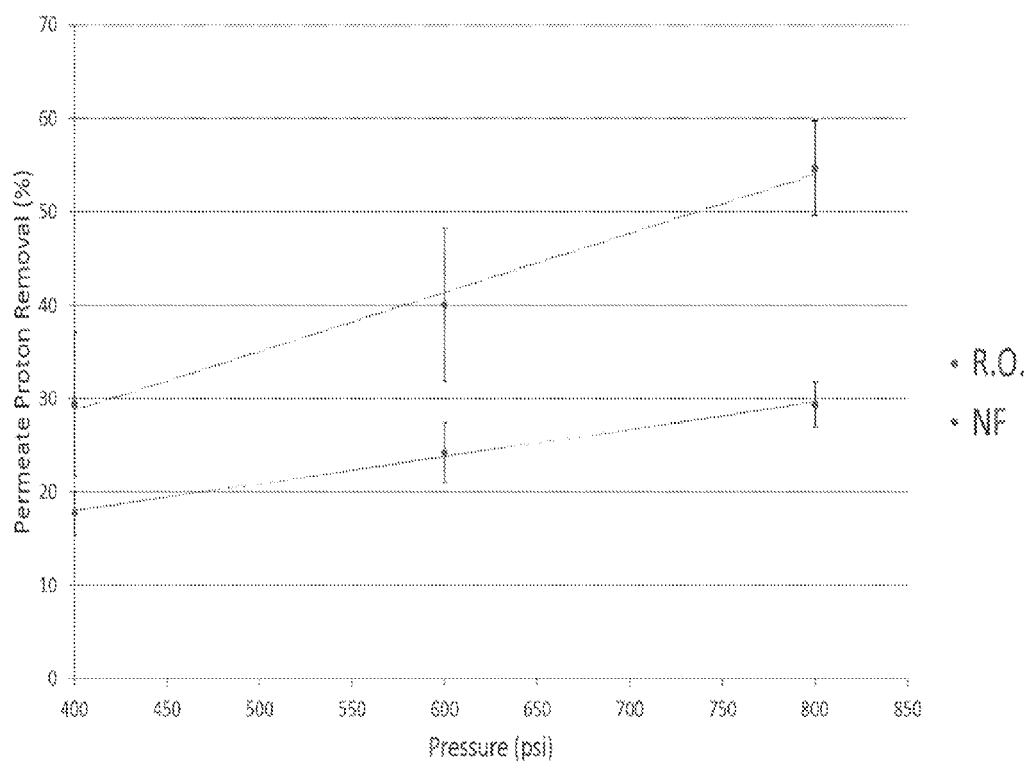
FIG. 11 provides a graph of the results of a bicarbonate rich product production protocol as reported in the Experimental section, below.

FIG. 11 provides the fraction (in percent) of protons removed by the permeate from the retentate during membrane filtration at various pump pressures ($\Delta P$) as calculated by pH and flow rate. The R.O. filter is very efficient at removing the acidic components from the solution yielding a retentate that is more useful for $CaCO_3$ precipitation. The NF membrane filter is successful to a lesser degree but is simultaneously helpful in removing unwanted "spectator ions" from our solutions such as $Na^+$ and $Cl^-$. The efficiency of proton removal from the retentate increases with increasing ($\Delta P$) which is a principle that can be employed, as desired. The breadth of the error bars are two standard deviations as measured with N=3.

The above protocol produced a bicarbonate rich product characterized by the presence of liquid condensed phase (LCP) droplets. The LCP droplets are rich in $Ca^{2+}$ and bicarbonate ions, giving the LCP hard water character. Strategies may be employed to manipulate the LCP that are similar to strategies to manage hard water. The addition or removal of NaCl (aq) is one such strategy which can be easily achieved by use of R.O., NF, and UF filters. The addition of NaCl may also be used to add "softness" to the process waters for manipulation of the LCP. Another technique used to manage hard water, which can be used to manage the "hard water" LCP droplets, is the addition of additives, such as polymeric or proteinaceous additives, e.g., polyaspartic acid (see Gower et al. among others). These additives include poly amino acids, sugars, proteins, surfactants, micelles, and liposomes. These additives may be positively or negatively charged, they may be hydrophilic or hydrophobic (or even amphiphilic).

II. BRP Admixtures

Figure 12:
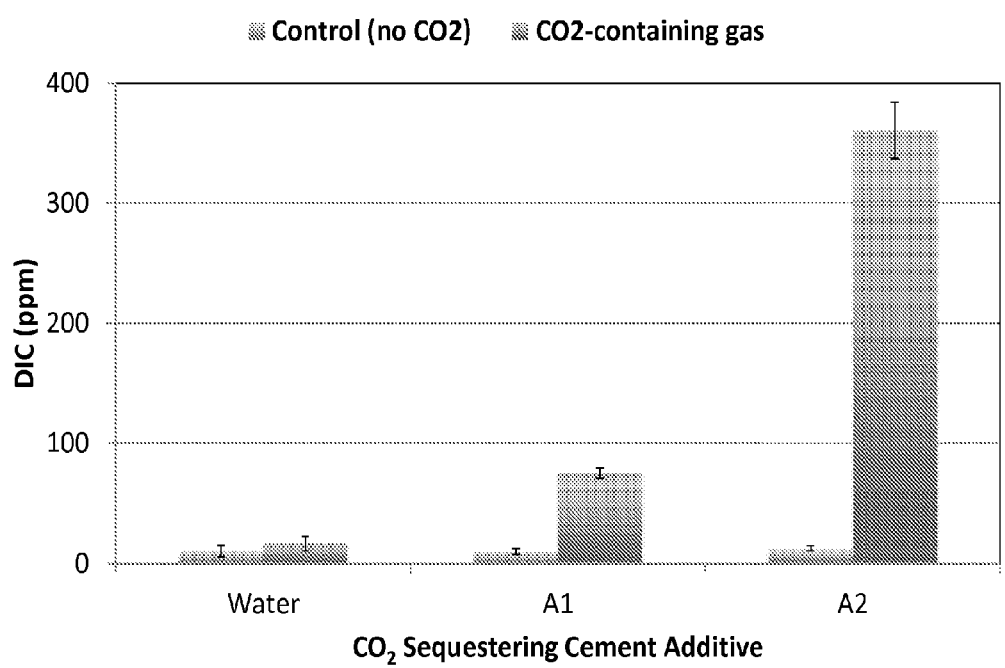
FIG. 12 compares the amount of dissolved inorganic carbon (DIC) in three different samples: water, a first $CO_2$ sequestering cement additive 1 (A1) and a second $CO_2$ sequestering cement additive 2 (A2).

Example A: Preparation of a $CO_2$ Sequestering Cement Additive from a High Early-Strength (Type C, Type E), Superplasticizing (Type A, Type F) Commercial Admixture A $CO_2$ sequestering cement additive, A1, is prepared with a commercial admixture that is composed of polycarboxylate (15-40 wt %), sodium thiocyanate (15-40 wt %), N,N,N',N'-tetrakis(2-hydroxyethyl)ethylenediamine (5-10 wt %), triethanolamine (1-5 wt %) and water. The concentrated admixture is diluted to an appropriate volume with aqueous medium (e.g. 0.02 L admixture in 1.0 L water) to obtain the recommended dilution appropriate to produce a settable cementitious composition. A $CO_2$-containing gas is then dissolved into the solution to form a BRLCP component, of which, the amount of dissolved inorganic carbon (DIC) in solution is quantified with a UIC CM150 series carbon analyzer. The data are summarized in FIG. 12 and Table 1. For this example, A1 demonstrates a 650% increase in DIC upon treatment with a $CO_2$-containing gas, compared to the A1 control, which is not treated with a $CO_2$-containing gas.

Following formation of the BRLCP component, the $CO_2$ sequestering cement additive can be combined with an appropriate amount of a cement to produce a settable cementitious composition (e.g. 0.3-1.0 L A1 per 100 kg cement).

Example B: Preparation of a $CO_2$ Sequestering Cement Additive from a Water-Reducing Accelerator (Type C, Type E) Commercial Admixture A $CO_2$ sequestering cement additive, A2, is prepared with a commercial admixture that is composed of calcium nitrate (15-40 w %), sodium thiocyanate (10-30 wt %), diethanolamine (10-30 wt %), triethanolamine (3-7 wt %) and water. The concentrated admixture is diluted to an appropriate volume with aqueous medium (e.g. 0.06 L admixture in 1.0 L water) to obtain the recommended dilution appropriate to produce a settable cementitious composition. A $CO_2$-containing gas is then dissolved into the solution to form a BRLCP component, of which, the amount of DIC in solution is quantified with a UIC CM150 series carbon analyzer. The data are summarized in FIG. 12 and Table 1. For this example, A2 demonstrates a 2,670% increase in DIC upon treatment with a $CO_2$-containing gas, compared to the A2 control, which is not treated with a $CO_2$-containing gas. The $CO_2$ sequestering cement additive A2 is sequestering $CO_2$—or at least a portion of it—in the form of a solid material, as opposed to $CO_2$ sequestering cement additive A1, which is sequestering $CO_2$ in the form of a BRLCP. See also Example D below.

TABLE 1

| Cement Additive | pH before $CO_2$ addition | pH after $CO_2$ addition | DIC before (ppm) | DIC after (ppm) | % change in DIC |
|---|---|---|---|---|---|
| Water | 7.2 | 4.4 | 10 ± 5 | 17 ± 6 | 70% increase |
| A1 | 8.7 | 5.2 | 10 ± 3 | 75 ± 4 | 650% increase |
| A2 | 9.9 | 5.8 | 13 ± 2 | 360 ± 24 | 2,670% increase |

Figure 13:
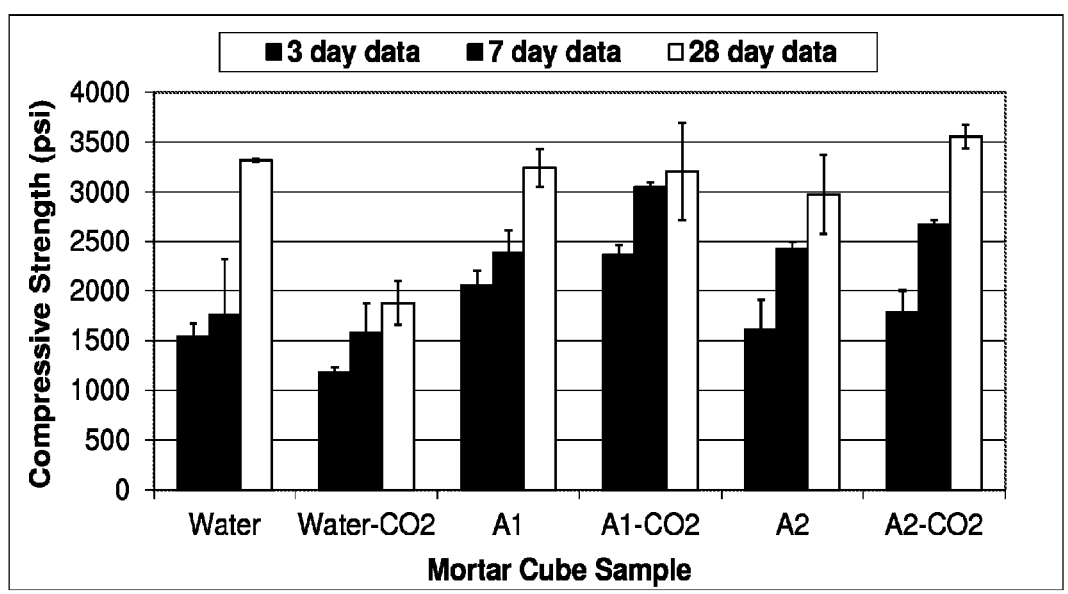
FIG. 13 compares the compressive strength of mortar cube samples made with and without (control) admixtures containing a sequestered $CO_2$ component. The data represent 3-, 7- and 28-day tests for mortar cubes made with water, $CO_2$ sequestering cement additive 1 (A1) and $CO_2$ sequestering cement additive 2 (A2).

Example C: Preparation of Mortar Cubes Using $CO_2$ Sequestering Cement Additive Mortar cubes are made by mixing mortar with $CO_2$ sequestering cement additive in the ratio of 0.138 parts (e.g. 0.138 L A1 per kg mortar) in an attempt to adhere to ASTM C109 standard. Control cubes are made with mixing water that has not been exposed to a $CO_2$-containing gas prior to mixing with mortar. The 3- and 7-day strength tests for the series of mortar cubes made in this example are shown in FIG. 13. For each set of cubes, the cubes that were made by mixing with $CO_2$ sequestering cement additive show higher compressive strength for both the 3-, 7- and 28-day tests. As can be seen in the results, higher compressive strength is achieved with admixtures that include a $CO_2$ sequestering component.

Example D: Preparation of a Solid Carbonate Material from a Solution of $CO_2$ Sequestering Cement Additive A solid carbonate material is prepared from addition of a $CO_2$-containing gas to a concentrated, homogeneous solution of commercial admixture that is composed of calcium nitrate (15-40 w %), sodium thiocyanate (10-30 wt %), diethanolamine (10-30 wt %), triethanolamine (3-7 wt %) and water (e.g. $CO_2$ sequestering cement additive A2, described in Example B).

Prior to the addition of the $CO_2$-containing gas, the pH of the admixture solution is 10.5. The $CO_2$-containing gas is added in successive bursts, at pressures less than 200 psi (less than 14 atm), to form a BRLCP component (e.g., as in Example B), such that the pH of the solution changes to pH 9.2 after one burst, pH 8.3 after two bursts, and pH 4.9 after greater than three bursts resulting in the concomitant formation of a thick slurry.

The solid material is isolated from the thick slurry by decanting off the remaining liquid admixture. The solid material is rinsed a number of times with water, decanting off the liquid after each rinse, and placed in an oven to dry.

Figure 14:
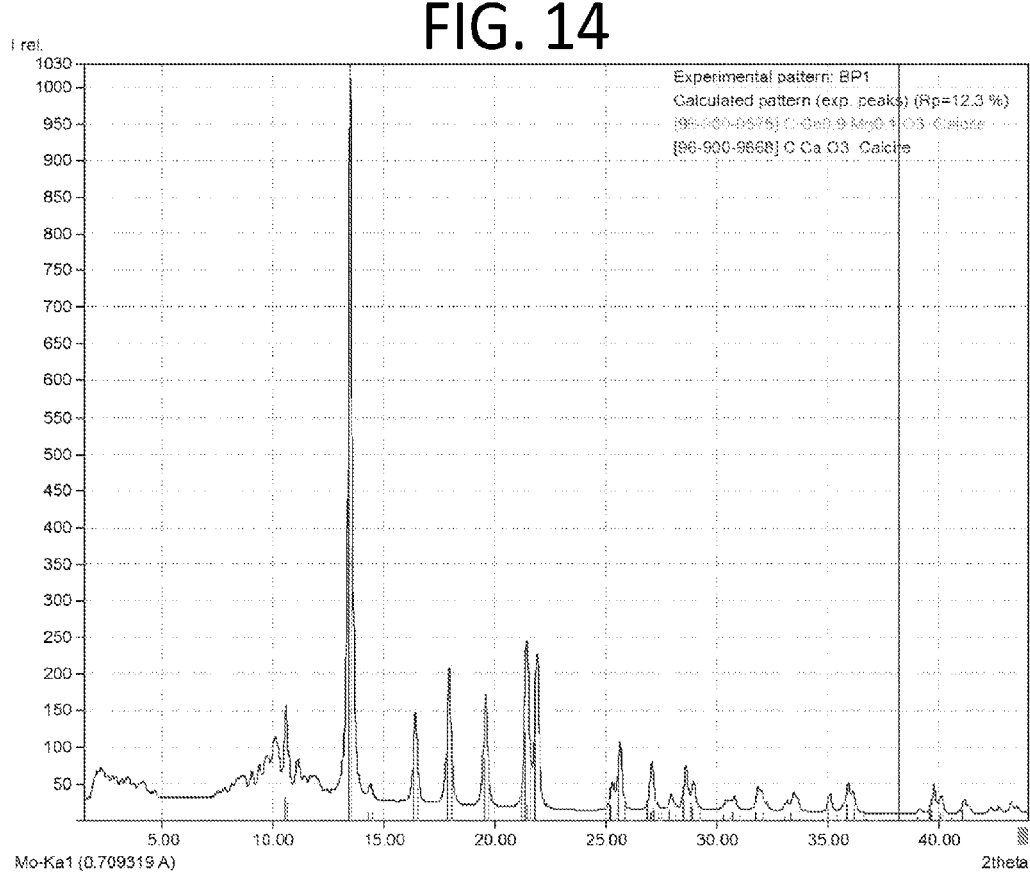
FIG. 14 shows the X-ray diffraction pattern of the solid material prepared by addition of a $CO_2$-containing gas to an aqueous solution of $CO_2$ sequestering cement additive 2 (A2).

Two tests confirm the dried, isolated solid is indeed calcium carbonate: (i) addition of 1.2 M hydrochloric acid to the solid material results in vigorous effervescence and (ii) X-ray diffraction (XRD) analysis indicates the solid material is calcite, the pattern of which is shown in FIG. 14.

Example E: Preparation of a $CO_2$ Sequestering Cement Additive Comprising MDEA and L-Arginine A $CO_2$ sequestering cement additive is prepared by combining 1 wt % MDEA and 4 wt % L-Arginine. These components make up 5 wt % of the $CO_2$ sequestering cement additive, and are capable of incorporating 1.38 wt % $CO_2$ in solution. A $CO_2$ sequestering cement additive is produced using these components dissolved in an appropriate volume of aqueous medium (e.g. water) to produce a final volume of 36 gallons. A $CO_2$-containing gas is then dissolved into the solution. The dissolved $CO_2$ reacts with the MDEA and L-Arginine to form a BRLCP component, and 1.38 wt % of $CO_2$ is incorporated into the BRLCP component. Following formation of the BRLCP component, the $CO_2$ sequestering cement additive can be combined with an appropriate amount of a cement to produce a settable cementitious composition. When one gallon of this $CO_2$ sequestering cement additive is combined with an appropriate amount of a cement and an additional setting fluid (e.g., 35 gallons of water) to produce one yard of a settable cementitious composition, the settable cementitious composition sequesters 0.12 lbs of $CO_2$. When 36 gallons of this $CO_2$ sequestering cement additive is combined with an appropriate amount of a cement to produce one yard of a settable cementitious composition, the settable cementitious composition sequesters 4.17 lbs of $CO_2$. The composition of this $CO_2$ sequestering cement additive is summarized in Table 2.

TABLE 2

| Amine Component | Wt % in additive | Equivalent wt % $CO_2$ in additive | lbs $CO_2$ sequestered per gallon of additive used in cementitious composition | lbs $CO_2$ sequestered per yard of cementitious composition when 36 gallons of additive used |
|---|---|---|---|---|
| MDEA | 1 | 0.37 | 0.03 | 1.12 |
| L-Arginine | 4 | 1.01 | 0.08 | 3.06 |
| Total | 5 | 1.38 | 0.12 | 4.17 |

Example F: Preparation of a $CO_2$ Sequestering Cement Additive Comprising TEOA, L-Arginine and Choline Chloride A $CO_2$ sequestering cement additive is prepared by combining 8 wt % triethanolamine (TEOA), 12 wt % L-Arginine and 5 wt % choline chloride. These components make up 25 wt % of the $CO_2$ sequestering cement additive, and are capable of incorporating 6.97 wt % $CO_2$ in solution. A $CO_2$ sequestering cement additive is produced using these components dissolved in an appropriate volume of aqueous medium (e.g., water) to produce a final volume of 36 gallons. A $CO_2$-containing gas is then dissolved into the solution. The dissolved $CO_2$ reacts with the TEOA, L-Arginine and choline chloride to form a BRLCP component, and 6.97 wt % of $CO_2$ is incorporated into the BRLCP component. Following formation of the BRLCP component, the $CO_2$ sequestering cement additive can be combined with an appropriate amount of a cement to produce a settable cementitious composition. When one gallon of this $CO_2$ sequestering cement additive is combined with an appropriate amount of a cement and an additional setting fluid (e.g., 35 gallons of water) to produce one yard of a settable cementitious composition, the settable cementitious composition sequesters 0.59 lbs of $CO_2$. When 36 gallons of this $CO_2$ sequestering cement additive is combined with an appropriate amount of a cement to produce one yard of a settable cementitious composition, the settable cementitious composition sequesters 21.1 lbs of $CO_2$. The composition of this $CO_2$ sequestering cement additive is summarized in Table 3.

TABLE 3

| Amine Component | Wt % in additive | Equivalent wt % $CO_2$ in additive | lbs $CO_2$ sequestered per gallon of additive used in cementitious composition | lbs $CO_2$ sequestered per yard of cementitious composition when 36 gallons of additive used |
|---|---|---|---|---|
| TEOA | 8 | 2.36 | 0.20 | 7.14 |
| Choline Chloride | 5 | 1.58 | 0.13 | 4.77 |
| L-Arginine | 12 | 3.03 | 0.25 | 9.17 |
| Total | 25 | 6.97 | 0.59 | 21.1 |

Example G: Preparation of a $CO_2$ Sequestering Cement Additive Comprising DEA, TEOA and L-Arginine A $CO_2$ sequestering cement additive is prepared by combining 7 wt % triethanolamine (TEOA), 8 wt % L-Arginine and 10 wt % diethanolamine (DEA). These components make up 25 wt % of the $CO_2$ sequestering cement additive, and are capable of incorporating 6.18 wt % $CO_2$ in solution. A $CO_2$ sequestering cement additive is produced using these components dissolved in an appropriate volume of aqueous medium (e.g. water) to produce a final volume of 36 gallons. A $CO_2$-containing gas is then dissolved into the solution. The dissolved $CO_2$ reacts with the TEOA, L-Arginine and DEA to form a BRLCP component, and 6.18 wt % of $CO_2$ is incorporated into the BRLCP component. Following formation of the BRLCP component, the $CO_2$ sequestering cement additive can be combined with an appropriate amount of a cement to produce a settable cementitious composition. When one gallon of this $CO_2$ sequestering cement additive is combined with an appropriate amount of a cement and an additional setting fluid (e.g., 35 gallons of water) to produce one yard of a settable cementitious composition, the settable cementitious composition sequesters 0.52 lbs of $CO_2$. When 36 gallons of this $CO_2$ sequestering cement additive is combined with an appropriate amount of a cement to produce one yard of a settable cementitious composition, the settable cementitious composition sequesters 18.7 lbs of $CO_2$. The composition of this $CO_2$ sequestering cement additive is summarized in Table 4.

TABLE 4

| Amine Component | Wt % in additive | Equivalent wt % $CO_2$ in additive | lbs $CO_2$ sequestered per gallon of additive used in cementitious composition | lbs $CO_2$ sequestered per yard of cementitious composition when 36 gallons of additive used |
|---|---|---|---|---|
| DEA | 10 | 2.09 | 0.18 | 6.33 |
| TEOA | 7 | 2.06 | 0.17 | 6.24 |
| L-Arginine | 8 | 2.02 | 0.17 | 6.11 |
| Total | 25 | 6.18 | 0.52 | 18.7 |

Example H: Preparation of a $CO_2$ Sequestering Cement Additive Comprising THEED, Tysol SM, TEOA Acetate, and Choline Chloride A $CO_2$ sequestering cement additive is prepared by combining 5 wt % THEED, 10 wt % Tysol SM, 30 wt % TEOA acetate, and 30 wt % choline chloride. These components make up 75 wt % of the $CO_2$ sequestering cement additive, and are capable of incorporating 18.4 wt % $CO_2$ in solution. A $CO_2$ sequestering cement additive is produced using these components dissolved in an appropriate volume of aqueous medium (e.g. water) to produce a final volume of 36 gallons. A $CO_2$-containing gas is then dissolved into the solution. The dissolved $CO_2$ reacts with the THEED, Tysol SM, TEOA and choline chloride to form a BRLCP component. Due to the slower nature of reaction between $CO_2$ and tertiary amines, the solution is stored for a period of time, ranging from between 2 to 5 days, between 1 to 7 weeks, or between 2 to 4 months to allow the dissolved $CO_2$ to react with water prior to reacting with the amines to form a BRLCP component.

Following formation of the BRLCP component, the $CO_2$ sequestering cement additive can be combined with an appropriate amount of a cement to produce a settable cementitious composition. When one gallon of this $CO_2$ sequestering cement additive is combined with an appropriate amount of a cement and an additional setting fluid (e.g., 35 gallons of water) to produce one yard of a settable cementitious composition, the settable cementitious composition sequesters 1.54 lbs of $CO_2$. When 36 gallons of this $CO_2$ sequestering cement additive is combined with an appropriate amount of a cement to produce one yard of a settable cementitious composition, the settable cementitious composition sequesters 55.6 lbs of $CO_2$. The composition of this $CO_2$ sequestering cement additive is summarized in Table 5.

TABLE 5

| Amine Component | Wt % in additive | Equivalent wt % $CO_2$ in additive | lbs $CO_2$ sequestered per gallon of additive used in cementitious composition | lbs $CO_2$ sequestered per yard of cementitious composition when 36 gallons of additive used |
|---|---|---|---|---|
| THEED | 5 | 0.93 | 0.08 | 2.82 |
| Tysol SM | 10 | 1.69 | 0.14 | 5.11 |
| TEOA acetate | 30 | 6.31 | 0.53 | 19.1 |
| Choline Chloride | 30 | 9.46 | 0.79 | 28.6 |
| Total | 75 | 18.4 | 1.54 | 55.6 |

Example I: Preparation of a $CO_2$ Sequestering Cement Additive Comprising MDEA, Choline Chloride and Ammonium Chloride as Well as Rice Husk Ash A $CO_2$ sequestering cement additive is prepared by combining 10 wt % MDEA, 10 wt % choline chloride and 5 wt % ammonium chloride. These components make up 25 wt % of the $CO_2$ sequestering cement additive, and are capable of incorporating 10.9 wt % $CO_2$ in solution. Rice husk ash, a pozzolan that is composed of pure silica in non-crystalline form, is suspended in the solution in order to provide thermal stabilization to the mixture. A $CO_2$ sequestering cement additive is produced using these components dissolved in an appropriate volume of aqueous medium (e.g. water) to produce a final volume of 36 gallons. A $CO_2$-containing gas is then dissolved into the solution. The dissolved $CO_2$ reacts with the MDEA, choline chloride and ammonium chloride to form a BRLCP component, and 10.9 wt % of $CO_2$ is incorporated into the BRLCP component. Following formation of the BRLCP component, the $CO_2$ sequestering cement additive can be combined with an appropriate amount of a cement to produce a settable cementitious composition. When one gallon of this $CO_2$ sequestering cement additive is combined with an appropriate amount of a cement and an additional setting fluid (e.g., 35 gallons of water) to produce one yard of a settable cementitious composition, the settable cementitious composition sequesters 0.92 lbs of $CO_2$. When 36 gallons of this $CO_2$ sequestering cement additive is combined with an appropriate amount of a cement to produce one yard of a settable cementitious composition, the settable cementitious composition sequesters 33.1 lbs of $CO_2$. The composition of this $CO_2$ sequestering cement additive is summarized in Table 6.

TABLE 6

| Amine Component | Wt % in additive | Equivalent wt % $CO_2$ in additive | lbs $CO_2$ sequestered per gallon of additive used in cementitious composition | lbs $CO_2$ sequestered per yard of cementitious composition when 36 gallons of additive used |
|---|---|---|---|---|
| MDEA | 10 | 3.69 | 0.31 | 11.2 |
| Choline Chloride | 10 | 3.15 | 0.26 | 9.53 |
| Ammonium Chloride | 5 | 4.11 | 0.35 | 12.4 |
| Total | 25 | 10.9 | 0.92 | 33.1 |

While the above systems have been described in terms of component parts, the systems may be configured for batch or continuous reactions, e.g., as described above in the methods section. For example, systems may be configured to perform the batch reaction embodiments of the methods, e.g., where a bicarbonate rich product is produced in a first reactor, and then subjected to precipitation conditions in a second reactor. Alternatively, the systems may be configured for continuous embodiments of the methods, e.g., where bicarbonate rich product is produced in a first portion of a single reactor and then subjected to precipitation conditions in a second portion of the same reactor, such as described above.

Example III

Figure 15A:
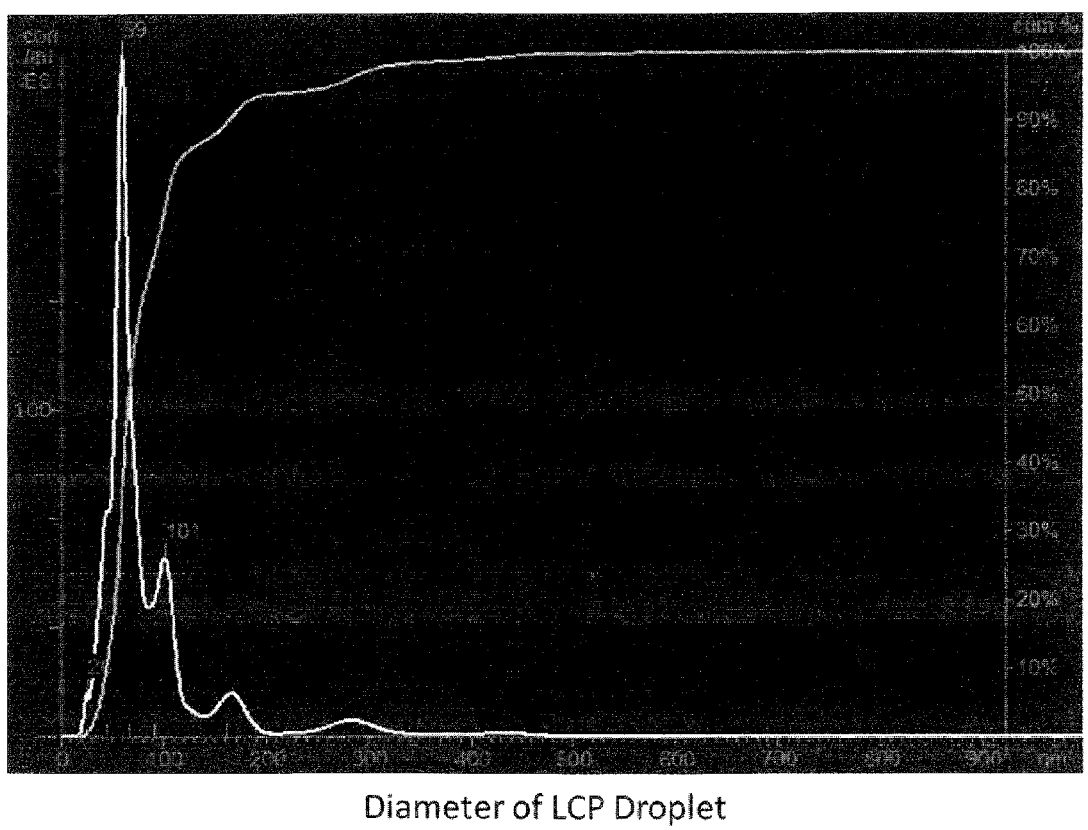
FIGS. 15A and 15B provide graphical results of LCP droplet characteristics produced in Example III of the Experimental section, below.
Figure 15B:
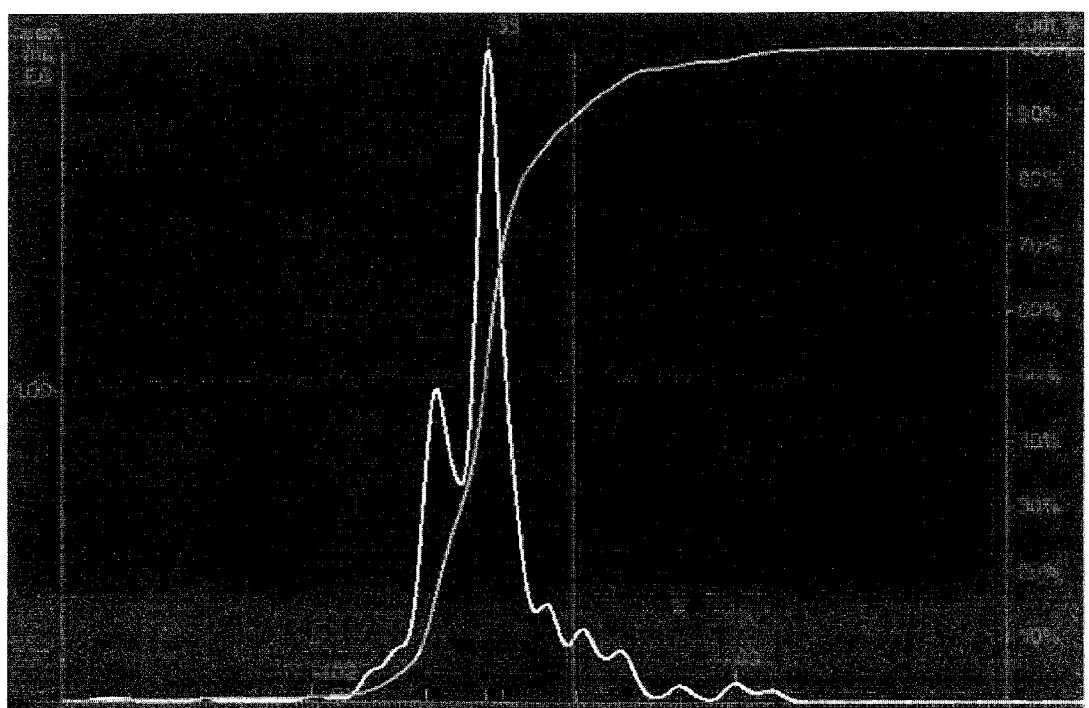

A simulated brine solution that was 0.2 mM in $CaCl_2$ and contained 4 meq of alkalinity was gassed with a simulated flue gas in which $CO_2$ was present to saturation. At this point, the pH of the saturated brine solution was pH 5.30. The solution was passed through a reverse osmosis (R.O.) filter element under 400 psi of pressure multiple times to remove acidic components from the solution. The solution was analyzed after two and four passes using an NS500 nanoparticle tracking analyzer to detect the presence of liquid condensed phase (LCP) droplets in the resultant bicarbonate rich product (BRP). After two passes, the pH solution had risen to a value of 6.8 and LCP droplets were detected. The size of the droplets and the zeta potential of the droplets was measured and the results are shown in FIGS. 15A and B, respectively. The values are consistent with the values obtained for size and zeta potential for the LCP droplets made with $NaHCO_3$ salt. After the solution was passed through the R.O. unit four times, the pH of the solution increased to a value of 7.3 and was concentrated in $CaCl_2$ and $HCO_3^-$ which lead to the formation of a crystalline material, which is solid $CaCO_3$ based on the observed scattering behavior.

Notwithstanding the appended claims, the disclosure is also defined by the following clauses:

1. A method of removing carbon dioxide ($CO_2$) from a $CO_2$ containing gas, the method comprising:
    contacting the gas with an aqueous medium under conditions sufficient to produce a bicarbonate rich product;
    to remove $CO_2$ from the $CO_2$ containing gas.
2. The method according to Clause 1, wherein the aqueous medium is a bicarbonate buffered aqueous medium.
3. The method according to Clause 2, wherein the bicarbonate buffered aqueous medium has a pH ranging from 8 to 10.
4. The method according to Clauses 1, 2 or 3, wherein the $pCO_2$ of the $CO_2$ containing gas in contact with bicarbonate buffered aqueous medium is $10^4$ Pa or higher.
5. The method according to any of the preceding clauses, wherein the bicarbonate rich product comprises droplets of a liquid condensed phase (LCP) in a bulk liquid.
6. The method according to any of the preceding clauses, wherein the $CO_2$ containing gas is contacted with the aqueous medium in the presence of a catalyst that mediates the conversion of $CO_2$ to bicarbonate.
7. The method according to Clause 6, wherein the catalyst is an enzyme.
8. The method according to Clause 7, wherein the enzyme is a carbonic anhydrase.
9. The method according to Clause 6, wherein the catalyst is a synthetic catalyst.
10. The method according to Clause 6, wherein the catalyst is a metal colloid particle catalyst.
11. The method according to any of the preceding clauses, wherein the $CO_2$ containing gas is contacted with the aqueous medium in the presence of a silica source.
12. The method according to any of the preceding clauses, wherein the $CO_2$ containing gas is contacted with the aqueous medium in the presence of an LCP promoter.
13. The method according to any of the preceding clauses, further comprising combining the bicarbonate rich product or a component thereof with a cation source under conditions sufficient to produce a solid carbonate composition.
14. The method according to Clause 13, wherein the cation source is a source of divalent cations.
15. The method according to Clause 14, wherein the divalent cations are alkaline earth metal cations.
16. The method according to Clause 15, wherein the divalent alkaline earth metal cations are selected from the group consisting of $Ca^{2+}$ and $Mg^{2+}$, and combinations thereof.
17. The method according to any of Clauses 13 to 16, wherein the solid carbonate composition is produced without the use of an alkalinity source.
18. The method according to any of Clauses 13 to 17, wherein the method further comprises producing a commodity from the solid carbonate composition.
19. The method according to Clause 18, wherein the commodity is a building material.
20. The method according to Clause 19, wherein the building material is an aggregate.

21. The method according to Clause 19, wherein the building material is a cement or supplemental cementitious material.

22. The method according to any of Clauses 1 to 12, wherein the method comprises storing the bicarbonate rich product for a period of time following production.

23. The method according to any of Clauses 1 to 12, wherein the method comprises combining the bicarbonate rich product with a hydraulic cement.

24. The method according to any of Clauses 1 to 12, wherein the method comprises combining the bicarbonate rich product with a chemical admixture.

25. The method according any of Clauses 5 to 24, wherein the concentration of bicarbonate anions in the LCP droplets is 10,000 ppm or higher.

26. The method according to any of Clauses 5 to 25, wherein the molar ratio of bicarbonate to carbonate anion in the LCP droplets is 10 or greater to 1.

27. The method according to any of the preceding clauses, wherein the reaction is a continuous reaction.

28. The method according to any of the preceding clauses, wherein the reaction is a batch reaction.

29. The method according to any of the preceding clauses, wherein the method is a method of sequestering $CO_2$.

30. The method according to any of the preceding clauses, wherein the method produces a mole of purified $CO_2$ for every two moles of $CO_2$ removed from the gaseous stream to transform a dilute flue gas to a concentrate near-pure stream of $CO_2$.

31. The method according to any of the preceding clauses, wherein the $CO_2$ containing gas is obtained from an industrial plant.

32. A system for removing $CO_2$ from a $CO_2$ containing gas, the system comprising:

a source of the $CO_2$ containing gas;

a source of an aqueous medium; and a reactor configured to contact the $CO_2$ containing gas with the aqueous medium under conditions sufficient to produce a bicarbonate rich product.

33. The system according to Clause 32, wherein the reactor comprises a catalyst that mediates the conversion of $CO_2$ to bicarbonate.

34. The system according to any of Clauses 32 to 33, wherein the source of the $CO_2$ containing gas is an industrial plant.

35. The system according to Clause 34, wherein the source of the $CO_2$ containing gas is flue gas.

36. The system according to Clause 35, wherein the industrial plant is a power plant, cement plant or modular, gas-fired engine (or whatever you want to term the Wartsila engines).

37. The system according to any of Clauses 32 to 36, wherein the aqueous medium is groundwater, sea water or brine water.

38. The system according to any of Clauses 32 to 37, wherein the system is configured to produce a solid carbonate composition from the bicarbonate rich product.

39. The system according to any of Clauses 32 to 38, wherein the system does not include an alkalinity source.

40. The system according to any of Clauses 32 to 39, wherein the system is co-located with an industrial plant.

41. A method of producing a bicarbonate rich product (BRP), the method comprising: combining:

a carbon dioxide ($CO_2$) source;

an aqueous phase; and a liquid condensed phase (LCP) promoter;

in a continuous BRP production reactor under conditions sufficient to produce a BRP; and obtaining the BRP composition from the BRLCP production reactor.

42. The method according to Clause 41, wherein the LCP promoter comprises an LCP promoting cation.

43. The method according to Clause 42, wherein the LCP promoting cation comprises a divalent alkaline earth metal cation.

44. The method according to Clause 43, wherein the divalent alkaline earth metal cation is selected from the group consisting of $Ca^{2+}$ and $Mg^{2+}$ and combinations thereof.

45. The method according to any of Clauses 41 to 44, wherein the LCP promoter further comprises a counter-anion.

46. The method according to any of Clauses 41 to 45, wherein the BRP production reactor is configured to output a BRP composition and a non-BRP composition.

47. The method according to Clause 46, wherein the BRP composition comprises the LCP promoting cation and the non-BRP composition comprises the counter-anion.

48. The method according to any of Clauses 45 to 47, wherein the counter-anion is $Cl^-$.

49. The method according to any of Clauses 45 to 48, wherein the BRP production reactor is configured to selectively separate the counter-anion from the BRP composition.

50. The method according to Clause 49, wherein the BRP production reactor is configured to electrically separate the counter-anion from the BRP composition.

51. The method according to Clause 49, wherein the BRP production reactor is configured to size separate the counter-anion from the BRP composition.

52. The method according to Clause 51, wherein the BRP production reactor comprises a selective membrane that the counter-anion can pass through.

53. The method according to Clause 52, wherein the membrane is a size selective membrane.

54. The method according to any of the preceding clauses, wherein the carbon dioxide ($CO_2$) source; the aqueous phase; and the liquid condensed phase (LCP) promoter are combined under pressure.

55. The method according to Clause 52, wherein the carbon dioxide ($CO_2$) source; the aqueous phase; and the liquid condensed phase (LCP) promoter are combined at a pressure ranging from 50 to 1000 psi.

56. The method according to any of Clauses 41 to 55, wherein the BRP reactor is a single stage reactor.

57. The method according to any of Clauses 41 to 55, wherein the BRLCP reactor is a multi-stage reactor that includes at least a first and second stage.

58. The method according to Clause 57, wherein the process conditions in the first and second stage are different.

59. The method according to any of Clauses 41 to 58, wherein the BRP comprises substantially little, if any, chloride ion.

60. The method according to any of Clauses 41 to 59, wherein the reactor comprises a cathode configured to remove $H^+$ from the contents of the reactor.

61. A continuous bicarbonate rich product (BRP) reactor, the reactor comprising:
  a first end and a second end, wherein the first end is configured to receive:
    a carbon dioxide ($CO_2$) source;
    an aqueous phase; and
    a liquid condensed phase (LCP) promoter; and
  the second end is configured to output a BRP composition.
62. The reactor according to Clause 61, wherein the reactor comprises a separator configured to separate a BRP composition from a non-BRP composition.
63. The reactor according to Clause 62, wherein the separator comprises a size-based separator.
64. The reactor according to Clause 63, wherein the size-based separator comprises a membrane.
65. The reactor according to Clause 64, wherein the membrane is a nano-filtration membrane.
66. The reactor according to Clause 64, wherein the membrane is an ultra-filtration membrane.
67. The reactor according to any of Clauses 61 to 66, wherein the reactor is a single stage reactor.
68. The reactor according to any of Clauses 61 to 66, wherein the reactor is multi-stage reactor.
69. The reactor according to any of Clauses 61 to 68, wherein the reactor comprises a tubular housing and an inner tubular membrane.
70. A system comprising a reactor according to any of Clauses 61 to 69 operatively coupled to a source of $CO_2$.
71. The system according to Clause 70, wherein the source of $CO_2$ comprises an industrial plant.
72. The system according to any of Clauses 70 or 71, wherein the reactor is operatively coupled to a carbonate precipitation reactor.
73. A method of producing a cementitious composition, the method comprising combining:
  a cement component; and
  a bicarbonate rich product (BRP);
    in a manner sufficient to produce a cementitious composition.
72. The method according to Clause 73, wherein the BRP is a composition produced according to the method of any of Clauses 1 to 31 and 41 to 60.
73. The method according to any of Clauses 71 to 72, wherein the bicarbonate additive is a liquid.
74. The method according to any of Clauses 71 to 73, wherein the cement is a hydraulic cement.
75. The method according to Clause 74, wherein the hydraulic cement is a Portland cement.
76. The method according to any Clauses 71 to 75, wherein the settable cementitious composition further comprises an aggregate.
77. The method according to any Clauses 71 to 75, wherein the settable cementitious composition further comprises a non-bicarbonate additive.
78. The method according to Clause 77, wherein the non-bicarbonate additive is a chemical admixture selected from the group consisting of: a water-reducing additive; an air-entraining additive; a set-controlling additive; a retarding additive; an accelerating additive; a workability additive; a corrosion-inhibiting additive; a shrinkage-reducing additive; a permeability-modulating additive; a cold weather cement additive; an underwater cement additive; and combinations thereof.
79. The method according to Clause 78, wherein the chemical admixture is combined with the BRP prior to combination with the cement component.
80. A method according to any of Clauses 73 to 79, wherein the cementitious composition further comprises one or more of a fly ash, a slag and/or pozzolan component.
81. A cementitious composition produced according to the method of any of Clauses 71 to 77.
81. A method of fabricating a structure, the method comprising:
  positioning a settable cementitious composition according to Clause 81 at a location; and
  allowing the settable cementitious composition to set into a solid product at the location.
82. A liquid $CO_2$ sequestering bicarbonate additive.
83. A solid bicarbonate additive produced by separating water from a liquid bicarbonate additive according to Clause 82.
84. A method of producing a $CO_2$ sequestering cement additive composition, the method comprising:
  combining a chemical admixture and a source of $CO_2$ in a manner sufficient to produce the $CO_2$ sequestering cement additive composition.
85. A kit comprising:
  a cement; and
  a bicarbonate rich product (BRP).
86. The kit according to Clause 85, wherein the BRP is a composition produced according to the method of any of Clauses 1 to 31 and 41 to 60.
87. The kit according to Clauses 85 or 86, wherein the kit further comprises a chemical admixture.
88. The kit according to Clause 87, wherein the chemical admixture is combined with the BRP in the kit.
89. A bicarbonate liquid with a $\delta^{18}O$ (SMOW) value of 10 or less.
90. A bicarbonate liquid with a negative $\delta^{13}C$ (PDB) value.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method of removing carbon dioxide ($CO_2$) from a $CO_2$ containing gas, the method comprising:
    contacting the gas with a bicarbonate buffered aqueous medium to produce a bicarbonate rich product; and
    combining the bicarbonate rich product or a component thereof with a cation source to produce a solid carbonate composition without the use of an additional alkalinity source;
    to remove $CO_2$ from the $CO_2$ containing gas.

2. The method according to claim 1, wherein the bicarbonate buffered aqueous medium has a pH ranging from 8 to 10.

3. The method according to claim 1, wherein the $pCO_2$ of the $CO_2$ containing gas in contact with bicarbonate buffered aqueous medium is $10^4$ Pa or higher.

4. The method according to claim 1, wherein the $CO_2$ containing gas is contacted with the aqueous medium in the presence of an LCP promoter.

5. The method according to claim 1, wherein the reaction is a continuous reaction.

6. The method according to claim 1, wherein the reaction is a batch reaction.

7. The method according to claim 1, wherein the method is a method of sequestering $CO_2$.

8. The method according to claim 1, wherein the $CO_2$ containing gas is obtained from an industrial plant.

9. The method according to claim 1, wherein the aqueous medium comprises an amine.

10. The method according to claim 1, wherein the bicarbonate rich product comprises droplets of a liquid condensed phase (LCP) in a bulk liquid.

11. The method according to claim 10, wherein the concentration of bicarbonate anions in the LCP droplets is 10,000 ppm or higher.

12. The method according to claim 1, wherein the $CO_2$ containing gas is contacted with the aqueous medium in the presence of a catalyst that mediates the conversion of $CO_2$ to bicarbonate.

13. The method according to claim 12, wherein the catalyst is an enzyme.

14. The method according to claim 1, wherein the cation source is a source of divalent cations.

15. The method according to claim 14, wherein the divalent cations are alkaline earth metal cations.

16. The method according to claim 15, wherein the divalent alkaline earth metal cations are selected from the group consisting of $Ca^{2+}$ and $Mg^{2+}$, and combinations thereof.

17. The method according to claim 1, wherein the method further comprises producing a commodity from the solid carbonate composition.

18. The method according to claim 17, wherein the commodity is a building material.

19. The method according to claim 18, wherein the building material is a cement or supplemental cementitious material.

20. A method of removing carbon dioxide ($CO_2$) from a $CO_2$ containing gas obtained from an industrial plant, the method comprising:
    contacting the gas obtained from the industrial plant with a bicarbonate buffered aqueous medium having a pH ranging from 8 to 10 to produce a bicarbonate rich product comprising droplets of a liquid condensed phase (LCP) in a bulk liquid;
    combining the bicarbonate rich product or a component thereof with a cation source to produce a solid carbonate composition without the use of an additional alkalinity source; and
    producing a commodity from the solid carbonate composition;
    to remove $CO_2$ from the $CO_2$ containing gas.

21. The method according to claim 20, wherein the industrial plant is a power plant.

22. A method of removing carbon dioxide ($CO_2$) from a $CO_2$ containing gas obtained from an industrial plant, the method comprising:
    contacting the gas obtained from the industrial plant with a bicarbonate buffered aqueous medium having a pH ranging from 8 to 10 to produce a bicarbonate rich product comprising droplets of a liquid condensed phase (LCP) in a bulk liquid;
    combining the bicarbonate rich product or a component thereof with a cation source to produce a solid carbonate composition without the use of an additional alkalinity source; and
    producing an aggregate from the solid carbonate composition;
    to remove $CO_2$ from the $CO_2$ containing gas and produce purified $CO_2$ from the gaseous stream.

* * * * *